United States Patent
Metcalf et al.

(10) Patent No.: US 9,018,210 B2
(45) Date of Patent: Apr. 28, 2015

(54) SUBSTITUTED BENZALDEHYDE COMPOUNDS AND METHODS FOR THEIR USE IN INCREASING TISSUE OXYGENATION

(71) Applicants: Global Blood Therapeutics, Inc., Boston, MA (US); Cytokinetics, Inc., South San Francisco, CA (US); The Regents of the University of California, Oakland, CA (US)

(72) Inventors: Brian Metcalf, Moraga, CA (US); Chihyuan Chuang, Millbrae, CA (US)

(73) Assignees: Global Blood Therapeutics, Inc., South San Francisco, CA (US); Cytokinetics, Inc., South San Francisco, CA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 13/730,674

(22) Filed: Dec. 28, 2012

(65) Prior Publication Data
US 2013/0190315 A1    Jul. 25, 2013

Related U.S. Application Data

(60) Provisional application No. 61/661,320, filed on Jun. 18, 2012, provisional application No. 61/581,053, filed on Dec. 28, 2011.

(51) Int. Cl.
*C07D 487/04* (2006.01)
*C07D 215/14* (2006.01)
*C07D 471/04* (2006.01)

(52) U.S. Cl.
CPC ............ *C07D 487/04* (2013.01); *C07D 215/14* (2013.01); *C07D 471/04* (2013.01)

(58) Field of Classification Search
None
See application file for complete search history.

(56) References Cited

U.S. PATENT DOCUMENTS

| | | | |
|---|---|---|---|
| 3,236,893 A | 2/1966 | Blout et al. | |
| 4,062,858 A | 12/1977 | Hoehn et al. | |
| 4,478,834 A | 10/1984 | Shroff et al. | |
| 5,185,251 A | 2/1993 | Chen et al. | |
| 5,202,243 A | 4/1993 | Balani | |
| 5,290,941 A | 3/1994 | Volante et al. | |
| 5,403,816 A | 4/1995 | Takabe et al. | |
| 5,760,232 A | 6/1998 | Chen et al. | |
| 5,994,353 A | 11/1999 | Breault | |
| 6,214,817 B1 | 4/2001 | Riley et al. | |
| 6,232,320 B1 | 5/2001 | Stewart et al. | |
| 6,355,661 B1 | 3/2002 | Lai et al. | |
| 6,630,496 B1 | 10/2003 | McKew et al. | |
| 7,160,910 B2 | 1/2007 | Safo et al. | |
| 7,411,083 B2 | 8/2008 | Gopalsamy et al. | |
| 2001/0046997 A1 | 11/2001 | Abraham et al. | |
| 2002/0095035 A1 | 7/2002 | Warshawsky et al. | |
| 2002/0142995 A1* | 10/2002 | Nicolau et al. | 514/102 |
| 2003/0022923 A1 | 1/2003 | Lai et al. | |
| 2003/0073712 A1* | 4/2003 | Wang et al. | 514/277 |
| 2003/0165714 A1 | 9/2003 | Lee et al. | |
| 2003/0187026 A1 | 10/2003 | Li et al. | |
| 2003/0190333 A1 | 10/2003 | Mossman et al. | |
| 2003/0199511 A1 | 10/2003 | Li et al. | |
| 2004/0186077 A1 | 9/2004 | Diakur et al. | |
| 2004/0209921 A1 | 10/2004 | Bridger et al. | |
| 2005/0085484 A1 | 4/2005 | Mitchell et al. | |
| 2005/0159605 A1 | 7/2005 | Tarur et al. | |
| 2006/0094761 A1 | 5/2006 | Haque et al. | |
| 2008/0114167 A1 | 5/2008 | Castro et al. | |
| 2009/0143371 A1 | 6/2009 | Buettelmann et al. | |
| 2009/0163512 A1 | 6/2009 | Chen et al. | |
| 2009/0312315 A1 | 12/2009 | Yamaguchi et al. | |
| 2010/0204235 A1 | 8/2010 | Lizos et al. | |
| 2010/0311748 A1 | 12/2010 | Dakin et al. | |

FOREIGN PATENT DOCUMENTS

| | | |
|---|---|---|
| CN | 101113148 A | 1/2008 |
| CN | 102116772 A | 7/2011 |
| DE | 2238734 A1 | 2/1973 |
| DE | 2238628 A1 | 3/1973 |
| DE | 2853765 A1 | 6/1980 |
| DE | 2904829 A1 | 8/1980 |
| DE | 3503435 A1 | 8/1985 |
| DE | 3431004 A1 | 3/1986 |
| DE | 3704223 A1 | 8/1987 |
| DE | 258226 A1 | 7/1988 |
| DE | 276479 A1 | 2/1990 |
| DE | 3931954 A1 | 3/1990 |

(Continued)

OTHER PUBLICATIONS

Ijeoma N. Nnamania et al. "Pyridyl Derivatives of Benzaldehyde as Potential Antisickling Agents", Chemistry and Biodiversity, vol. 5, 2008, p. 1762-1769.*
Beddell, C.R. Substituted benzaldehydes designed to increase the oxygen affinity of human haemoglobin and inhibit the sickling of sickle erythrocytes, Br. J. Pharmac. (1984), 82, 397-407.*
Neelima, B.A., "A novel annelation reaction:" Chemistry and Industry (London, UK), 1986, (4), 141-2.*
Bacsa et al., "Novel products from Baylis-Hillman reactions of salicylaldehydes," South African Journal of Chemistry (1998), 51(1), 47-54 CODEN: SAJCDG; ISSN: 0379-4350.

(Continued)

*Primary Examiner* — Soren Harward
*Assistant Examiner* — Jeanmarie Calvillo
(74) *Attorney, Agent, or Firm* — Kilpatrick Townsend & Stockton LLP

(57) ABSTRACT

Provided are substituted benzaldehydes and derivatives thereof that act as allosteric modulators of hemoglobin, methods and intermediates for their preparation, pharmaceutical compositions comprising the modulators, and methods for their use in treating disorders mediate by hemoglobin and disorders that would benefit from increased tissue oxygenation.

6 Claims, No Drawings

(56) References Cited

FOREIGN PATENT DOCUMENTS

| | | |
|---|---|---|
| DE | 4318550 A1 | 12/1994 |
| DE | 4442050 A1 | 5/1996 |
| EP | 10063 A2 | 4/1980 |
| EP | 278686 A1 | 8/1988 |
| EP | 291916 A1 | 11/1988 |
| EP | 303465 A2 | 2/1989 |
| EP | 336369 A1 | 10/1989 |
| EP | 0348155 A1 | 12/1989 |
| EP | 0401517 A1 | 12/1990 |
| EP | 453210 A2 | 10/1991 |
| EP | 462800 A2 | 12/1991 |
| EP | 481802 A1 | 4/1992 |
| EP | 498380 A1 | 8/1992 |
| EP | 0528337 A1 | 2/1993 |
| EP | 0542372 A1 | 5/1993 |
| EP | 567133 A1 | 10/1993 |
| EP | 0640609 A1 | 3/1995 |
| EP | 0747393 A1 | 12/1996 |
| FR | 2 217 016 A1 | 9/1974 |
| FR | 2909379 A1 | 6/2008 |
| GB | 1593417 A | 7/1981 |
| JP | 61040236 A | 2/1986 |
| JP | 06041118 A | 2/1994 |
| JP | 07025882 A | 1/1995 |
| JP | 2006342115 A | 12/2006 |
| JP | 2009203230 A | 9/2009 |
| WO | 91/91697 A1 | 12/1991 |
| WO | 92/02503 A1 | 2/1992 |
| WO | 93/17013 A1 | 9/1993 |
| WO | 94/01406 A1 | 1/1994 |
| WO | 95/14015 A1 | 5/1995 |
| WO | 95/21854 A1 | 8/1995 |
| WO | 96/11902 A1 | 4/1996 |
| WO | 97/44306 A1 | 11/1997 |
| WO | 98/08818 A1 | 3/1998 |
| WO | 98/21199 A2 | 5/1998 |
| WO | 99/43672 A1 | 9/1999 |
| WO | 99/47529 A1 | 9/1999 |
| WO | 99/59978 A1 | 11/1999 |
| WO | 99/62908 A2 | 12/1999 |
| WO | 00/35858 A1 | 6/2000 |
| WO | 00/40564 A1 | 7/2000 |
| WO | 00/75145 A1 | 12/2000 |
| WO | 01/00612 A2 | 1/2001 |
| WO | 01/19823 A2 | 3/2001 |
| WO | 01/23383 A1 | 4/2001 |
| WO | 01/36375 A1 | 5/2001 |
| WO | 01/57044 A1 | 8/2001 |
| WO | 01/62705 A2 | 8/2001 |
| WO | 01/75006 A1 | 8/2001 |
| WO | 01/70663 A2 | 9/2001 |
| WO | 02/00622 A2 | 1/2002 |
| WO | 02/12235 A1 | 2/2002 |
| WO | 02/24635 A2 | 3/2002 |
| WO | 02/24679 A1 | 3/2002 |
| WO | 02/051849 A1 | 7/2002 |
| WO | 02/053547 A1 | 7/2002 |
| WO | 03/051366 A2 | 6/2003 |
| WO | 03/053368 A2 | 7/2003 |
| WO | 03/101959 A1 | 12/2003 |
| WO | 2004/018430 A1 | 3/2004 |
| WO | 2004/024705 A1 | 3/2004 |
| WO | 2004/056727 A2 | 7/2004 |
| WO | 2004/058790 A1 | 7/2004 |
| WO | 2005/074513 A2 | 8/2005 |
| WO | 2005/077932 A2 | 8/2005 |
| WO | 2005/087766 A1 | 9/2005 |
| WO | 2006/011469 A1 | 2/2006 |
| WO | 2006/088173 A1 | 8/2006 |
| WO | 2006/103463 A1 | 10/2006 |
| WO | 2006/106711 A1 | 10/2006 |
| WO | 2006/116764 A1 | 11/2006 |
| WO | 2007/017267 A2 | 2/2007 |
| WO | 2007/047204 A1 | 4/2007 |
| WO | 2007/049675 A1 | 5/2007 |
| WO | 2007/117180 A1 | 10/2007 |
| WO | 2008/013414 A1 | 1/2008 |
| WO | 2008/016132 A1 | 2/2008 |
| WO | 2008/041118 A2 | 4/2008 |
| WO | 2008/051532 A1 | 5/2008 |
| WO | 2008/060391 A2 | 5/2008 |
| WO | 2008/081096 A2 | 7/2008 |
| WO | 2008/101682 A2 | 8/2008 |
| WO | 2009/001214 A2 | 12/2008 |
| WO | 2009/050183 A2 | 4/2009 |
| WO | 2009/125606 A1 | 10/2009 |
| WO | 2009/130560 A1 | 10/2009 |
| WO | 2009/146555 A1 | 12/2009 |
| WO | 2010/056631 A1 | 5/2010 |
| WO | 2010/129055 A1 | 11/2010 |
| WO | 2011/033045 A1 | 3/2011 |
| WO | 2011/136459 A1 | 11/2011 |
| WO | 2012/141228 A1 | 10/2012 |
| WO | 2013/102145 A1 | 7/2013 |

OTHER PUBLICATIONS

Ballet et al., "Novel selective human melanocortin-3 receptor ligands: Use of the 4-amino-1,2,4,5-tetrahydro-2-benzazepin-3- one (Aba) scaffold," Bioorganic & Medicinal Chemistry Letters (2007), 17(9), 2492-2498 CODEN: BMCLE8; ISSN: 0960-894X.

Baxter et al., "Reductive aminations of carbonyl compounds with borohydride and borane reducing agents," Organic Reactions (Hoboken, NJ, United States) (2002), 59, No pp. given CODEN: ORHNBA URL: http://www3.interscience.wiley.com/cgi-bin/mrwhome/107610747/HOME.

Berge et al., "Pharmaceutical Salts," Journal of Pharmaceutical Science, 1977, 66:1-19.

Bode et al., "Novel synthesis and x-ray crystal structure of a coumarin derivative," South African Journal of Chemistry (1992), 45(1), 25-7 CODEN: SAJCDG; ISSN: 0379-4350.

Britton et al., "Structure-activity relationships of a series of benzothiophene-derived NPY Y1 antagonists: optimization of the C-2 side chain," Bioorganic & Medicinal Chemistry Letters (1999), 9(3), 475-480 CODEN: BMCLE8; ISSN: 0960-894X.

Brown et al., "1,2-Dihydroisoquinolines. III. Dimerization," Tetrahedron (1966), 22(8), 2437-43 CODEN: TETRAB; ISSN: 0040-4020.

Ciganek, "The catalyzed a-hydroxyalkylation and a-aminoalkylation of activated olefins (the Morita-Baylis-Hillman reaction)," Organic Reactions (Hoboken, NJ, United States) (1997), 51, No pp. given CODEN: ORHNBA URL: http://www3.interscience.wiley.com/cgi-bin/mrwhome/107610747/HOME.

Ding et al., "Crystal structure of bis(µ3-oxo)-bis[µ-2-2-(2-formylphenoxy)acetato- O,O']-bis[µ-2-2-(2-formylphenoxy)acetato-O,O']- octakis(n-butyl)tetratin(IV), Sn4O2(C9H7O4)4(C4H9)8," Zeitschrift fuer Kristallographie—New Crystal Structures (2011), 226(1), 31-32 CODEN: ZKNSFT; ISSN: 1433-7266.

Elwahy, "Synthesis of new benzo-substituted macrocyclic ligands containing quinoxaline subunits," Tetrahedron (2000), 56(6), 897-907 CODEN: TETRAB; ISSN: 0040-4020.

Gadaginamath et al., "Synthesis and antibacterial activity of novel 1-butyl-2-phenoxy/2-phenylthio/2-aminomethyl-5- methoxyindole derivatives," Polish Journal of Chemistry (1997), 71(7), 923-928 CODEN: PJCHDQ; ISSN: 0137-5083.

Ghate et al., "Synthesis of vanillin ethers from 4-(bromomethyl) coumarins as anti-inflammatory agents," European Journal of Medicinal Chemistry (2003), 38(3), 297-302 CODEN: EJMCA5; ISSN: 0223-5234.

Gao et al., "A novel one-pot three-step synthesis of 2-(1-benzofuran-2-yl)quinoline-3-carboxylic acid derivatives," Journal of the Brazilian Chemical Society (2010), 21(5), 806-812 CODEN: JOCSET; ISSN: 0103-5053.

Grashey, "The nitro group as a 1,3-dipole in cycloadditions," Angewandte Chemie (1962), 74, 155 CODEN: ANCEAD; ISSN: 0044-8249.

Gunter et al., "Structural control of co-receptor binding in porphyrin-bipyridinium supramolecular assemblies," Journal of the Chemical Society, Perkin Transactions 1: Organic and Bio-Organic Chemistry (1998), (12), 1945-1958 CODEN: JCPRB4; ISSN: 0300-922X.

(56) References Cited

OTHER PUBLICATIONS

Hanmantgad et al., "Synthesis and pharmacological properties of some 4-(2-benzo[b]furanyl)coumarins," Indian Journal of Chemistry, Section B: Organic Chemistry Including Medicinal Chemistry (1986), 25B(7), 779-81 CODEN: IJSBDB; ISSN: 0376-4699.

Jarvest et al., "Discovery and optimisation of potent, selective, ethanolamine inhibitors of bacterial phenylalanyl tRNA synthetase," Bioorganic & Medicinal Chemistry Letters (2005), 15(9), 2305-2309 CODEN: BMCLE8; ISSN: 0960-894X.

Karche et al., "Electronic Effects in Migratory Groups. [1,4]- versus [1,2]-Rearrangement in Rhodium Carbenoid Generated Bicyclic Oxonium Ylides," Journal of Organic Chemistry (2001), 66(19), 6323-6332 CODEN: JOCEAH; ISSN: 0022-3263.

Katritzky et al., "Synthesis of 3-hydroxymethyl-2,3-dihydrobenzofurans and 3-hydroxymethylbenzofurans," ARKIVOC (Gainesville, FL, United States) (2003), (6), 49-61 CODEN: AGFUAR URL: http://www.arkat-usa.org/ark/journal/2003/Vargoglis/AV-622A/622.pdf.

Kaye et al., "Does the DABCO-catalysed reaction of 2-hydroxybenzaldehydes with methyl acrylate follow a Baylis-Hillman pathway?," Organic & Biomolecular Chemistry (2003), 1(7), 1133-1138 CODEN: OBCRAK; ISSN: 1477-0520.

Kaye et al. "DABCO-catalyzed reactions of salicylaldehydes with acrylate derivatives," Synthetic Communications (1996), 26(11), 2085-97 CODEN: SYNCAV; ISSN: 0039-7911.

Kessar et al., "Synthesis of isoindolobenzazepines via photocyclization of N-(2- formylphenethyl)phthalimide derivatives," Indian Journal of Chemistry, Section B: Organic Chemistry Including Medicinal Chemistry (1991), 306(11), 999-1005 CODEN: IJSBDB; ISSN: 0376-4699.

Kessar et al., Tetrahedron Letters (1987), 28(44), 5323-6 CODEN: TELEAY; ISSN: 0040-4039.

Kise et al., "Electroreductive Intramolecular Coupling of Phthalimides with Aromatic Aldehydes: Application to the Synthesis of Lennoxamine," Journal of Organic Chemistry (2011), 76(23), 9856-9860 CODEN: JOCEAH; ISSN: 0022-3263.

Krow, "The Baeyer-Villiger oxidation of ketones and aldehydes," Organic Reactions (Hoboken, NJ, United States) (1993), 43, No pp. given CODEN: ORHNBA URL: http://www3.interscience.wiley.com/cgi-bin/mrwhome/107610747/HOME.

Lakkannavar et al., "4-[2'-benzylideneanilino aryloxymethyl] coumarins E and Z isomers," Indian Journal of Heterocyclic Chemistry (1995), 4(4), 303-4 CODEN: IJCHEI; ISSN: 0971-1627.

Liu et al., "Synthesis of Double-Armed Benzo-15-crown-5 and Their Complexation Thermodynamics with Alkali Cations," Journal of Inclusion Phenomena and Macrocyclic Chemistry (2005), 52(3-4), 229-235 CODON: JIPCF5; ISSN: 1388-3127.

Mahoney et al., "Functionalization of Csp3-H bond-Sc(OTf)3-catalyzed domino 1,5-hydride shift/cyclization/Friedel-Crafts acylation reaction of benzylidene Meldrum's acids," Tetrahedron Letters (2009), 50(33), 4706-4709 CODEN: TELEAY; ISSN: 0040-4039.

Majhi et al, "An efficient synthesis of novel dibenzo-fused nine-membered oxacycles using a sequential Baylis-Hillman reaction and radical cyclization," Synthesis (2008), (1), 94-100 CODEN: SYNTBF; ISSN: 0039-7881.

McKay et al., "7,11,15,28-Tetrakis[(2-formylphenoxy)methyl]-1,21,23,25- tetramethylresorcin[4]arene cavitand ethyl acetate clathrate at 173 K," Acta Crystallographica, Section E: Structure Reports Online (2009), E65(4), o692-o693 CODEN: ACSEBH; ISSN: 16005368 URL: http://journals.iucr.org/e/issues/2009/04/00/fl22 33/fl2233.pdf.

McKay et al., "Microwave-assisted synthesis of a new series of resorcin[4]arene cavitand-capped porphyrin capsules," Organic & Biomolecular Chemistry (2009), 7(19), 3958-3968 CODEN: OBCRAK; ISSN: 1477-0520.

Merlino et al., "Development of second generation amidinohydrazones, thio- and semicarbazones as Trypanosoma cruzi-inhibitors bearing benzofuroxan and benzimidazole 1,3-dioxide core scaffolds," MedChemComm (2010), 1(3), 216-228 CODEN: MCCEAY; ISSN: 2040-2503.

Mitra et al., "Synthesis and biological evaluation of dibenz[b,f][1,5]oxazocine derivatives for agonist activity at κ-opioid receptor," European Journal of Medicinal Chemistry (2011), 46(5), 1713-1720 CODEN: EJMCA5; ISSN: 0223-5234.

Mulwad et al., "Synthesis and antimicrobial activity of [6'-methyl-4'-methoxy-2-oxo-2H-[1]- benzopyran)-2'',4''- dihydro-[1'',2'',4'']-triazol-3''-one and 3''-phenylthiazolidin-4''-one-phenoxymethyl derivatives of dipyranoquinoline," Pharmaceutical Chemistry Journal Ahead of Print CODEN: PCJOAU; ISSN: 0091-150X publisher: Springer, pp. 427-432.

Neelima et al., "A novel annelation reaction: synthesis of 6H-[1]benzopyrano[4,3-b]quinolones," Chemistry & Industry (London, United Kingdom) (1986), (4), 141-2 CODEN: CHINAG; ISSN: 0009-3068.

Nnamani et al., Chemistry & Biodiversity, 2008, vol. 5, pp. 1762-1769.

Nonoyama et al., "Cyclometallation of 2-(2-pyridyl)benzo[b]furan and 1-(2-pyridyl and 2-pyrimidyl)indole with palladium(II) and rhodium(III). Structures of unexpectedly formed nitro palladium(II) complexes," Polyhedron 1999, 533-543 CODEN: PLYHDE; ISSN: 0277-5387.

Nyerges et al., "Synthesis of indazole N-oxides via the 1,7-electrocyclization of azomethine ylides," Tetrahedron Letters (2001), 42(30), 5081-5083 CODEN: TELEAY; ISSN: 0040-4039.

Nyerges et al., "Synthesis of indazole-N-oxides via the 1,7-electrocyclization of azomethine ylides," Tetrahedron (2004), 60(44), 9937-9944 CODEN: TETRAB; ISSN: 0040-4020.

O'Reilly, "Metal-phenoxyalkanoic acid interactions. XXV. The crystal structures of (2-formyl-6-methoxyphenoxy)acetic acid and its zinc(II) complex and the lithium, zinc(II) and cadmium(II) complexes of (2-chlorophenoxy)acetic acid," Australian Journal of Chemistry (1987), 40(7), 1147-59 CODEN: AJCHAS; ISSN: 0004-9425.

Perkins et al., "Manganese(II), iron(II), cobalt(II), and copper(II) complexes of an extended inherently chiral tris-bipyridyl cage," Proceedings of the National Academy of Sciences of the United States of America (2006), 103(3), 532-537 CODEN: PNASA6; ISSN: 0027-8424.

Perez et al., "Preparation of new 1,2-disubstituted ferrocenyl stibine derivatives containing ether/thioether pendant arm from a quaternary ferrocenyl ammonium salt," Polyhedron (2009), 28(14), 3115-3119 CODEN: PLYHDE; ISSN: 0227-5387.

Ruchirawat et al., "A novel synthesis of aporhoeadanes," Tetrahedron Letters (1984), 25(32), 3485-8 CODEN: TELEAY; ISSN: 0040-4039.

Sahakitpichan et al., "A practical and highly efficient synthesis of lennoxamine and related isoindolobenzazepines," Tetrahedron (2004), 60(19), 4169-4172 CODEN: TETRAB; ISSN: 0040-4020.

Sahm et al., "Synthesis of 2-arylbenzofurans," Justus Liebigs Annalen der Chemie (1974), (4), 523-38 CODEN: JLACBF; ISSN: 0075-4617.

Sainsbury et al., "1,2-Dihydroisoquinolines. IV. Acylation," Tetrahedron (1966), 22(8), 244-552 CODEN: TETRAB; ISSN: 0040-4020.

Sarodnick et al., "Quinoxalines XV. Convenient Synthesis and Structural Study of Pyrazolo[1,5-a]quinoxalines," Journal of Organic Chemistry (2009), 74(3), 1282-1287 CODEN: JOCEAH; ISSN: 0022-3263.

Singh et al., "Reductive-Cyclization-Mediated Synthesis of Fused Polycyclic Quinolines from Baylis-Hillman Adducts of Acrylonitrile: Scope and Limitations," European Journal of Organic Chemistry (2009), (20), 3454-3466 CODEN: EJOCFK; ISSN: 1434-193X.

Srivastava et al., "Synthesis and biological evaluation of 4-substituted tetrazolo[4,5-a]quinolines and 2,3-disubstituted quinoline derivatives," Indian Journal of Chemistry, Section B: Organic Chemistry Including Medicinal Chemistry (1989), 28B(7), 562-73 CODEN: IJSBDB; ISSN: 0376-4699.

Starke et al., "Quinoxalines. Part 13: Synthesis and mass spectrometric study of aryloxymethylquinoxalines and benzo[b]furylquinoxalines," Tetrahedron (2004), 60(29), 6063-6078 CODEN: TETRAB; ISSN: 0040-4020.

Swann et al., "Rates of reductive elimination of substituted nitrophenols from the (indol-3-yl)methyl position of

(56) References Cited

OTHER PUBLICATIONS indolequinones," Journal of the Chemical Society, Perkin Transactions 2 (2001), (8), 1340-1345 CODEN: JCSPGI; ISSN: 1472-779X.
Tome et al., "Product class 13: 1,2,3-triazoles," Science of Synthesis (2004), 13, 415-601 CODEN: SSCYJ9.
VanRompaey et al., "A versatile synthesis of 2-substituted 4-amino-1,2,4,5-tetrahydro-2-benzazepine-3-ones," Tetrahedron (2003), 59(24), 4421-4432 CODEN: TETRAB; ISSN: 0040-4020.
VanRompaey et al., "Synthesis and evaluation of the β-turn properties of 4-amino-1,2,4,5-tetrahydro-2-benzazepin-3-ones and of their spirocyclic derivative," European Journal of Organic Chemistry (2006), (13), 2899-2911 CODEN: EJOCFK; ISSN: 1434-193X.
Vicente et al., "Carbopalladation of Maleate and Fumarate Esters and 1,1-Dimethylallene with Ortho-Substituted Aryl Palladium Complexes," Organometallics (2010), 29(2), 409-416.
Wang et al., "Studies of Benzothiophene Template as Potent Factor IXa (FIXa) Inhibitors in Thrombosis," Journal of Medicinal Chemistry (2010), 53(4), 1465-1472 CODEN: JMCMAR; ISSN: 0022-2623.
Warshawsky et al., "The synthesis of aminobenzazepinones as antiphenylalanine dipeptide mimics and their use in NEP inhibition," Bioorganic & Medicinal Chemistry Letters (1996), 6(8), 957-962 CODEN: BMCLE8; ISSN: 0960-894X.
Yan et al., "Synthesis, crystal structure and antibacterial activity of di-n-butyltin di-2-(2-formylphenoxy)acetic ester," Yingyong Huaxue (2007), 24(6), 660-664 CODEN: YIHUED; ISSN: 1000-0518.
Yan et al., "Synthesis, crystal structure and antibacterial activity of dibutyltin carboxylate," Huaxue Tongbao (2007), 70(4), 313-316 CODEN: HHTPAU; ISSN: 0441-3776.
Zhang et al., "DFT study on Ru11-catalyzed cyclization of terminal alkynals to cycloalkenes," International Journal of Quantum Chemistry (2009), 109(4), 679-687 CODEN: IJQCB2; ISSN: 0020-7608.
Zwaagstra et al., "Synthesis and Structure-Activity Relationships of Carboxylated Chalcones: A Novel Series of Cys-LT1 (LTD4) Receptor Antagonists," Journal of Medicinal Chemistry (1997), 40(7), 1075-1089 CODEN: JMCMAR; ISSN: 0022-2623.
Chemical Abstract Registry No. 1142191-55-6, Indexed in the Registry File on STN CAS ONLINE May 4, 2009, 3 pages.
Ito et al., "A medium-term rat liver bioassay for rapid in vivo detection of carcinogenic potential of chemicals," Cancer Science, Jan. 2003, vol. 94(1), pp. 3-8.
Wendt et al., "Synthesis and SAR of 2-aryl pyrido[2,3-d]pyrimidines as potent mGlu5 receptor antagonists," Bioorganic & Medicinal Chemistry Letters 17, 2007, pp. 5396-5399.
PUBCHEM CID 54009805 Create date: Dec. 4, 2011 p. 1.
PUBCHEM CID 54883281 Create date: Aug. 19, 2012 p. 1.
Abdulmalik et al., "Sickle cell disease: current therapeutic approaches," Expert Opinion Ther. Patents, 2005, vol. 15(11), pp. 1497-1506.
Abraham et al., "Vanillin, a Potential Agent for the Treatment of Sickle Cell Anemia," Blood, Mar. 2005, vol. 77(6), pp. 1334-1341.
Cherian et al., "Structure—Activity Relationships of Antitubercular Nitroimidazoles.3. Exploration of the Linker and Lipophilic Tail of ((S)-2-Nitro-6,7-dihydro-5H-imidazo[2,1-b][1,3]oxazin-6-yl)-(4-trifluoromethoxybenzyl)amine (6-Amino PA-824).," J. Med. Chem., Aug. 2011, vol. 54(16), pp. 5639-5659.
Database CA Chemical Abstract Service, Li et al., "Substituted-benzoheterocycle derivatives, preparation, and application for preparation of antiviral or antineoplastic drugs," XP002726578 retrieved from STN Database accession No. 2013:366779 (abstract); RN: 1427163-92-5 & CN 102 952 062 A, Mar. 6, 2013, 2 pages.
Marchetti et al., "Synthesis and biological evaluation of 5-substituted $O^4$-alkylpyrimidines as CDK2 inhibitors," Org. Biomol. Chem, 2010, vol. 8, pp. 2397-2407.
Mesguiche et al., "4-Alkoxy-2,6-diaminopyrimidine Derivatives: Inhibitors of Cyclin Dependent Kinases 1 and 2," Bioorganic & Medicinal Chemistry Letters, Jan. 2003, vol. 13, pp. 217-222.

\* cited by examiner

SUBSTITUTED BENZALDEHYDE COMPOUNDS AND METHODS FOR THEIR USE IN INCREASING TISSUE OXYGENATION

REFERENCES TO RELATED APPLICATIONS

The present application claims priority to U.S. Provisional Application No. 61/581,053, filed Dec. 28, 2011, and U.S. Provisional Application No. 61/661,320, filed Jun. 18, 2012, the entirety of which are incorporated herein by reference.

FIELD OF THE INVENTION

The present invention generally relates to substituted benzaldehydes and derivatives thereof that act as allosteric modulators of hemoglobin, methods and intermediates for their preparation, pharmaceutical compositions comprising the modulators, and methods for their use in treating disorders mediate by hemoglobin and disorders that would benefit from increased tissue oxygenation.

BACKGROUND OF THE INVENTION

Hemoglobin (Hb) is a tetrameric protein in red blood cells that transports up to four oxygen molecules from the lungs to various tissues and organs throughout the body. Hemoglobin binds and releases oxygen through conformational changes, and is in the tense (T) state when it is unbound to oxygen and in the relaxed (R) state when it is bound to oxygen. The equilibrium between the two conformational states is under allosteric regulation. Natural compounds such as 2,3-bisphosphoglycerate (2,3-BPG), protons, and carbon dioxide stabilize hemoglobin in its de-oxygenated T state, while oxygen stabilizes hemoglobin in its oxygenated R state. Other relaxed R states have also been found, however their role in allosteric regulation has not been fully elucidated.

Sickle cell disease is a prevalent disease particularly among those of African and Mediterranean descent. Sickle hemoglobin (HbS) contains a point mutation where glutamic acid is replaced with valine, allowing the T state to become susceptible to polymerization to give the HbS containing red blood cells their characteristic sickle shape. The sickled cells are also more rigid than normal red blood cells, and their lack of flexibility can lead to blockage of blood vessels. Certain synthetic aldehydes have been found to shift the equilibrium from the polymer forming T state to the non-polymer forming R state (Nnamani et al. Chemistry & Biodiversity Vol. 5, 2008 pp. 1762-1769) by acting as allosteric modulators to stabilize the R state through formation of a Schiff base with an amino group on hemoglobin.

U.S. Pat. No. 7,160,910 discloses 2-furfuraldehydes and related compounds that are also allosteric modulators of hemoglobin. One particular compound 5-hydroxymethyl-2-furfuraldehyde (5HMF) was found to be a potent hemoglobin modulator both in vitro and in vivo. Transgenic mice producing human HbS that were treated with 5HMF were found to have significantly improved survival times when exposed to extreme hypoxia (5% oxygen). Under these hypoxic conditions, the 5HMF treated mice were also found to have reduced amounts of hypoxia-induced sickled red blood cells as compared to the non-treated mice.

A need exists for therapeutics that can shift the equilibrium between the deoxygenated and oxygenated states of Hb to treat disorders that are mediated by Hb or by abnormal Hb such as HbS. A need also exists for therapeutics to treat disorders that would benefit from having Hb in the R state with an increased affinity for oxygen. Such therapeutics would have applications ranging, for example, from sensitizing hypoxic tumor cells that are resistant to standard radiotherapy or chemotherapy due to the low levels of oxygen in the cell, to treating pulmonary and hypertensive disorders, and to promoting wound healing.

BRIEF SUMMARY OF THE INVENTION

The present invention provides, in one aspect, allosteric modulators of hemoglobin. In another aspect, provided are pharmaceutical compositions comprising the allosteric modulators disclosed herein. In other aspects, provided are methods for treating disorders mediated by hemoglobin and methods for increasing tissue oxygenation for treating disorders that would benefit from increased oxygenation, such methods comprising administering the allosteric modulators disclosed herein to a subject in need thereof. In still other aspects, provided are methods for preparing the allosteric modulators disclosed herein. These and other embodiments of the invention are more fully described in the description that follows.

DETAILED DESCRIPTION OF THE INVENTION

I. Definitions

As used herein, the below terms have the following meanings unless specified otherwise.

The abbreviations used herein are conventional, unless otherwise defined: aq=aqueous; Boc=t-butylcarboxy, $(Boc)_2O$=di-tert-butyl dicarbonate, °C.=degrees celcius, mCPBA=m-chloroperoxybenzoic acid, DCM=dichloromethane $(CH_2Cl_2)$, DIBAL=diisobutylaluminum hydride, DMF=dimethyl formamide, EtOAc=ethyl acetate, g=gram, H2=hydrogen; H2O=water; HBr=hydrogen bromide; HCl=hydrogen chloride, HPLC=high pressure liquid chromatography, h=hour, LAH=lithium aluminum hydride (LiAlH4); MeCN=acetonitrile; MS=Mass Spectrum, m/z=mass to charge ratio, MHz=Mega Hertz, MeOH=methanol, µM=micromolar, µL=microliter, mg=milligram, mM=millimolar, mmol=millimole, mL=milliliter, min=minute, M=molar, Na2CO3=sodium carbonate, ng=nanogram, N=Normal, NMR=nuclear magnetic resonance, Pd/C=palladium on carbon, rp=reverse phase, sat=saturated, rt=room temperature, TEA=triethylamine, THF=tetrahydrofuran, TFA=trifluoroacetic acid, TLC=thin layer chromatography, and TMS=trimethylsilyl.

It is noted here that as used in this specification and the appended claims, the singular forms "a," "an," and "the" include plural reference unless the context clearly dictates otherwise.

"Alkoxy" refers to —O(alkyl) where alkyl as defined herein. Representative examples of alkoxy groups include methoxy, ethoxy, t-butoxy, and the like.

"Alkyl," by itself or as part of another substituent, means, unless otherwise stated, a straight or branched chain, fully saturated aliphatic hydrocarbon radical having the number of carbon atoms designated. For example, "$C_{1-8}$alkyl" refers to a hydrocarbon radical straight or branched, containing from 1 to 8 carbon atoms that is derived by the removal of one hydrogen atom from a single carbon atom of a parent alkane. Alkyl includes branched chain isomers of straight chain alkyl groups such as isopropyl, t-butyl, isobutyl, sec-butyl, and the like. Representative alkyl groups include straight and branched chain alkyl groups having 1, 2, 3, 4, 5, 6, 7, 8, 9, 10, 11 or 12 carbon atoms. Further representative alkyl groups include straight and branched chain alkyl groups having 1, 2, 3, 4, 5, 6, 7 or 8 carbon atoms.

"Alkenyl" refers to a linear monovalent hydrocarbon radical or a branched monovalent hydrocarbon radical having the number of carbon atoms indicated in the prefix and containing at least one double bond, but no more than three double bonds. For example, $C_{2-8}$alkenyl is meant to include, ethenyl, propenyl, 1,3-butadienyl and the like.

"Alkynyl" means a linear monovalent hydrocarbon radical or a branched monovalent hydrocarbon radical containing at least one triple bond and having the number of carbon atoms indicated in the prefix. The term "alkynyl" is also meant to include those alkyl groups having one triple bond and one double bond. For example, $C_{2-8}$alkynyl is meant to include ethynyl, propynyl and the like.

The term "allosteric modulators" refers to compounds that bind to hemoglobin to modulate its affinity for oxygen. In one group of embodiments, the allosteric modulators act to stabilize or destabilize a particular hemoglobin conformation. In one group of embodiments, the modulators stabilize the relaxed R state. In other embodiments, the modulators destabilize the tense T state. In one group of embodiments, the allosteric modulators can destabilize one conformation while stabilizing another. In some such embodiments, the modulators stabilize a relaxed R state and destabilize the tense T state. The modulators, in addition to modulating the affinity of hemoglobin for oxygen, may also confer additional properties to hemoglobin such as increasing its solubility. The present disclosure is not intended to be limited to the mechanism by which the allosteric modulators interact with and regulate hemoglobin. In one group of embodiments, the allosteric modulators inhibit the polymerization of HbS and the sickling of red blood cells. In one group of embodiments, the binding of the allosteric modulators provided herein to hemoglobin can occur through covalent or non-covalent interactions. In one embodiment, the allosteric modulators react through its aldehyde substituent with an amine group on a hemoglobin amino acid side chain to form a Schiff base.

"Amino" refers to a monovalent radical —NH$_2$.

"Aryl" by itself or as part of another substituent refers to a polyunsaturated, aromatic, hydrocarbon group containing from 6 to 14 carbon atoms, which can be a single ring or multiple rings (up to three rings) which are fused together or linked covalently. Thus the phrase includes, but is not limited to, groups such as phenyl, biphenyl, anthracenyl, naphthyl by way of example. Non-limiting examples of aryl groups include phenyl, 1-naphthyl, 2-naphthyl and 4-biphenyl.

"Bond" when used as an element in a Markush group means that the corresponding group does not exist, and the groups of both sides are directly linked.

"Cycloalkyl" refers to a saturated or partially saturated cyclic group of from 3 to 14 carbon atoms and no ring heteroatoms and having a single ring or multiple rings including fused, bridged, and spiro ring systems. The term "cycloalkyl" includes cycloalkenyl groups, a partially saturated cycloalkyl ring having at least one site of >C=C< ring unsaturation. Examples of cycloalkyl groups include, for instance, adamantyl, cyclopropyl, cyclobutyl, cyclopentyl, cyclooctyl, and cyclohexenyl. "$C_{u'-v'}$cycloalkyl" refers to cycloalkyl groups having u' to v' carbon atoms as ring members. "$C_{u'-v'}$cycloalkenyl" refers to cycloalkenyl groups having u' to v' carbon atoms as ring members.

The term "hemoglobin" as used herein refers to any hemoglobin protein, including normal hemoglobin (Hb) and sickle hemoglobin (HbS).

"Heteroaryl" refers to a cyclic or polycyclic radical having at least one aromatic ring and from one to five ring heteroatom selected from N, O, and S, and optionally one or more oxo (=O) substituents attached to one or more carbon ring atoms, and wherein the nitrogen and sulfur ring atoms are optionally oxidized. A heteroaryl group can be attached to the remainder of the molecule through a heteroatom or through a carbon atom and can contain 5 to 10 carbon atoms. Heteroaryl groups include polycyclic aromatic ring(s) fused to non-aromatic cycloalkyl or heterocycloalkyl groups, and where the point of attachment to the remainder of the molecule can be through any suitable ring atom of any ring. In a polycyclic heteroaryl group, the ring heteroatom(s) can be in either an aromatic or non-aromatic ring or both. The term "aromatic ring" include any ring having at least one planar resonance structure where 2n+2 pi electrons are delocalized about the ring. Examples of heteroaryl groups include, but are not limited to, imidazopyridinyl groups, pyrrolopyridinyl groups, pyrazolopyridinyl groups, triazolopyridinyl groups, pyrazolopyrazinyl groups, pyridinyl groups, pyrazinyl groups, oxazolyl groups, imidazolyl groups, triazolyl groups, tetrazolyl groups, pyrazolyl groups, quinolinyl groups, isoquinolinyl groups, indazolyl groups, benzooxazolyl groups, naphthyridinyl groups, and quinoxalinyl groups. Other non-limiting examples of heteroaryl groups include xanthine, hypoxanthine, 5-benzothiazolyl, purinyl, 2-benzimidazolyl, benzopyrazolyl, 5-indolyl, azaindole, 1-isoquinolyl, 5-isoquinolyl, 2-quinoxalinyl, 5-quinoxalinyl, 3-quinolyl, 6-quinolyl 1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl and 4-pyrimidyl. "Bicyclic heteroaryl" refers to a heteroaryl radical that contains two rings.

The term "heterocycloalkyl" refers to a cycloalkyl group containing at least one ring heteroatom and optionally one or more oxo substituents. As used herein, the term "heteroatom" is meant to include oxygen (O), nitrogen (N), and sulfur (S), wherein the heteroatoms are optionally oxidized, and the nitrogen atom(s) are optionally quaternized. Each heterocycle can be attached at any available ring carbon or heteroatom. Each heterocycle may have one or more rings. When multiple rings are present, they can be fused together. Each heterocycle typically contains 1, 2, 3, 4 or 5, independently selected heteroatoms. Preferably, these groups contain 1, 2, 3, 4, 5, 6, 7, 8, 9 or 10 carbon atoms, 0, 1, 2, 3, 4 or 5 nitrogen atoms, 0, 1 or 2 sulfur atoms and 0, 1 or 2 oxygen atoms. More preferably, these groups contain 1, 2 or 3 nitrogen atoms, 0-1 sulfur atoms and 0-1 oxygen atoms. Non-limiting examples of heterocycle groups include morpholin-3-one, piperazine-2-one, piperazin-1-oxide, piperidine, morpholine, piperazine, isoxazoline, pyrazoline, imidazoline, pyrrolidine, and the like.

"Halo" or "halogen" by themselves or as part of another substituent, mean, unless otherwise stated, a fluorine, chlorine, bromine, or iodine atom. Additionally, terms such as "haloalkyl", are meant to include alkyl in which one or more hydrogen is substituted with halogen atoms which can be the same or different, in a number ranging from one up to the maximum number of halogens permitted e.g. for alkyl, (2 m'+1), where m' is the total number of carbon atoms in the alkyl group. For example, the term "haloC1-8alkyl" is meant to include difluoromethyl, trifluoromethyl, 2,2,2-trifluoroethyl, 4-chlorobutyl, 3-bromopropyl, and the like. The term "haloalkenyl", and "haloalkynyl" refers to alkenyl and alkynyl radicals having one or more halogen atoms. Additionally, term "haloalkoxy" refers to an alkoxy radical substituted with one or more halogen atoms. In one group of embodiments, the haloakyl, haloalkenyl, haloalkynyl, and haloalkoxy groups have from one to 5 or from one to 3 halo atoms. Examples of haloalkoxy groups include difluoromethoxy and trifluoromethoxy. In one group of embodiments, the halo atoms of the haloalkenyl and haloalkynyl groups are attached to the aliphatic portions of these groups.

The terms "optional" or "optionally" as used throughout the specification means that the subsequently described event or circumstance may but need not occur, and that the description includes instances where the event or circumstance occurs and instances in which it does not. For example, "heteroaryl group optionally substituted with an alkyl group" means that the alkyl may but need not be present, and the description includes situations where the heteroaryl group is substituted with an alkyl group and situations where the heteroaryl group is not substituted with the alkyl group.

"Oxo" refers to the divalent atom =O.

In each of the above embodiments designating a number of atoms e.g. "$C_{1-8}$" is meant to include all possible embodiments that have one fewer atom. Non-limiting examples include $C_{1-4}$, $C_{1-5}$, $C_{1-6}$, $Cl_{1-7}$, $C_{2-8}$, $C_{2-7}$, $C_{3-8}$, $C_{3-7}$ and the like.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge, S. M. et al., "Pharmaceutical Salts," *Journal of Pharmaceutical Science*, 66:1-19, 1977). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The term "pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

The terms "pharmaceutically effective amount", "therapeutically effective amount" or "therapeutically effective dose" refers to the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disorder or condition and its severity and the age, weight, etc., of the mammal to be treated.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, Protective Groups in Organic Chemistry, $3^{rd}$ Ed., 1999, John Wiley & Sons, NY and Harrison et al., Compendium of Synthetic Organic Methods, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl and trityl ethers, as well as alkyl ethers, tetrahydropyranyl ethers, trialkylsilyl ethers (e.g., TMS or TIPPS groups) and allyl ethers.

The term "aldehyde protecting group" refers to any known protecting group used to mask the aldehyde functionality. Aldehyde protecting groups include acetals and hemiacetals. The acetals and hemiacetals can be prepared from $C_{1-8}$ alcohols or $C_{2-8}$ diols. In one group of embodiments, the aldehyde protecting group is a five or six membered cyclic acetal formed from condensation of the aldehyde with ethylene or propylene glycol. In another group of embodiments the aldehyde protecting group is an imine or hydroxyimine. The aldehyde protecting groups of the present disclosure also include prodrug groups that convert the aldehyde to a prodrug, where the aldehyde is formed in vivo as the active agent under physiological conditions upon administration of the prodrug. The prodrug group can also serve to increase the bioavailability of the aldehyde. In one group of embodiments, the prodrug group is hydrolyzed in vivo to the aldehyde. In one group of embodiments, the aldehyde protecting group is a thiazolidine or N-acetylthiazolidine prodrug group. In one group of embodiments, the aldehyde protecting group is a thiazolidine prodrug group disclosed in U.S. Pat. No. 6,355,661. In one group of embodiments the modulators provided herein are condensed with L-cysteine or a L-cysteine derivative to form the corresponding thiazolidine protected aldehyde prodrug. In one group of embodiments, the thiazolidine has the formula

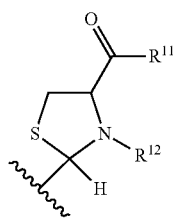

wherein $R^{11}$ is selected from the group consisting of OH, alkoxy, substituted alkoxy, cycloalkoxy, substituted cycloalkoxy, aryloxy, substituted aryloxy, heteroaryloxy, substituted heteroaryloxy, $N(R^{13})_2$ where $R^{13}$ is independently H, alkyl, substituted alkyl, alkenyl, substituted alkenyl, aryl, substituted aryl, heteroaryl, and substituted heteroaryl; $R^{12}$ is H or -L-$R^{14}$, where L is carbonyl or sulfonyl; $R^{14}$ is selected from the group consisting of alkyl, substituted alkyl, aryl, substituted aryl, heteroaryl, and substituted heteroaryl; the wavy line signifies the point of attachment to the phenyl ring of the allosteric modulators disclosed herein; and the term "substituted" refers to substitution by one or more substituents selected from the group consisting of COOH, CHO, oxyacyl, acyloxy, cycloacyloxy, phenol, phenoxy, pyridinyl, pyrrolidinyl, amino, amido, hydroxy, alkoxy, cycloalkoxy, F, Cl, Br, $NO_2$, cyano, sulfuryl, and the like. In one group of embodiments, provided are modulators having a thiazolidine protecting group where $R^{11}$ is alkoxy and $R^{12}$ is H, or where $R^{11}$ is OH and $R^{12}$ is —C(O)alkyl, or where $R^{11}$ is NH(heteroaryl) and $R^{12}$ is —C(O)alkyl.

The term "sickle cell disease" refers to diseases mediated by sickle hemoglobin (HbS) that results from a single point mutation in the hemoglobin (Hb). Sickle cell diseases includes sickle cell anemia, sickle-hemoglobin C disease (HbSC), sickle beta-plus-thalassaemia (HbS/β$^+$) and sickle beta-zero-thalassaemia (HbS/β$^0$).

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

"Tautomer" refers to alternate forms of a molecule that differ in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

The terms "treat", "treating", "treatment" and grammatical variations thereof as used herein, includes partially or completely delaying, alleviating, mitigating or reducing the intensity, progression, or worsening of one or more attendant symptoms of a disorder or condition and/or alleviating, mitigating or impeding one or more causes of a disorder or condition. Treatments according to the invention may be applied preventively, prophylactically, pallatively or remedially.

The symbol > when used in connection with a substituent signifies that the substituent is a divalent substituent attached to two different atoms through a single atom on the substituent.

The term "wavy line" signifies the point of attachment of the substituent to the remainder of the molecule. When the wavy line is not depicted as being specifically appended to a specific ring atom, the point of attachment can be to any suitable atom of the substituent. For example, the wavy line in the following structure:

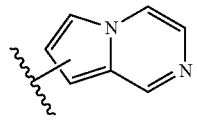

is intended to include, as the point of attachment, any of the six substitutable carbon atoms.

Compounds that have the same molecular formula but differ in the nature or sequence of bonding of their atoms or the arrangement of their atoms in space are termed "isomers". Isomers that differ in the arrangement of their atoms in space are termed "stereoisomers". "Stereoisomer" and "stereoisomers" refer to compounds that exist in different stereoisomeric forms if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Unless otherwise indicated, the description is intended to include individual stereoisomers as well as mixtures. The methods for the determination of stereochemistry and the separation of stereoisomers are well-known in the art (see discussion in Chapter 4 of ADVANCED ORGANIC CHEMISTRY, 4th edition J. March, John Wiley and Sons, New York, 1992) differ in the chirality of one or more stereocenters.

The compounds of the present invention may also contain unnatural proportions of atomic isotopes at one or more of the atoms that constitute such compounds. For example, the compounds may be radiolabeled with isotopes, such as for example deuterium ($^2$H), tritium ($^3$H), iodine-125 ($^{125}$I) or carbon-14 ($^{14}$C). All isotopic variations of the compounds of the present invention, whether radioactive or not, are intended to be encompassed within the scope of the present invention.

Unless indicated otherwise, the nomenclature of substituents that are not explicitly defined herein are arrived at by naming the terminal portion of the functionality followed by the adjacent functionality toward the point of attachment. For example, the substituent "alkoxyalkyl" refers to an alkyl group that is substituted with alkoxy and "hydroxyalkyl" refers to an alkyl group that is substituted with hydroxy. For both of these substituents, the point of attachment is at the alkyl group.

It is understood that the definitions and formulas provided herein are not intended to include impermissible substitution patterns (e.g., methyl substituted with 5 fluoro groups). Such impermissible substitution patterns are well known to the skilled artisan.

II. Hemoglobin Modulators

In one group of embodiments, provided is a compound of Formula (I):

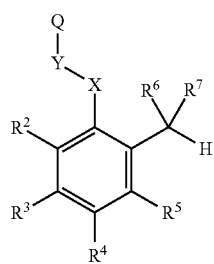

or a tautomer or pharmaceutically acceptable salt thereof, wherein Q is selected from the group consisting of aryl, heteroaryl, and heterocycloalkyl, each optionally substituted with one to three $R^a$;

Y is O or $CR^{1a}R^{1b}$, where $R^{1a}$ is H or halo and $R^{1b}$ is selected from the group consisting of H, halo, and OH;

X is selected from the group consisting of O, >CH$(CH_2)_nR^8$, and $C(R^9)_2$ where n is 0 or 1, $R^8$ is OH, and $R^9$ is independently H or halo; or Y—X taken together is —NHC(O)— or —C(O)NH—;

$R^2$, $R^3$, $R^4$, and $R^5$ are independently selected from the group consisting of hydrogen, halo, $R^b$, $OR^d$, $O(CH_2)_zOR^d$, $O(CH_2)_zNR^dR^d$, $OC(O)R^e$, $SR^d$, CN, $NO_2$, $CO_2R^d$, $CONR^dR^d$, $C(O)R^d$, $OC(O)NR^dR^d$, $NR^dR^d$, $NR^dC(O)R^e$, $NR^dC(O)_2R^e$, $NR^dC(O)NR^dR^d$, $S(O)R^e$, $S(O)_2R^e$, $NR^dS(O)_2R^e$, $S(O)_2NR^dR^d$, and $N_3$, where z is 0, 1, 2, 3, 4, 5, or 6; or $R^5$ is —$(CH_2)_pR^{5a}$ where p is 0 or 1 and $R^{5a}$ is OH;

$R^6$ and $R^7$ together form oxo or an aldehyde protecting group, or $R^6$ together with $R^{1b}$, $R^8$, or $R^5$ forms a cyclic ether where one of $R^{1b}$, $R^8$, or $R^{5a}$ is O, $R^6$ is a bond, and $R^7$ is selected from the group consisting of OH, $C_{1-8}$alkoxy, and halo$C_{1-8}$alkoxy;

each $R^a$ is independently selected from the group consisting of halo, $R^b$, $OR^d$, $O(CH_2)_uOR^d$, $O(CH_2)_uNR^dR^d$, $O(CH_2)_uNR^dC(O)R^e$, $O(CH_2)_uNR^dC(O)_2R^e$, $O(CH_2)_uNR^dS(O)_2R^e$, $NH_2$, —$(CH_2)_kOC(O)R^e$, —$(CH_2)_kSR^d$, CN, $NO_2$, —$(CH_2)_kCO_2(C_{1-8}$alkyl)OH, —$(CH_2)_kCO_2(C_{1-8}$alkyl)(heteroaryl)C(O)($C_{1-8}$alkyl), —$(CH_2)_kCO_2R^d$, —$(CH_2)_kCONR^dR^d$, —$(CH_2)_kNR^dC(O)R^e$, —$(CH_2)_kNR^dC(O)_2R^e$, —$(CH_2)_kC(O)R^d$, —$(CH_2)_kOC(O)NR^dR^d$, —$NR^d(CH_2)_uOR^d$, —$NR^d(CH_2)_uNR^dR^d$, —$NR^d(CH_2)_uNR^dC(O)R^e$, —$NR^d(CH_2)_uNR^dC(O)_2R^e$, —$NR^d(CH_2)_uNR^dS(O)_2R^e$, —$(CH_2)_kNR^dC(O)R^e$, —$(CH_2)_kNR^dC(O)_2R^d$, —$(CH_2)_kNR^dC(O)NR^dR^d$, —$(CH_2)_kS(O)R^e$, —$(CH_2)_kS(O)_2R^e$, —$(CH_2)_kNR^dS(O)_2R^e$, —$(CH_2)_kS(O)_2NR^dR^d$, $N_3$, —$(CH_2)_k$aryl optionally substituted with one to three $R^c$, —$NR^d(CH_2)_k$aryl optionally substituted with one to three $R^c$, —$(CH_2)_k$heteroaryl optionally substituted with one to three $R^c$, —$NR^d(CH_2)_k$heteroaryl optionally substituted with one to three $R^c$, —$(CH_2)_k$heterocycloalkyl optionally substituted with one to three $R^c$, and —$NR^d(CH_2)_k$heterocycloalkyl optionally substituted with one to three $R^c$ where k is 0, 1, 2, 3, 4, 5, or 6 and u is 1, 2, 3, 4, 5, or 6;

each $R^b$ is independently selected from the group consisting of $C_{1-8}$alkyl, $C_{2-8}$alkenyl, and $C_{2-8}$alkynyl, each optionally independently substituted with one to three halo, $OR^d$, or $NR^dR^d$;

each $R^c$ is independently selected from the group consisting of halo, $C_{1-8}$alkyl, halo$C_{1-8}$alkyl, $C_{2-8}$alkenyl, halo$C_{2-8}$alkenyl, $C_{2-8}$alkynyl, halo$C_{2-8}$alkynyl, $(CH_2)_mOR^f$, $OC(O)R^g$, $SR^f$, CN, $NO_2$, $CO_2R^f$, $CONR^fR^f$, $C(O)R^f$, $OC(O)NR^fR^f$, $(CH_2)_mNR^fR^f$, $NR^fC(O)R^g$, $NR^fC(O)_2R^g$, $NR^fC(O)NR^fR^f$, $S(O)R^g$, $S(O)_2R^g$, $NR^fS(O)_2R^g$, $S(O)_2NR^fR^f$, $N_3$, heteroaryl optionally substituted with one to three $R^h$, and heterocycloalkyl optionally substituted with one to three $R^h$ where m is selected from the group consisting of 0, 1, 2, 3, 4, 5, and 6;

each $R^h$ is independently selected from the group consisting of halo, $C_{1-8}$alkyl, halo$C_{1-8}$alkyl, $OR^j$, $OC(O)R$, $SR^j$, $NO_2$, $CO_2R^j$, $CONR^jR^j$, $C(O)R^j$, $OC(O)NR^jR^j$, $NR^jR^j$, $NR^jC(O)R^t$, $NR^jC(O)_2R^t$, $NR^jC(O)NR^jR^j$, $S(O)R^t$, $S(O)_2R^t$, $NR^jS(O)_2R^t$, and $S(O)_2NR^jR^j$;

$R^d$, $R^f$, and $R^j$ are each is independently selected from the group consisting of hydrogen, $C_{1-8}$ alkyl, halo$C_{1-8}$alkyl, $C_{2-8}$alkenyl, halo$C_{2-8}$alkenyl, $C_{2-8}$ alkynyl, and halo$C_{2-8}$ alkynyl; and $R^e$, $R^g$, and $R^t$ are each is independently selected from the group consisting of $C_{1-8}$alkyl, halo$C_{1-8}$alkyl, $C_{2-8}$ alkenyl, halo$C_{2-8}$alkenyl, $C_{2-8}$ alkynyl, and halo$C_{2-8}$alkynyl.

In one group of embodiments, X and Y are not both O.

In one group of embodiments, when X is O, $R^{1b}$ is not OH.

In one group of embodiments, when Y is O, and n is O, $R^8$ is not OH.

In one group of embodiments, when $R^6$ and $R^7$ together are oxo, Y is $CH_2$, X is O or $CH_2$, and $R^5$ is H, halo, OH, CHO, or $OCH_3$, then Q is V or W.

In one group of embodiments, V is selected from the group consisting of

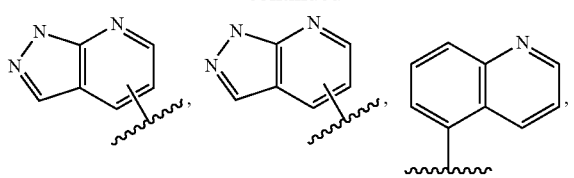
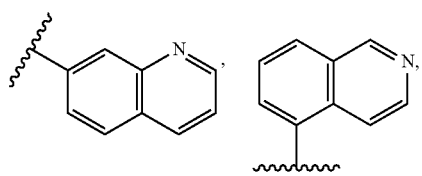
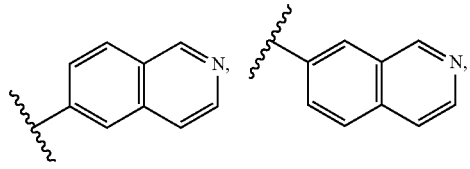
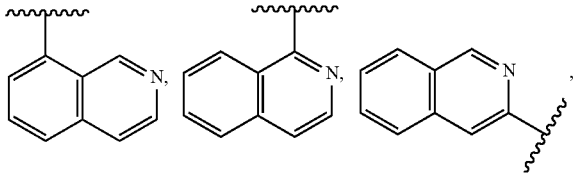
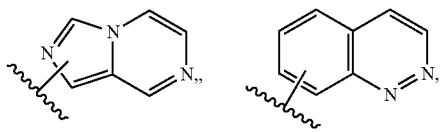
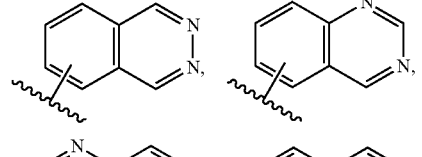
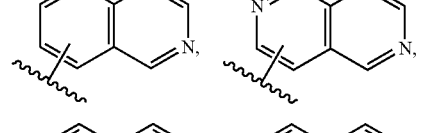
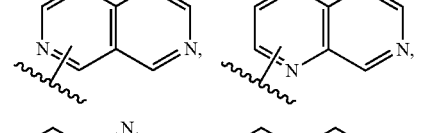
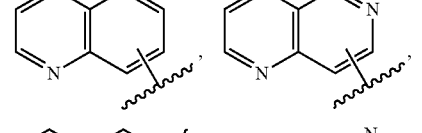
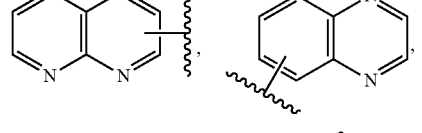
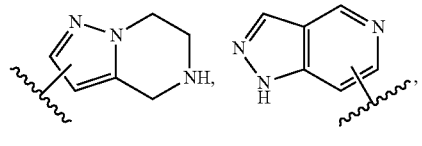

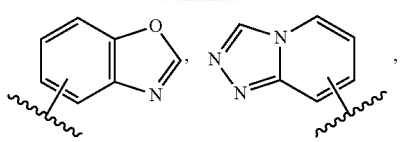
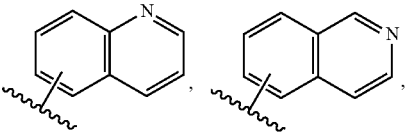
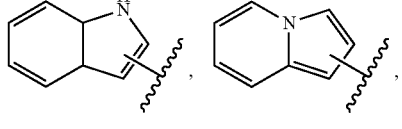

and naphthalene containing three to four ring nitrogen atoms; wherein V is optionally substituted with one to three $R^a$; and W is selected from the group consisting of pyridin-2-yl, pyridin-3-yl, and pyridine-4-yl,

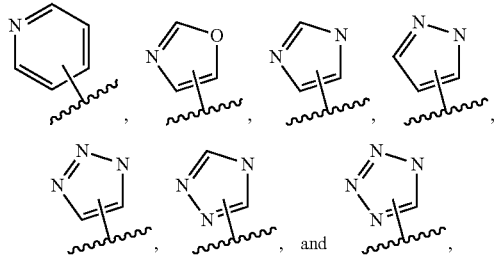

wherein W is optionally substituted with one to three $R^a$ or is substituted with one to three $R^a$ when W is pyridin-2-yl, pyridin-3-yl, or pyridine-4-yl, and wherein the wavy line signifies the point of attachment to Y, provided that when V is

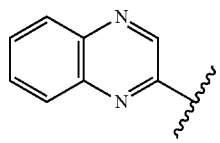 [SMILES: *c1cnc2ccccc2n1]

optionally substituted with one $R^a$, then at least one of $R^2$, $R^3$, $R^4$, and $R^5$ is $OR^d$; and provided that when V is

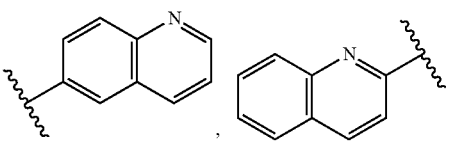

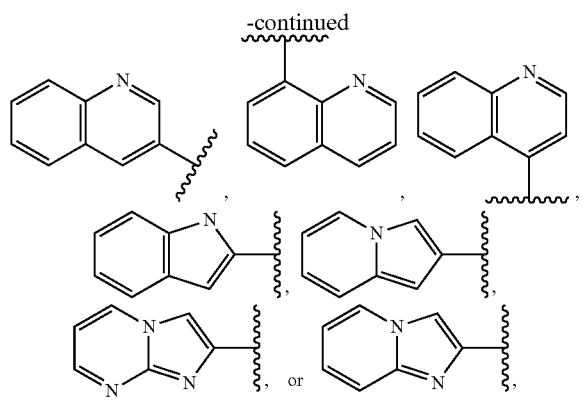

then V is substituted with one to three $R^a$.

In one group of embodiments, z is 0. In another group of embodiments, z is 1. In yet another group of embodiments, z is 2. In still another group of embodiments, z is 3. In another group of embodiments, z is 4. In yet another group of embodiments, z is 5. In still another group of embodiments, z is 6.

In one group of embodiments, provided is a compound of Formula (Ia):

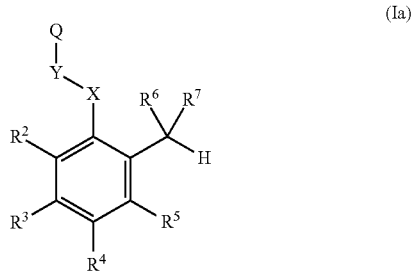

(Ia)

or a tautomer or pharmaceutically acceptable salt thereof, wherein Q is selected from the group consisting of aryl, heteroaryl, and heterocycloalkyl, each optionally substituted with one to three $R^a$;

Y is O or $CR^{1a}R^{1b}$, where $R^{1a}$ is H or halo and $R^{1b}$ is selected from the group consisting of H, halo, and OH;

X is selected from the group consisting of O, >CH $(CH_2)_nR^8$, and $C(R^9)_2$ where n is 0 or 1, $R^8$ is OH, and $R^9$ is independently H or halo;

$R^2$, $R^3$, $R^4$, and $R^5$ are independently selected from the group consisting of hydrogen, halo, $R^b$, $OR^d$, $OC(O)R^e$, $SR^d$, CN, $NO_2$, $CO_2R^d$, $CONR^dR^d$, $C(O)R^d$, $OC(O)NR^dR^d$, $NR^dR^d$, $NR^dC(O)R^e$, $NR^dC(O)_2R^e$, $NR^dC(O)NR^dR^d$, $S(O)R^e$, $S(O)_2R^e$, $NR^dS(O)_2R^e$, $S(O)_2NR^dR^d$, and $N_3$; or $R^5$ is —$(CH_2)_pR^{5a}$ where p is 0 or 1 and $R^{5a}$ is OH;

$R^6$ and $R^7$ together form oxo or an aldehyde protecting group, or $R^6$ together with $R^{1b}$, $R^8$, or $R^5$ forms a cyclic ether where one of $R^{1b}$, $R^8$, or $R^{5a}$ is —O—, $R^6$ is a bond, and $R^7$ is selected from the group consisting of OH, $C_{1-8}$alkoxy, and halo$C_{1-8}$alkoxy;

each $R^a$ is independently selected from the group consisting of halo, $R^b$, $OR^d$, $OC(O)R^e$, $SR^d$, CN, $NO_2$, $CO_2R^d$, $CONR^dR^d$, $C(O)R^d$, $OC(O)NR^dR^d$, $NR^dC(O)R^e$, $NR^d C(O)_2R^d$, $NR^dC(O)NR^dR^d$, $S(O)R^e$, $S(O)_2R^e$, $NR^dS(O)_2R^e$, $S(O)_2NR^dR^d$, $N_3$, aryl optionally substituted with one to three $R^c$, heteroaryl optionally substituted with one to three $R^c$, and heterocycloalkyl optionally substituted with one to three $R^c$;

each $R^b$ is independently selected from the group consisting of $C_{1-8}$alkyl, $C_{2-8}$alkenyl, and $C_{2-8}$ alkynyl, each optionally independently substituted with one to three halo, $OR^d$, or $NR^dR^d$;

each $R^c$ is independently selected from the group consisting of halo, $C_{1-8}$alkyl, halo $C_{1-8}$alkyl, $C_{2-8}$alkenyl, halo$C_{2-8}$alkenyl, $C_{2-8}$ alkynyl, halo$C_{2-8}$alkynyl, $(CH_2)_mOR^f$, $OC(O)R^g$, $SR^f$, CN, $NO_2$, $CO_2R^f$, $CONR^fR^f$, $C(O)R^f$, $OC(O)NR^fR^f$, $(CH_2)_mNR^fR^f$, $NR^fC(O)R^g$, $NR^fC(O)_2R^g$, $NR^fC(O)NR^fR^f$, $S(O)R^g$, $S(O)_2R^g$, $NR^fS(O)_2R^g$, $S(O)_2NR^fR^f$, and $N_3$ where m is selected from the group consisting of 0, 1, 2, 3, 4, 5, and 6;

each $R^d$ and $R^f$ is independently selected from the group consisting of hydrogen, $C_{1-8}$ alkyl, halo$C_{1-8}$alkyl, $C_{2-8}$ alkenyl, halo$C_{2-8}$alkenyl, $C_{2-8}$ alkynyl, and halo$C_{2-8}$alkynyl; and each $R^e$ and $R^g$ is independently selected from the group consisting of $C_{1-8}$alkyl, halo$C_{1-8}$alkyl, $C_{2-8}$ alkenyl, halo $C_{2-8}$alkenyl, $C_{2-8}$ alkynyl, and halo$C_{2-8}$alkynyl;

provided that X and Y are not both O;
provided that when X is O, $R^{1b}$ is not OH;
provided that when Y is O, and n is 0, $R^8$ is not OH; and
provided that when $R^6$ and $R^7$ together are oxo, Y is $CH_2$, X is O or $CH_2$, and $R^5$ is H, halo, OH, CHO, or $OCH_3$, then Q is V or W;

V is selected from the group consisting of

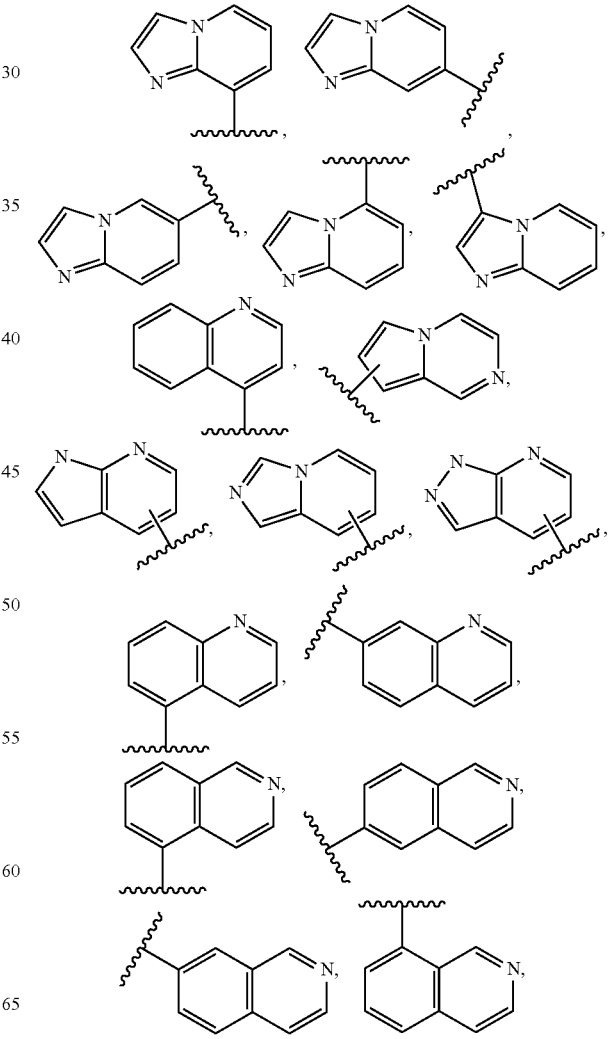

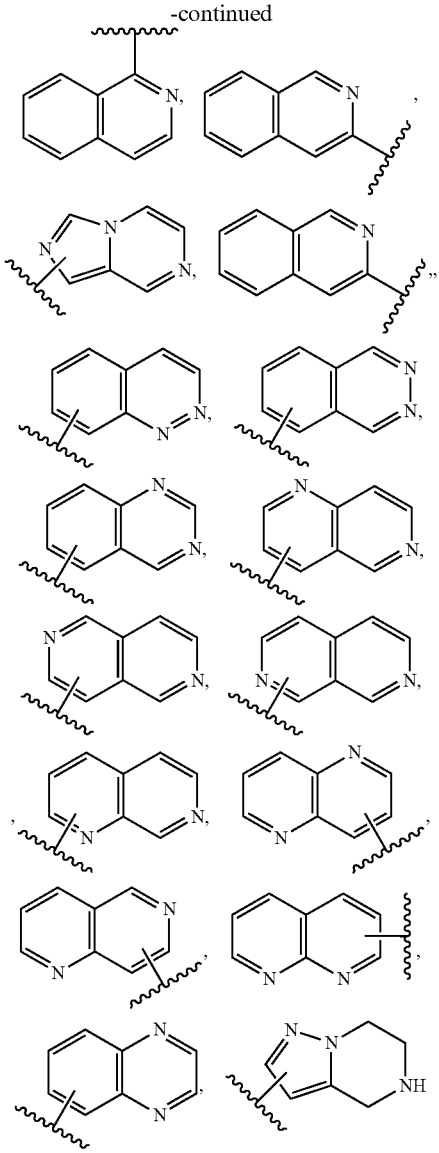

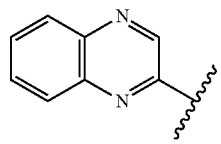 [SMILES: *c1cnc2ccccc2n1]

optionally substituted with one $R^a$, then at least one of $R^2$, $R^3$, $R^4$, and $R^5$ is $OR^d$.

In one group of embodiments when $R^6$ and $R^7$ together are oxo, Y is $CH_2$, X is O or $CH_2$, and $R^5$ is H, halo, OH, CHO, or $OCH_3$, Q is not

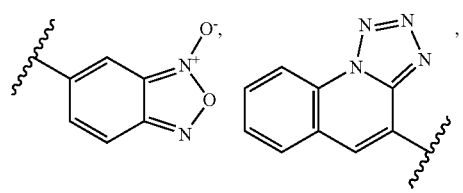

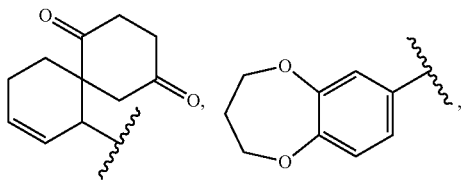

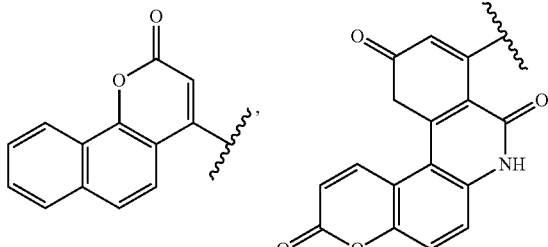

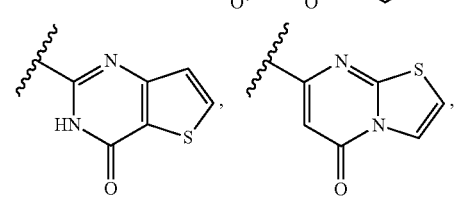

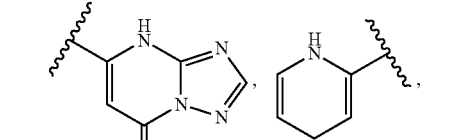

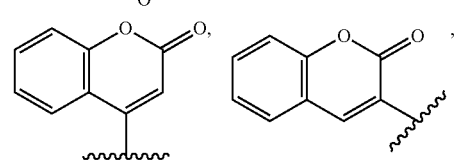

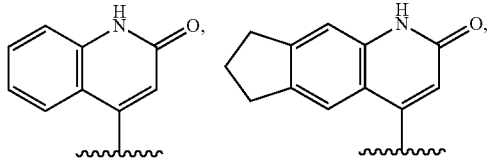

and naphthalene containing three to four ring nitrogen atoms; wherein V is optionally substituted with one to three $R^a$; and W is selected from the group consisting of pyridin-2-yl, pyridin-3-yl, and pyridine-4-yl,

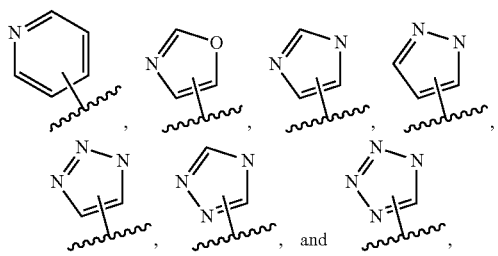

wherein W is optionally substituted with one to three $R^a$ or is substituted with one to three $R^a$ when W is pyridin-2-yl, pyridin-3-yl, or pyridine-4-yl, and wherein the wavy line signifies the point of attachment to Y, provided that when V is

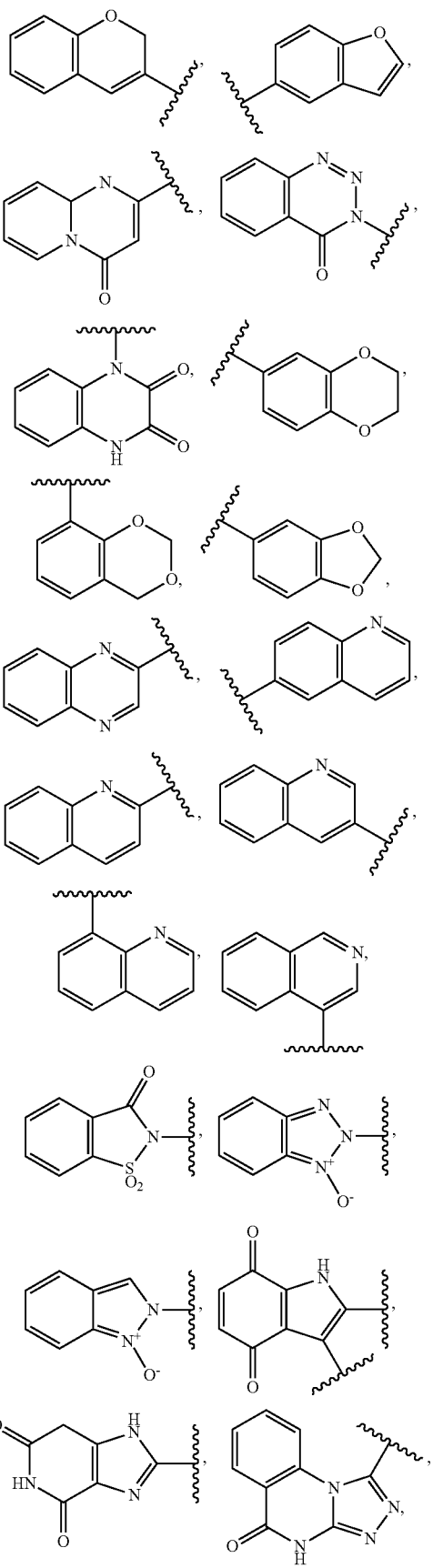
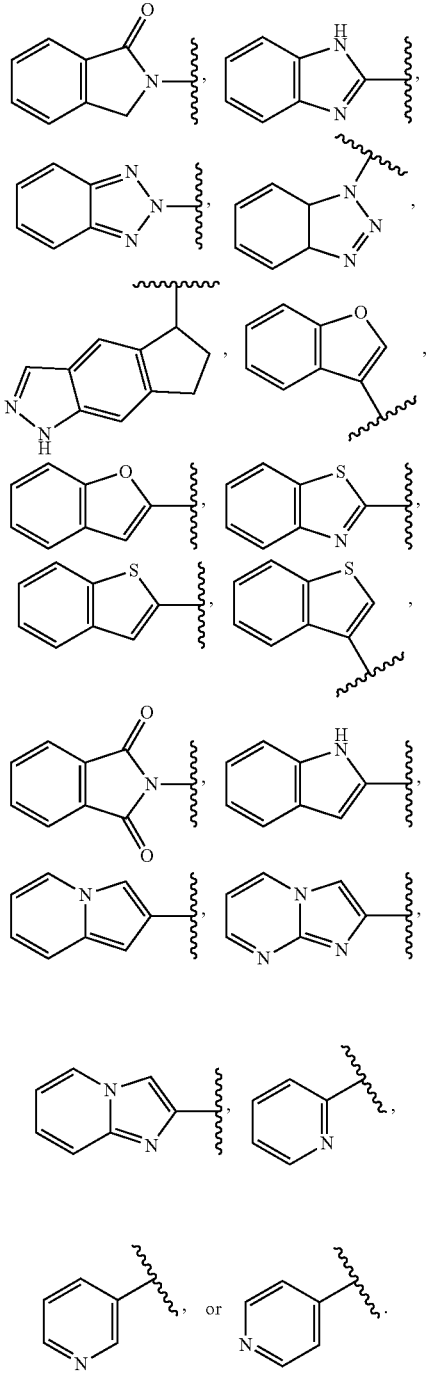

In one group of embodiments, $R^6$ and $R^7$ together form oxo.

In one group of embodiments, $R^6$ and $R^7$ together form a thiazolidine.

In one group of embodiments, z is 0. In another group of embodiments, z is 1. In yet another group of embodiments, z is 2. In still another group of embodiments, z is 3. In another group of embodiments, z is 4. In yet another group of embodiments, z is 5. In still another group of embodiments, z is 6.

In one group of embodiments, provided is a compound having Formula (Ic), (Id), or (Ie):

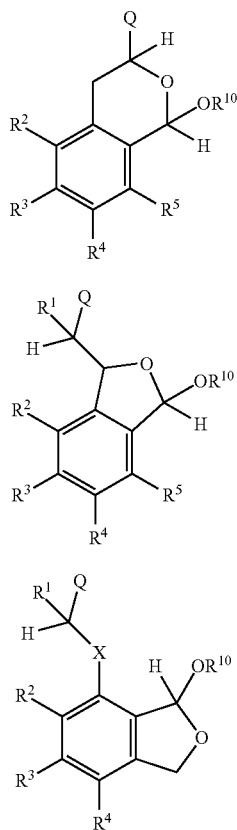

(Ic)

(Id)

(Ie)

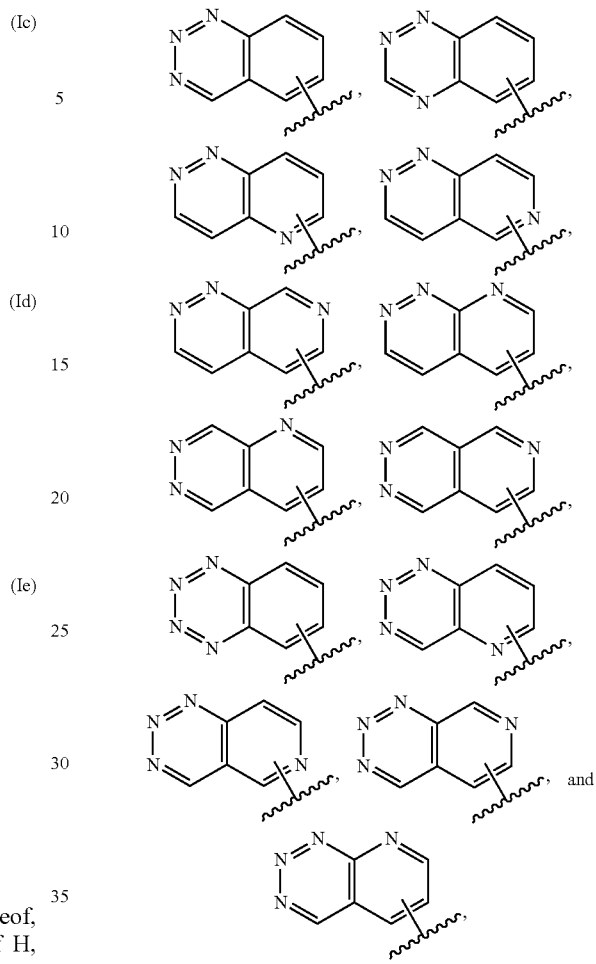

or a tautomer or pharmaceutically acceptable salt thereof, wherein $R^{10}$ is selected from the group consisting of H, $C_{1-8}$alkyl, and halo$C_{1-8}$alkyl.

In one group of embodiments, Q is a heteroaryl or heterocycloalkyl group optionally substituted with one to three $R^a$.

In one group of embodiments, Q is a bicyclic heteroaryl or heterocycloalkyl group optionally substituted with one to three $R^a$.

In one group of embodiments, Q is a bicyclic heteroaryl group optionally substituted with one to three $R^a$. In one group of embodiments, Q is isoquinolin-4-yl optionally substituted with one to three $R^a$ wherein at least one $R^a$ is heteroaryl optionally substituted with one to three $R^c$. In one group of embodiments at least one $R^a$ is heteroaryl attached to said Q at the ring atom adjacent to ring atom bearing Y. In one group of embodiments at least one $R^a$ is heteroaryl substituted with at least one $C_{1-8}$alkyl. In one group of embodiments at least one $R^a$ heteroaryl is substituted with at least one methyl. In one group of embodiments at least one $R^a$ is pyrazolyl substituted with at least one $C_{1-8}$alkyl. In one group of embodiments at least one $R^a$ is pyrazoyl substituted with at least one methyl. In one group of embodiments, $R^a$ is pyrazol-5-yl. In one group of embodiments, $R^a$ is 4-methyl-pyrazol-5-yl.

In one group of embodiments, Q is a bicyclic heteroaryl group substituted with one to three $R^a$.

In one group of embodiments, Q is V.

In one group of embodiments, V is selected from the group consisting of wherein V is optionally substituted with one to three $R^a$.

In one group of embodiments, Q is substituted with CON-$R^dR^d$, $NR^dR^d$, or heteroaryl optionally substituted with one to three $R^c$. In one group of embodiments, Q is substituted with heteroaryl having one to two nitrogen ring atoms.

In one group of embodiments, Q is W.

In one group of embodiments, Q is selected from the group consisting of

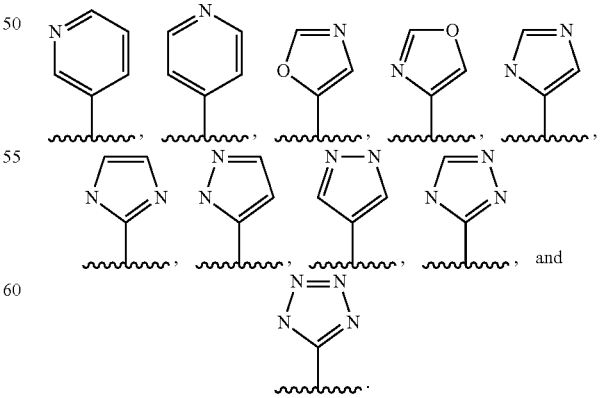

In one group embodiments, at least one $R^a$ is heteroaryl optionally substituted with one to three $R^c$.

In one group of embodiments at least one $R^a$ is heteroaryl attached to Q at the ring atom adjacent to ring atom bearing Y.

In one group of embodiments at least one $R^a$ is heteroaryl substituted with at least one $C_{1-8}$alkyl. In one group of embodiments at least one $R^a$ heteroaryl is substituted with at least one methyl.

In one group of embodiments at least one $R^a$ is pyrazolyl substituted with at least one $C_{1-8}$alkyl. In one group of embodiments at least one $R^a$ is pyrazoyl substituted with at least one $C_{1-8}$alkyl. In one group of embodiments, at least one $R^a$ is pyrazol-5-yl. In one group of embodiments, at least one $R^a$ is 4-methyl-pyrazol-5-yl.

In one group of embodiments, Q is pyridin-2-yl, pyridin-3-yl, or pyridine-4-yl, said Q is optionally substituted with one to three $R^a$ wherein at least one $R^a$ is heteroaryl optionally substituted with one to three $R^c$. In one group of embodiments at least one $R^a$ is heteroaryl attached to said Q at the ring atom adjacent to ring atom bearing Y. In one group of embodiments at least one $R^a$ is heteroaryl substituted with at least one $C_{1-8}$alkyl. In one group of embodiments at least one $R^a$ heteroaryl is substituted with at least one methyl. In one group of embodiments at least one $R^a$ is pyrazolyl substituted with at least one $C_{1-8}$alkyl. In one group of embodiments at least one $R^a$ is pyrazoyl substituted with at least one methyl. In one group of embodiments, $R^a$ is pyrazol-5-yl. In one group of embodiments, $R^a$ is 4-methyl-pyrazol-5-yl.

In one group of embodiments, Q is substituted with at least one $R^a$ selected from the group consisting of —$(CH_2)_kOH$, —$(CH_2)_kNH_2$, —$(CH_2)_kNH(C_{1-8}alkyl)$, —$(CH_2)_kN(C_{1-8}alkyl)(C_{1-8}alkyl)$, —$(CH_2)_kNHC(O)(C_{1-8}alkyl)$, —$(CH_2)_kN(C_{1-8}alkyl)C(O)(C_{1-8}alkyl)$, —$(CH_2)_kNHC(O)_2(C_{1-8}alkyl)$, —$(CH_2)_kN(C_{1-8}alkyl)C(O)_2(C_{1-8}alkyl)$, —$(CH_2)_kNHS(O)_2(C_{1-8}alkyl)$, —$(CH_2)_kN(C_{1-8}alkyl)S(O)_2(C_{1-8}alkyl)$, and —$(CH_2)_k$heterocycloalkyl optionally substituted with one to three $R^c$. In some embodiments the heterocycloalkyl group is morpholino or piperazinyl optionally substituted with alkyl, —$C(O)C_{1-8}$alkyl, —$C(O)_2C_{1-8}$alkyl, or —$S(O)_2C_{1-8}$alkyl.

In one group of embodiments, Q is substituted with at least one $R^a$ selected from the group consisting of —$NR^d(CH_2)_uOH$, —$NR^d(CH_2)_uNH_2$, —$NR^d(CH_2)_uNH(C_{1-8}alkyl)$, —$NR^d(CH_2)_uN(C_{1-8}alkyl)(C_{1-8}alkyl)$, —$NR^d(CH_2)_uNHC(O)(C_{1-8}alkyl)$, —$NR^d(CH_2)_uN(C_{1-8}alkyl)C(O)(C_{1-8}alkyl)$, —$NR^d(CH_2)_uNHC(O)_2(C_{1-8}alkyl)$, —$NR^d(CH_2)_uN(C_{1-8}alkyl)C(O)_2(C_{1-8}alkyl)$, —$NR^d(CH_2)_uNHS(O)_2(C_{1-8}alkyl)$, —$NR^d(CH_2)_uN(C_{1-8}alkyl)S(O)_2(C_{1-8}alkyl)$, and —$NR^d(CH_2)_k$heterocycloalkyl optionally substituted with one to three $R^c$ where u is 1, 2, 3, 4, 5, or 6 and k is 0, 1, 2, 3, 4, 5, or 6. In some embodiments, $R^d$ is H or $C_{1-8}$alkyl. In some embodiments the heterocycloalkyl group is morpholino or piperazinyl optionally substituted with alkyl, —$C(O)C_{1-8}$alkyl, —$C(O)_2C_{1-8}$alkyl, or —$S(O)_2C_{1-8}$alkyl.

In one group of embodiments, Q is substituted with at least one $R^a$ selected from the group consisting of $O(CH_2)_uOH$, $O(CH_2)_uNH_2$, $O(CH_2)_uNH(C_{1-8}alkyl)$, $O(CH_2)_uN(C_{1-8}alkyl)(C_{1-8}alkyl)$, $O(CH_2)_uNHC(O)(C_{1-8}alkyl)$, $O(CH_2)_uN(C_{1-8}alkyl)C(O)(C_{1-8}alkyl)$, $O(CH_2)_uNHC(O)_2(C_{1-8}alkyl)$, $O(CH_2)_uN(C_{1-8}alkyl)C(O)_2(C_{1-8}alkyl)$, $O(CH_2)_uNHS(O)_2(C_{1-8}alkyl)$, $O(CH_2)_uN(C_{1-8}alkyl)S(O)_2(C_{1-8}alkyl)$, and $O(CH_2)_u$heterocycloalkyl optionally substituted with one to three $R^c$ where u is 1, 2, 3, 4, 5, or 6. In some embodiments the heterocycloalkyl group is morpholino or piperazinyl optionally substituted with alkyl, —$C(O)C_{1-8}$alkyl, —$C(O)_2C_{1-8}$alkyl, or —$S(O)_2C_{1-8}$alkyl.

In one group of embodiments, W is pyridin-2-yl, pyridin-3-yl, or pyridine-4-yl, said W substituted with CN or CON-$R^dR^d$.

In one group of embodiments, $R^2$ is H.
In one group of embodiments, $R^3$ is H.
In one group of embodiments, $R^5$ is H.
In one group of embodiments, $R^4$ is $C_{1-8}$alkoxy.
In one group of embodiments, $R^2$, $R^3$, $R^5$ are H and $R^4$ is $C_{1-8}$alkoxy.
In one group of embodiments, $R^4$ is methoxy.
In one group of embodiments, $R^4$ is haloalkoxy. In one group of embodiments, $R^4$ is $OCHF_2$. In one group of embodiments, $R^4$ is $OCF_3$.
In one group of embodiments, $R^2$, $R^3$, $R^4$, and $R^5$ are H.
In one group of embodiments, one of $R^2$, $R^3$, $R^4$, and $R^5$ is selected from the group consisting of —$O(CH_2)_zOH$, —$O(CH_2)_zO(C_{1-8}alkyl)$, —$O(CH_2)_zNH_2$, —$O(CH_2)_zNH(C_{1-8}alkyl)$, and —$O(CH_2)_zN(C_{1-8}alkyl)(C_{1-8}alkyl)$ where z is 0, 1, 2, 3, 4, 5, or 6.
In one group of embodiments, X is O.
In one group of embodiments, X is $CH_2$.
In one group of embodiments, X is $C(R^9)_2$ and at least one of $R^9$ is F.
In one group of embodiments, Y is $CH_2$.
In one group of embodiments, Y is $CR^{1a}R^{1b}$ and at least one of $R^{1a}$ or $R^{1b}$ is F.
In one group of embodiments, z is 0. In another group of embodiments, z is 1. In yet another group of embodiments, z is 2. In still another group of embodiments, z is 3. In another group of embodiments, z is 4. In yet another group of embodiments, z is 5. In still another group of embodiments, z is 6.

In other embodiments, the invention provide a compound according to Formula (Ib):

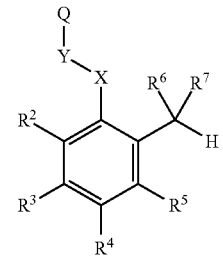

(Ib)

or a tautomer or pharmaceutically acceptable salt thereof, wherein Q is selected from the group consisting of aryl, heteroaryl, and heterocycloalkyl, each optionally substituted with one to three $R^a$;

Y is O or $CH_2$;

X is O or $CH_2$;

$R^2$ and $R^3$ are independently selected from the group consisting of hydrogen, halo, $R^b$, $OR^d$, —$O(CH_2)_zOR^d$, —$O(CH_2)_zNR^dR^d$, $OC(O)R^e$, $SR^d$, CN, $NO_2$, $CO_2R^d$, $CONR^dR^d$, $C(O)R^d$, $OC(O)NR^dR^d$, $NR^dR^d$, $NR^dC(O)R^e$, $NR^dC(O)_2R^e$, $NR^dC(O)NR^dR^d$, $S(O)R^e$, $S(O)_2R^e$, $NR^dS(O)_2R^e$, $S(O)_2NR^dR^d$, and $N_3$, where z is 0, 1, 2, 3, 4, 5, or 6; or $R^5$ is —$(CH_2)_pR^{5a}$ where p is 0 or 1 and $R^{5a}$ is OH;

$R^4$ is selected from the group consisting of hydrogen and $OR^d$;

$R^5$ is selected from the group consisting of hydrogen, halo, and $OR^d$;

$R^6$ and $R^7$ together form oxo or an aldehyde protecting group;

each $R^a$ is independently selected from the group consisting of halo, $R^b$, $OR^d$, $O(CH_2)_uOR^d$, $O(CH_2)_uNR^dR^d$, $O(CH_2)_uNR^dC(O)R^e$, $O(CH_2)_uNR^dC(O)_2R^e$, $O(CH_2)_uNR^dS(O)_2R^e$, $NH_2$, —$(CH_2)_kOC(O)R^e$, —$(CH_2)_kSR^d$, CN, $NO_2$, —(CH$_2$)$_k$CO$_2$(C$_{1-8}$alkyl)OH, —(CH$_2$)$_k$CO$_2$(C$_{1-8}$alkyl)(heteroaryl)C(O)(C$_{1-8}$alkyl), —(CH$_2$)$_k$CO$_2$R$^d$, —(CH$_2$)$_k$CONR$^d$R$^d$, —(CH$_2$)$_k$NR$^d$C(O)R$^e$, —(CH$_2$)$_k$NR$^d$C(O)$_2$R$^e$, —(CH$_2$)$_k$C(O)R$^d$, —(CH$_2$)$_k$OC(O)NR$^d$R$^d$, —NR$^d$(CH$_2$)$_u$OR$^d$, —NR$^d$(CH$_2$)$_u$NR$^d$R$^d$, —NR$^d$(CH$_2$)$_u$NR$^d$C(O)R$^e$, —NR$^d$(CH$_2$)$_u$NR$^d$C(O)$_2$R$^e$, —NR$^d$(CH$_2$)$_u$NR$^d$S(O)$_2$R$^e$, —(CH$_2$)$_k$NR$^d$C(O)R$^e$, —(CH$_2$)$_k$NR$^d$C(O)$_2$R$^d$, —(CH$_2$)$_k$NR$^d$C(O)NR$^d$R$^d$, —(CH$_2$)$_k$S(O)R$^e$, —(CH$_2$)$_k$S(O)$_2$R$^e$, —(CH$_2$)$_k$NR$^d$S(O)$_2$R$^e$, —C(O)(CH$_2$)$_k$NR$^d$S(O)$_2$R$^e$, —(CH$_2$)$_k$C(O)NR$^d$S(O)$_2$R$^e$, —(CH$_2$)$_k$S(O)$_2$NR$^d$R$^d$, N$_3$, —(CH$_2$)$_k$aryl optionally substituted with one to three R$^c$, —NR$^d$(CH$_2$)$_k$aryl optionally substituted with one to three R$^c$, —(CH$_2$)$_k$heteroaryl optionally substituted with one to three R$^c$, —NR$^d$(CH$_2$)$_k$heteroaryl optionally substituted with one to three R$^c$, —(CH$_2$)$_k$heterocycloalkyl optionally substituted with one to three R$^c$, and —NR$^d$(CH$_2$)$_k$heterocycloalkyl optionally substituted with one to three R$^c$ where k is 0, 1, 2, 3, 4, 5, or 6 and u is 1, 2, 3, 4, 5, or 6;

each R$^b$ is independently selected from the group consisting of C$_{1-8}$alkyl, C$_{2-8}$alkenyl, and C$_{2-8}$alkynyl, each optionally independently substituted with one to three halo, OR$^d$, or NR$^d$R$^d$;

each R$^c$ is independently selected from the group consisting of halo, C$_{1-8}$alkyl, haloC$_{1-8}$alkyl, C$_{2-8}$alkenyl, halo C$_{2-8}$alkenyl, C$_{2-8}$alkynyl, haloC$_{2-8}$alkynyl, (CH$_2$)$_m$OR$^f$, OC(O)R$^g$, SR$^f$, CN, NO$_2$, (CH$_2$)$_m$CO$_2$R$^f$, CONR$^f$R$^f$, C(O)R$^f$, OC(O)NR$^f$R$^f$, (CH$_2$)$_m$NR$^f$R$^f$, NR$^f$C(O)R$^g$, NR$^f$C(O)$_2$R$^g$, NR$^f$C(O)NR$^f$R$^f$, S(O)R$^g$, S(O)$_2$R$^g$, NR$^f$S(O)$_2$R$^g$, S(O)$_2$NR$^f$R$^f$, N$_3$, (R$^f$)$_m$SiC$_{1-8}$alkyl, heteroaryl optionally substituted with one to three R$^h$, cycloalkyl optionally substituted with one to three R$^h$, and heterocycloalkyl optionally substituted with one to three R$^h$ where m is selected from the group consisting of 0, 1, 2, 3, 4, 5, and 6;

each R$^h$ is independently selected from the group consisting of halo, C$_{1-8}$alkyl, haloC$_{1-8}$alkyl, OR$^j$, OC(O)R, SR$^j$, NO$_2$, CO$_2$R$^j$, CONR$^j$R$^j$, C(O)R$^j$, OC(O)NR$^j$R$^j$, NR$^j$R$^j$, NR$^j$C(O)R$^t$, NR$^j$C(O)$_2$R$^t$, NR$^j$C(O)NR$^j$R$^j$, S(O)R$^t$, S(O)$_2$R$^t$, NR$^j$S(O)$_2$R$^t$, and S(O)$_2$NR$^j$R$^j$;

R$^d$, R$^f$, and R$^j$ are each independently selected from the group consisting of hydrogen, C$_{1-8}$ alkyl, haloC$_{1-8}$alkyl, C$_{2-8}$ alkenyl, haloC$_{2-8}$alkenyl, C$_{2-8}$ alkynyl, and haloC$_{2-8}$alkynyl; and R$^e$, R$^g$, and R$^t$ are each independently selected from the group consisting of C$_{1-8}$alkyl, haloC$_{1-8}$alkyl, C$_{2-8}$ alkenyl, haloC$_{2-8}$alkenyl, C$_{2-8}$ alkynyl, and haloC$_{2-8}$alkynyl;

provided that X and Y are not both O;
provided that at least one of R$^4$ and R$^5$ is H;
provided that if R$^4$ is OR$^d$, then Q is not phenyl, pyridinyl, or imidazo[1,2-a]pyridin-2-yl, R$^a$ is not oxo, oxido, or halo, and X is O,
provided that if R$^5$ is OR$^d$, then R$^a$ is not oxo, oxido, or halo; and
provided that if R$^2$-R$^5$ are H, then Q is not phenyl.

In one group of embodiments, the invention provides a compound of formula Ib, or a tautomer or pharmaceutically acceptable salt thereof, wherein R$^6$ and R$^7$ together form oxo.

In one group of embodiments, the invention provides a compound of formula Ib, or a tautomer or pharmaceutically acceptable salt thereof, wherein R$^5$ is selected from the group consisting of hydrogen and OR$^d$.

In one group of embodiments, the invention provides a compound of formula Ib, or a tautomer or pharmaceutically acceptable salt thereof, wherein R$^5$ is selected from the group consisting of hydroxy and fluoro.

In one group of embodiments, the invention provides a compound of formula Ib, wherein R$^2$ and R$^3$ are independently selected from the group consisting of hydrogen, R$^b$, OR$^d$, O(CH$_2$)$_z$OR$^d$, O(CH$_2$)$_z$NR$^d$R$^d$, OC(O)R$^e$, CO$_2$R$^d$, CONR$^d$R$^d$, and C(O)R$^d$, where z is 1, 2, or 3.

In one group of embodiments, the invention provides a compound of formula Ib, wherein R$^2$ and R$^3$ are H.

In one group of embodiments, the invention provides a compound of formula Ib, wherein Q is selected from the group consisting of:

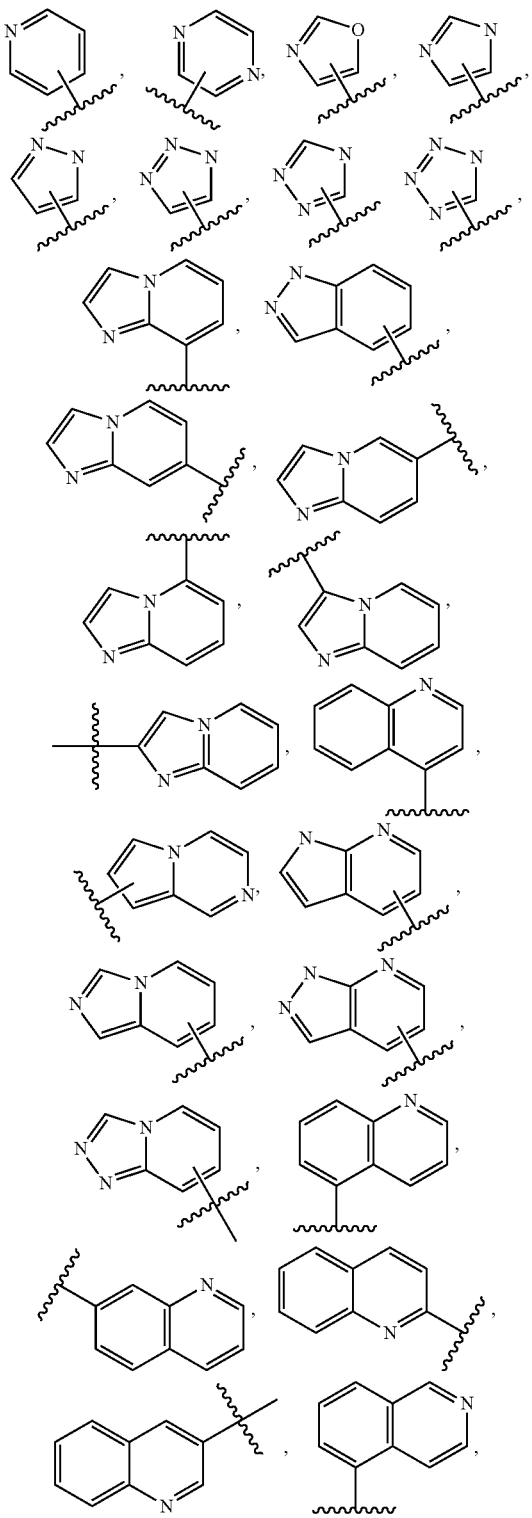

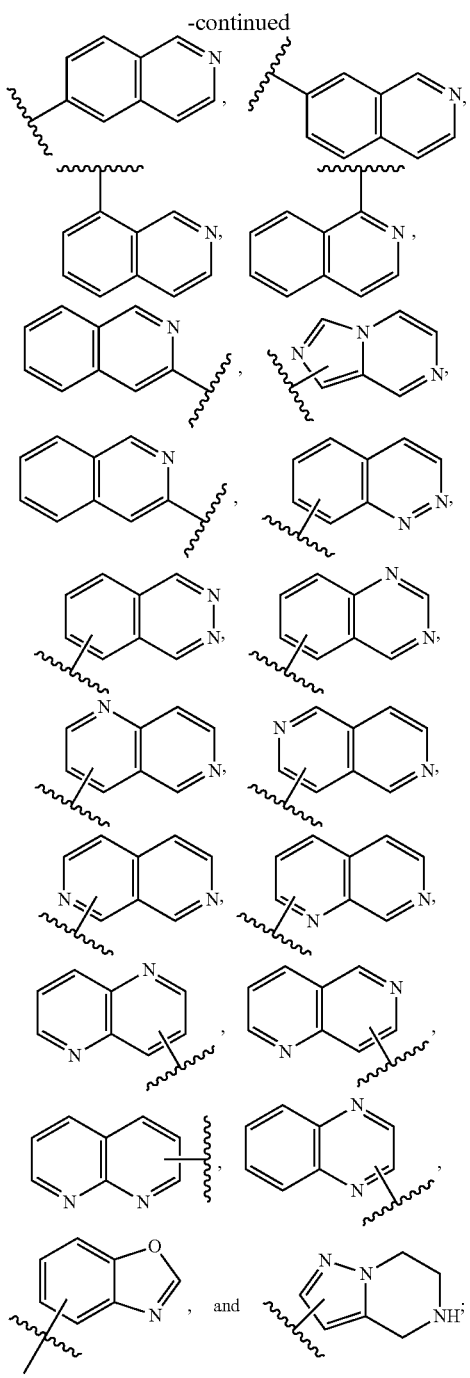

and wherein Q is optionally substituted with one to three $R^a$.

In one group of embodiments, the invention provides a compound of formula Ib, wherein Q is selected from the group consisting of an imidazopyridinyl group, a pyrrolopyridinyl group, a pyrazolopyridinyl group, a triazolopyridinyl group, a pyrazolopyrazinyl group, a pyridinyl group, a pyrazinyl group, an oxazolyl group, an imidazolyl group, a triazolyl group, a tetrazolyl group, a pyrazolyl group, a quinolinyl group, an isoquinolinyl group, and indazolyl group, a benzooxazolyl group, a naphthyridinyl group, a quinoxalinyl group; and wherein Q is optionally substituted with one to three $R^a$.

In one group of embodiments, the invention provides a compound of formula Ib, wherein z is 0. In another group of embodiments, z is 1. In yet another group of embodiments, z is 2. In still another group of embodiments, z is 3. In another group of embodiments, z is 4. In yet another group of embodiments, z is 5. In still another group of embodiments, z is 6.

In other embodiments, the invention provide a compound according to Formula Ic:

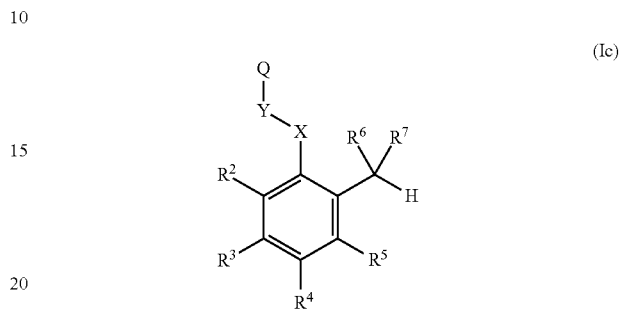

or a tautomer or pharmaceutically acceptable salt thereof, wherein:

Y is O or $CH_2$;

X is O or $CH_2$;

Q is selected from the group consisting of:

i) imidazopyridinyl, methylimidazopyridinyl, indazolyl, pyrrolopyridinyl, pyrrolopyrazinyl, pyrazolopyridinyl, pyrazolopyrazinyl, and quinolinyl, each of which is optionally substituted with one to three $R^a$; wherein $R^2$, $R^3$, $R^4$, and $R^5$, are independently selected from the group consisting of hydrogen, halo, $R^b$, $OR^d$, $O(CH_2)_zOR^d$, $O(CH_2)_zNR^dR^d$, $OC(O)R^e$, $SR^d$, CN, $NO_2$, $CO_2R^d$, $CONR^dR^d$, $C(O)R^d$, $OC(O)NR^dR^d$, $NR^dR^d$, $NR^dC(O)R^e$, $NR^dC(O)_2R^e$, $NR^dC(O)NR^dR^d$, $S(O)R^e$, $S(O)_2R^e$, $NR^dS(O)_2R^e$, $S(O)_2NR^dR^d$, and $N_3$ where z is 1, 2, or 3; and ii) pyridinyl and piperidinyl, each of which is optionally substituted with one to three $R^a$; wherein $R^2$, $R^3$, and $R^4$ are independently selected from the group consisting of hydrogen, halo, $R^b$, $OR^d$, $O(CH_2)_zOR^d$, $O(CH_2)_zNR^dR^d$, $OC(O)R^e$, $SR^d$, CN, $NO_2$, $CO_2R^d$, $CONR^dR^d$, $C(O)R^d$, $OC(O)NR^dR^d$, $NR^dR^d$, $NR^dC(O)R^e$, $NR^dC(O)_2R^e$, $NR^dC(O)NR^dR^d$, $S(O)R^e$, $S(O)_2R^e$, $NR^dS(O)_2R^e$, $S(O)_2NR^dR^d$, and $N_3$ where z is 1, 2, or 3; and $R^5$ is selected from the group consisting of halo and $OR^d$;

$R^6$ and $R^7$ together form oxo or an aldehyde protecting group;

each $R^a$ is independently selected from the group consisting of halo, oxo, $R^b$, $OR^d$, $O(CH_2)_uOR^d$, $O(CH_2)_uNR^dR^d$, $O(CH_2)_uNR^dC(O)R^e$, $O(CH_2)_uNR^dC(O)_2R^e$, $O(CH_2)_uNR^dS(O)_2R^e$, $NH_2$, $-(CH_2)_kOC(O)R^e$, $-(CH_2)_kSR^d$, CN, $NO_2$, $-(CH_2)_kCO_2(C_{1-8}alkyl)OH$, $-(CH_2)_kCO_2(C_{1-8}alkyl)(heteroaryl)C(O)(C_{1-8}alkyl)$, $-(CH_2)_kCO_2R^d$, $-(CH_2)_kCONR^dR^d$, $-(CH_2)_kNR^dC(O)R^e$, $-(CH_2)_kNR^dC(O)_2R^e$, $-(CH_2)_kC(O)R^d$, $-(CH_2)_kOC(O)NR^dR^d$, $-NR^d(CH_2)_uOR^d$, $-NR^d(CH_2)NR^dR^d$, $-NR^d(CH_2)_uNR^dC(O)R^e$, $-NR^d(CH_2)_uNR^dC(O)_2R^e$, $-NR^d(CH_2)_uNR^dS(O)_2R^e$, $-(CH_2)_kNR^dC(O)R^e$, $-(CH_2)_kNR^dC(O)_2R^d$, $-(CH_2)_kNR^dC(O)NR^dR^d$, $-(CH_2)_kS(O)R^e$, $-(CH_2)_k$ S(O)$_2$R$^e$, —(CH$_2$)$_k$NR$^d$S(O)$_2$R$^e$, —C(O)(CH$_2$)$_k$NR$^d$S(O)$_2$R$^e$, —(CH$_2$)$_k$C(O)NR$^d$S(O)$_2$R$^e$, —(CH$_2$)$_k$S(O)$_2$NR$^d$R$^d$, N$_3$, —(CH$_2$)$_k$aryl optionally substituted with one to three R$^c$, —NR$^d$(CH$_2$)$_k$aryl optionally substituted with one to three R$^c$, —(CH$_2$)$_k$heteroaryl optionally substituted with one to three R$^c$, —NR$^d$(CH$_2$)$_k$heteroaryl optionally substituted with one to three R$^c$, —(CH$_2$)$_k$heterocycloalkyl optionally substituted with one to three R$^c$, and —NR$^d$(CH$_2$)$_k$heterocycloalkyl optionally substituted with one to three R$^c$ where k is 0, 1, 2, 3, 4, 5, or 6 and u is 1, 2, 3, 4, 5, or 6;

each R$^b$ is independently selected from the group consisting of C$_{1-8}$alkyl, C$_{2-8}$alkenyl, and C$_{2-8}$alkynyl, each optionally independently substituted with one to three halo, OR$^d$, or NR$^d$R$^d$;

each R$^c$ is independently selected from the group consisting of halo, C$_{1-8}$alkyl, haloC$_{1-8}$alkyl, C$_{2-8}$alkenyl, haloC$_{2-8}$alkenyl, C$_{2-8}$alkynyl, haloC$_{2-8}$alkynyl, (CH$_2$)$_m$OR$^f$, OC(O)R$^g$, SR$^f$, CN, NO$_2$, (CH$_2$)$_m$CO$_2$R$^f$, CONR$^f$R$^f$, C(O)R$^f$, OC(O)NR$^f$R$^f$, (CH$_2$)$_m$NR$^f$R$^f$, NR$^f$C(O)R$^g$, NR$^f$C(O)$_2$R$^g$, NR$^f$C(O)NR$^f$R$^f$, S(O)R$^g$, S(O)$_2$R$^g$, NR$^f$S(O)$_2$R$^g$, S(O)$_2$NR$^f$R$^f$, N$_3$, (R$^f$)$_m$SiC$_{1-8}$alkyl, heteroaryl optionally substituted with one to three R$^h$, cycloalkyl optionally substituted with one to three R$^h$, and heterocycloalkyl optionally substituted with one to three R$^h$ where m is selected from the group consisting of 0, 1, 2, 3, 4, 5, and 6;

each R$^h$ is independently selected from the group consisting of halo, C$_{1-8}$alkyl, haloC$_{1-8}$alkyl, OR$^j$, OC(O)R, SR$^j$, NO$_2$, CO$_2$R$^j$, CONR$^j$R$^j$, C(O)R$^j$, OC(O)NR$^j$R$^j$, NR$^j$R$^j$, NR$^j$C(O)R$^t$, NR$^j$C(O)$_2$R$^t$, NR$^j$C(O)NR$^j$R$^j$, S(O)R$^t$, S(O)$_2$R$^t$, NR$^j$S(O)$_2$R$^t$, and S(O)$_2$NR$^j$R$^j$;

R$^d$, R$^f$, and R$^j$ are each independently selected from the group consisting of hydrogen, C$_{1-8}$ alkyl, haloC$_{1-8}$alkyl, C$_{2-8}$ alkenyl, haloC$_{2-8}$alkenyl, C$_{2-8}$ alkynyl, and halo C$_{2-8}$alkynyl; and R$^e$, R$^g$, and R$^t$ are each independently selected from the group consisting of C$_{1-8}$alkyl, haloC$_{1-8}$alkyl, C$_{2-8}$ alkenyl, haloC$_{2-8}$alkenyl, C$_{2-8}$ alkynyl, and haloC$_{2-8}$alkynyl.

In one group of embodiments, the invention provides a compound of formula Ic, wherein Q is selected from the group consisting of imidazo[1,5-a]pyridin-8-yl, imidazo[1,5-a]pyridin-6-yl, imidazo[1,5-a]pyridin-5-yl, imidazo[1,2-a]pyridin-8-yl, imidazo[1,2-a]pyridin-7-yl, imidazo[1,2-a]pyridin-6-yl, imidazo[1,2-a]pyridin-5-yl, imidazo[1,2-a]pyridin-3-yl, 8-methylimidazo[1,2-a]pyridin-2-yl, indazol-4-yl, pyrrolo[2,3-b]pyridin-4-yl, pyrrolo[1,2-a]pyrazin-6-yl, pyrrolo[1,2-a]pyrazin-4-yl, pyrazolo[3,4-b]pyridin-4-yl, pyrazolo[1,5-a]pyrazin-3-yl, and quinolin-5-yl, each of which is optionally substituted with one to three R$^a$.

In one group of embodiments, the invention provides a compound of formula Ic, wherein z is 1. In another group of embodiments, z is 2. In still another group of embodiments, z is 3.

In one group of embodiments, the invention provides a compound wherein: Y is CH$_2$, and X is CH$_2$.

In one group of embodiments, the invention provides a compound of formula Ic, wherein R$^2$ is selected from the group consisting of H and OR$^d$;

R$^3$ is selected from the group consisting of H, CN, halo, and OR$^d$;

R$^4$ is selected from the group consisting of H, CN, and OR$^d$: and

R$^5$ is H.

In one group of embodiments, the invention provides a compound of formula Ic, wherein R$^4$ is methoxy.

In one group of embodiments, the invention provides a compound of formula Ic, wherein Q is selected from the group consisting of pyridine-3-yl and piperidin-1-yl.

In one group of embodiments, the invention provides a compound of formula Ic, wherein R$^5$ is selected from the group consisting of hydroxy and fluoro.

In one group of embodiments, the invention provides a compound of formula Ic, wherein R$^6$ and R$^7$ together form oxo.

In one group of embodiments, a compound is selected from Table 1 below or a tautomer or pharmaceutically acceptable salt thereof.

TABLE 1

| Compound | Structure | Name |
|---|---|---|
| 1 | 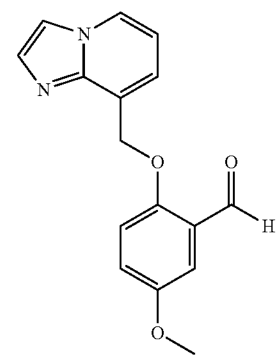 [SMILES: COc1ccc(OCc2cccn3ccnc23)c(C=O)c1] | 2-(imidazo[1,2-a]pyridin-8-ylmethoxy)-5-methoxy-benzaldehyde |
| 2 | 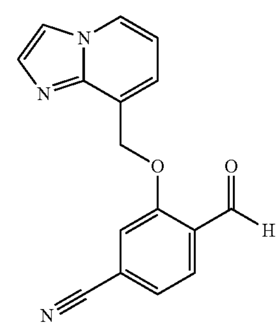 [SMILES: N#Cc1ccc(C=O)c(OCc2cccn3ccnc23)c1] | 4-formyl-3-(imidazo[1,2-a]pyridin-8-ylmethoxy)benzonitrile |
| 3 | 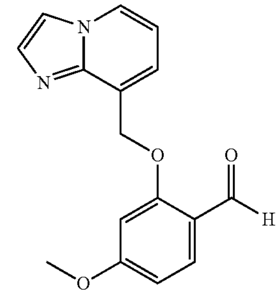 [SMILES: COc1ccc(C=O)c(OCc2cccn3ccnc23)c1] | 2-(imidazo[1,2-a]pyridin-8-ylmethoxy)-4-methoxy-benzaldehyde |

TABLE 1-continued

| Compound | Structure | Name |
|---|---|---|
| 4 | 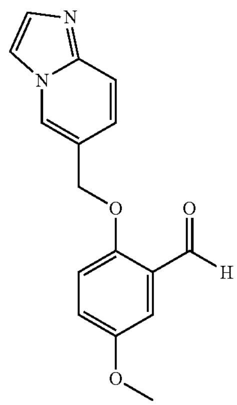 [SMILES: COc1ccc(OCc2ccc3nccn3c2)c(C=O)c1] | 2-(imidazo[1,2-a]pyridin-6-ylmethoxy)-5-methoxy-benzaldehyde |
| 5 | 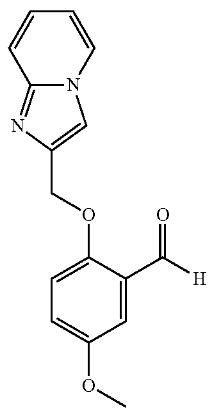 [SMILES: COc1ccc(OCc2cn3ccccc3n2)c(C=O)c1] | 2-(imidazo[1,2-a]pyridin-2-ylmethoxy)-5-methoxy-benzaldehyde |
| 6 | 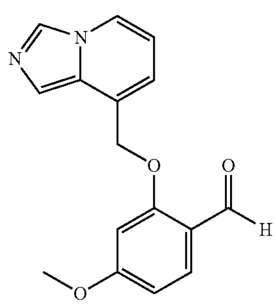 [SMILES: COc1ccc(C=O)c(OCc2cccn3cncc23)c1] | 2-(imidazo[1,5-a]pyridin-8-ylmethoxy)-4-methoxy-benzaldehyde |
| 7 | 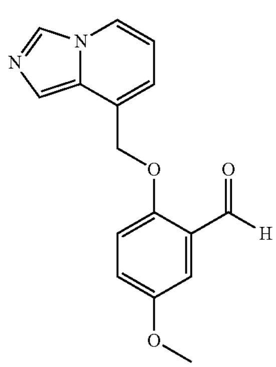 [SMILES: COc1ccc(OCc2cccn3cncc23)c(C=O)c1] | 2-(imidazo[1,5-a]pyridin-8-ylmethoxy)-5-methoxy-benzaldehyde |
| 8 | | 2-(imidazo[1,2-a]pyridin-7-ylmethoxy)-5-methoxy-benzaldehyde |
| 9 | | 2-(imidazo[1,2-a]pyridin-3-ylmethoxy)-5-methoxy-benzaldehyde |
| 10 | | 5-methoxy-2-(quinolin-5-ylmethoxy)benzaldehyde |
| 11 | | 5-bromo-2-(imidazo[1,2-a]pyridin-8-ylmethoxy)benzaldehyde |

TABLE 1-continued

| Compound | Structure | Name |
|---|---|---|
| 12 | 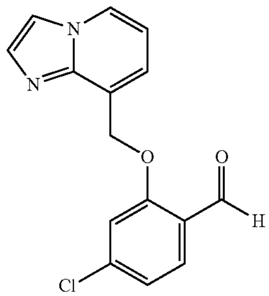 [SMILES: O=Cc1ccc(Cl)cc1OCc1cccn2ccnc12] | 4-chloro-2-(imidazo[1,2-a]pyridin-8-ylmethoxy)benzaldehyde |
| 13 | 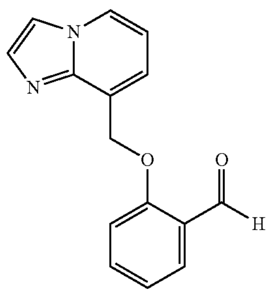 [SMILES: O=Cc1ccccc1OCc1cccn2ccnc12] | 2-(imidazo[1,2-a]pyridin-8-ylmethoxy)benzaldehyde |
| 14 | 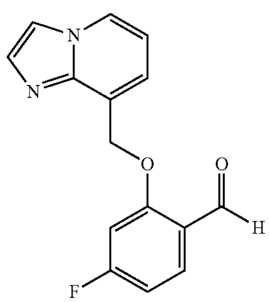 [SMILES: O=Cc1ccc(F)cc1OCc1cccn2ccnc12] | 4-fluoro-2-(imidazo[1,2-a]pyridin-8-ylmethoxy)benzaldehyde |
| 15 | 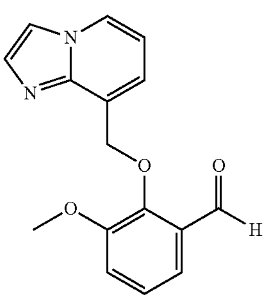 [SMILES: COc1cccc(C=O)c1OCc1cccn2ccnc12] | 2-(imidazo[1,2-a]pyridin-8-ylmethoxy)-3-methoxybenzaldehyde |
| 16 | 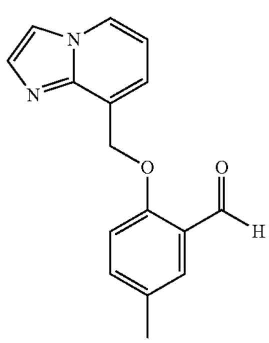 [SMILES: Cc1ccc(OCc2cccn3ccnc23)c(C=O)c1] | 2-(imidazo[1,2-a]pyridin-8-ylmethoxy)-5-methylbenzaldehyde |
| 17 | 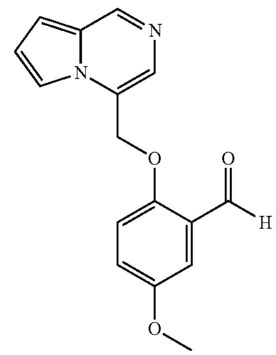 [SMILES: COc1ccc(OCc2cncc3cccn23)c(C=O)c1] | 5-methoxy-2-(pyrrolo[1,2-a]pyrazin-4-ylmethoxy)benzaldehyde |
| 18 | 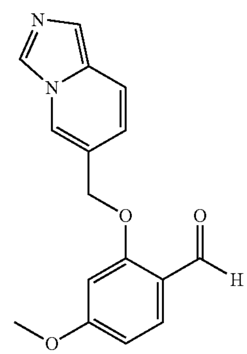 [SMILES: COc1ccc(C=O)c(OCc2ccc3cncn3c2)c1] | 2-(imidazo[1,5-a]pyridin-6-ylmethoxy)-4-methoxybenzaldehyde |
| 19 | 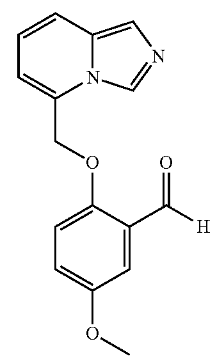 [SMILES: COc1ccc(OCc2cccc3cncn23)c(C=O)c1] | 2-(imidazo[1,5-a]pyridin-5-ylmethoxy)-5-methoxybenzaldehyde |
| 20 | 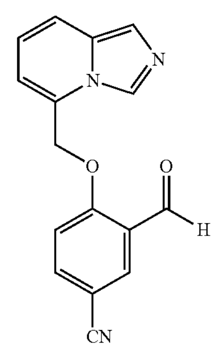 [SMILES: N#Cc1ccc(OCc2cccc3cncn23)c(C=O)c1] | 3-formyl-4-(imidazo[1,5-a]pyridin-5-ylmethoxy)benzonitrile |

TABLE 1-continued

| Compound | Structure | Name |
|---|---|---|
| 21 | 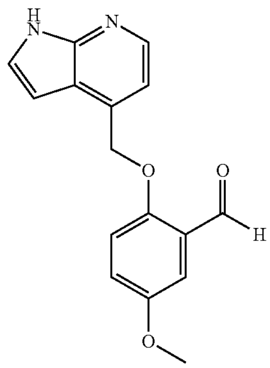 [SMILES: COc1ccc(OCc2ccnc3[nH]ccc23)c(C=O)c1] | 2-((1H-pyrrolo[2,3-b]pyridin-4-yl)methoxy)-5-methoxy-benzaldehyde |
| 22 | 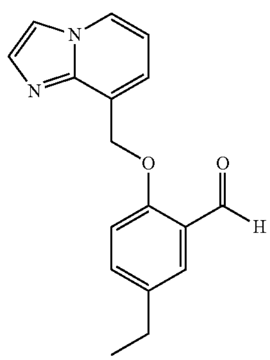 [SMILES: CCc1ccc(OCc2cccn3ccnc23)c(C=O)c1] | 5-ethyl-2-(imidazo[1,2-a]pyridin-8-ylmethoxy)benzaldehyde |
| 23 | 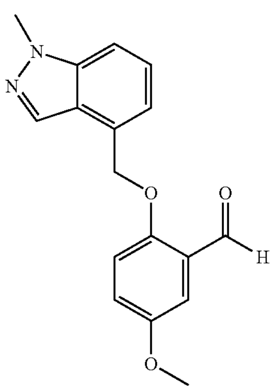 [SMILES: COc1ccc(OCc2cccc3c2cnn3C)c(C=O)c1] | 5-methoxy-2-((1-methyl-1H-indazol-4-yl)methoxy)benzaldehyde |
| 24 | 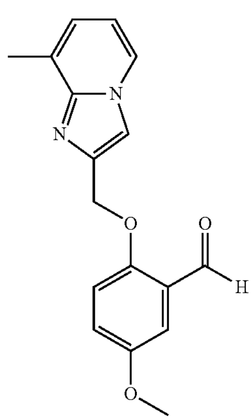 [SMILES: COc1ccc(OCc2cn3cccc(C)c3n2)c(C=O)c1] | 5-methoxy-2-((8-methylimidazo[1,2-a]pyridin-2-yl)methoxy)benzaldehyde |
| 25 | | 2-((1H-indazol-4-yl)methoxy)-5-methoxy-benzaldehyde |
| 26 | | 2-((1H-pyrrolo[2,3-b]pyridin-4-yl)methoxy)-5-methoxy-benzaldehyde |
| 27 | | 3-formyl-4-(imidazo[1,2-a]pyridin-8-ylmethoxy)benzonitrile |
| 28 | | 5-methoxy-2-(pyrrolo[1,2-a]pyrazin-6-ylmethoxy)benzaldehyde |

TABLE 1-continued

| Compound | Structure | Name |
|---|---|---|
| 29 | 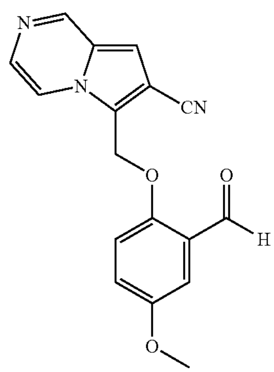 [SMILES: COc1ccc(OCc2c(C#N)cc3cnccn23)c(C=O)c1] | 6-((2-formyl-4-methoxyphenoxy)methyl)pyrrolo[1,2-a]pyrazine-7-carbonitrile |
| 30 | 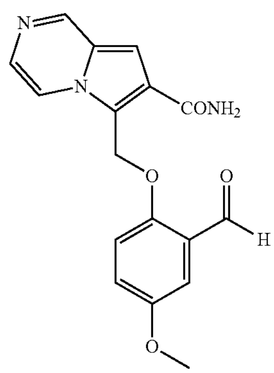 [SMILES: COc1ccc(OCc2c(C(N)=O)cc3cnccn23)c(C=O)c1] | 6-((2-formyl-4-methoxyphenoxy)methyl)pyrrolo[1,2-a]pyrazine-7-carboxamide |
| 31 | 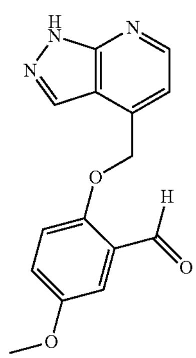 | 2-((1H-pyrazolo[3,4-b]pyridin-4-yl)methoxy)-5-methoxy-benzaldehyde |
| 32 | 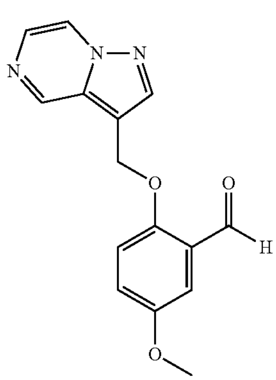 [SMILES: COc1ccc(OCc2cnn3ccncc23)c(C=O)c1] | 5-methoxy-2-(pyrazolo[1,5-a]pyrazin-3-ylmethoxy)benzaldehyde |
| 33 | 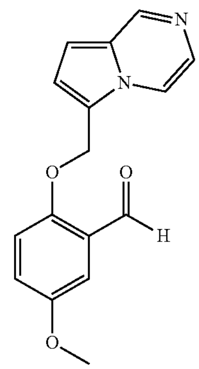 [SMILES: COc1ccc(OCc2ccc3cnccn23)c(C=O)c1] | 5-methoxy-2-(pyrrolo[1,2-a]pyrazin-6-ylmethoxy)benzaldehyde |
| 34 | 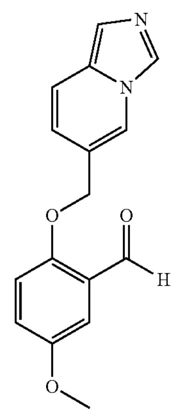 [SMILES: COc1ccc(OCc2ccc3cncn3c2)c(C=O)c1] | 2-(imidazo[1,5-a]pyridin-6-ylmethoxy)-5-methoxy-benzaldehyde |
| 35 | 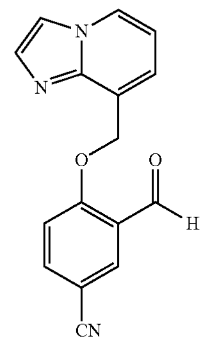 [SMILES: N#Cc1ccc(OCc2cccn3ccnc23)c(C=O)c1] | 3-formyl-4-(imidazo[1,2-a]pyridin-8-ylmethoxy)benzonitrile |
| 36 | 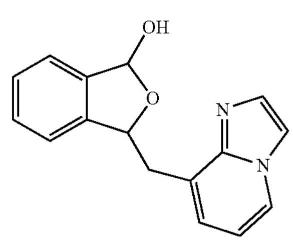 [SMILES: OC1OC(Cc2cccn3ccnc23)c2ccccc21] | 3-(imidazo[1,2-a]pyridin-8-ylmethyl)-1,3-dihydro-isobenzofuran-1-ol |

TABLE 1-continued

| Compound | Structure | Name |
|---|---|---|
| 37 | 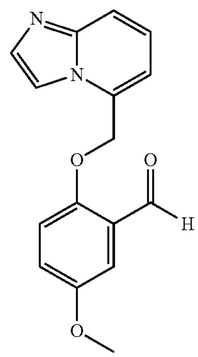 [SMILES: COc1ccc(OCc2cccc3nccn23)c(C=O)c1] | 2-(imidazo[1,2-a]pyridin-5-ylmethoxy)-5-methoxybenzaldehyde |
| 38 | 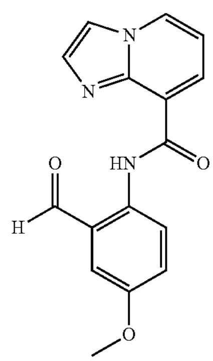 [SMILES: COc1ccc(NC(=O)c2cccn3ccnc23)c(C=O)c1] | N-(2-formyl-4-methoxyphenyl)imidazo[1,2-a]pyridine-8-carboxamide |
| 39 | 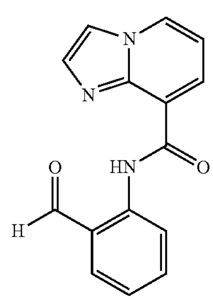 [SMILES: O=Cc1ccccc1NC(=O)c1cccn2ccnc12] | N-(2-formylphenyl)imidazo[1,2-a]pyridine-8-carboxamide |
| 40 | 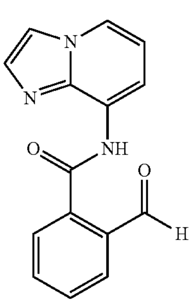 [SMILES: O=Cc1ccccc1C(=O)Nc1cccn2ccnc12] | 2-formyl-N-(imidazo[1,2-a]pyridin-8-yl)benzamide |
| 41 | 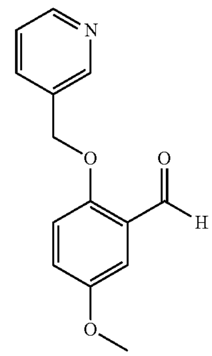 [SMILES: COc1ccc(OCc2cccnc2)c(C=O)c1] | 5-methoxy-2-(pyridin-3-ylmethoxy)benzaldehyde |
| 42 | 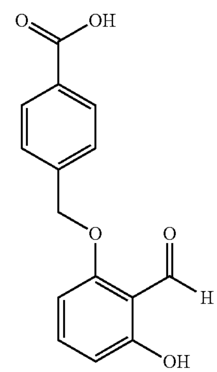 [SMILES: O=Cc1c(O)cccc1OCc1ccc(C(=O)O)cc1] | 4-((2-formyl-3-hydroxyphenoxy)methyl)benzoic acid |
| 43 | 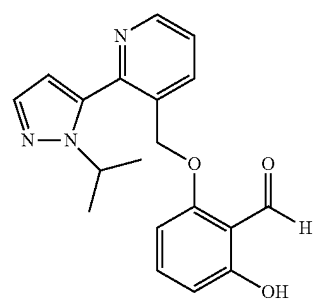 [SMILES: CC(C)n1nccc1-c1ncccc1COc1cccc(O)c1C=O] | 2-hydroxy-6-((2-(1-isopropyl-1H-pyrazol-5-yl)pyridin-3-yl)methoxy)benzaldehyde |
| 44 | 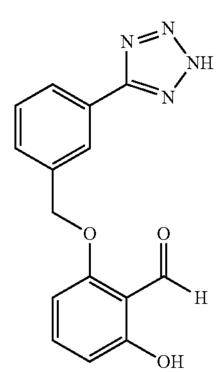 [SMILES: O=Cc1c(O)cccc1OCc1cccc(-c2nn[nH]n2)c1] | 2-((3-(2H-tetrazol-5-yl)benzyl)oxy)-6-hydroxybenzaldehyde |

TABLE 1-continued

| Compound | Structure | Name |
|---|---|---|
| 45 | 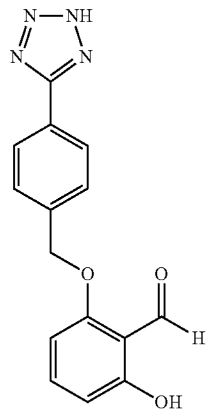 [SMILES: O=Cc1c(O)cccc1OCc1ccc(-c2nn[nH]n2)cc1] | 2-((4-(2H-tetrazol-5-yl)benzyl)oxy)-6-hydroxy-benzaldehyde |
| 46 | 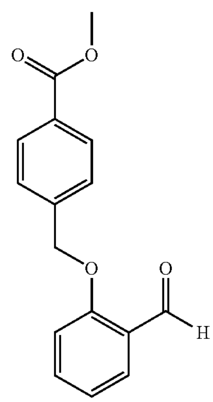 [SMILES: COC(=O)c1ccc(COc2ccccc2C=O)cc1] | methyl 4-((2-formylphenoxy)methyl)benzoate |
| 47 | 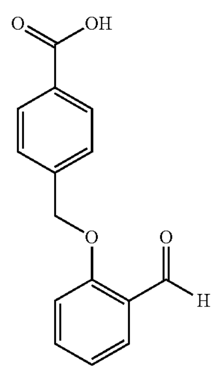 [SMILES: O=Cc1ccccc1OCc1ccc(C(=O)O)cc1] | 4-((2-formylphenoxy)methyl)benzoic acid |
| 48 | 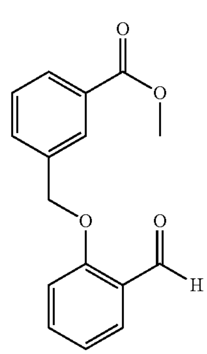 [SMILES: COC(=O)c1cccc(COc2ccccc2C=O)c1] | methyl 3-((2-formylphenoxy)methyl)benzoate |
| 49 | | 2-bromo-3-((2-(1-isopropyl-1H-pyrazol-5-yl)pyridin-3-yl)methoxy)benzaldehyde |
| 50 | | 2-hydroxy-6-((2-(1-(2,2,2-trifluoroethyl)-1H-pyrazol-5-yl)pyridin-3-yl)methoxy)benzaldehyde |
| 51 | | 2-hydroxy-6-((2-(1-(3,3,3-trifluoropropyl)-1H-pyrazol-5-yl)pyridin-3-yl)methoxy)benzaldehyde |
| 52 | | 2-fluoro-6-((2-(1-(2,2,2-trifluoroethyl)-1H-pyrazol-5-yl)pyridin-3-yl)methoxy)benzaldehyde |

TABLE 1-continued

| Compound | Structure | Name |
|---|---|---|
| 53 | 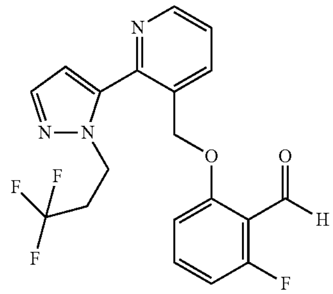 [SMILES: O=Cc1c(F)cccc1OCc1cccnc1-c1ccnn1CCC(F)(F)F] | 2-fluoro-6-((2-(1-(3,3,3-trifluoropropyl)-1H-pyrazol-5-yl)pyridin-3-yl)methoxy)benzaldehyde |
| 54 | 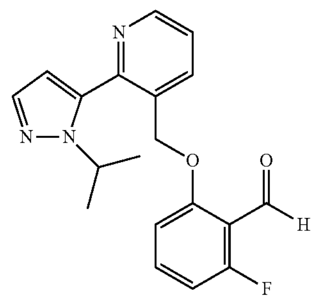 [SMILES: CC(C)n1nccc1-c1ncccc1COc1cccc(F)c1C=O] | 2-fluoro-6-((2-(1-isopropyl-1H-pyrazol-5-yl)pyridin-3-yl)methoxy)benzaldehyde |
| 55 | 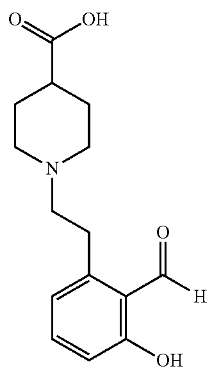 [SMILES: O=Cc1c(O)cccc1CCN1CCC(C(=O)O)CC1] | 1-(2-formyl-3-hydroxyphenethyl)piperidine-4-carboxylic acid |

In one group of embodiments, the compound is selected from:
2-(imidazo[1,2-a]pyridin-8-ylmethoxy)-5-methoxybenzaldehyde,
2-(imidazo[1,2-a]pyridin-2-ylmethoxy)-5-methoxybenzaldehyde,
2-(imidazo[1,5-a]pyridin-8-ylmethoxy)-5-methoxybenzaldehyde,
5-methoxy-2-(quinolin-5-ylmethoxy)benzaldehyde,
5-methoxy-2-((1-methyl-1H-indazol-4-yl)methoxy)benzaldehyde,
5-methoxy-2-((8-methylimidazo[1,2-a]pyridin-2-yl)methoxy)benzaldehyde,
2-((1H-indazol-4-yl)methoxy)-5-methoxybenzaldehyde,
5-methoxy-2-(pyridin-3-ylmethoxy)benzaldehyde,
2-((2-(1-isopropyl-1H-pyrazol-5-yl)pyridin-3-yl)methoxy)-5-methoxybenzaldehyde,
2-hydroxy-6-((2-(1-isopropyl-1H-pyrazol-5-yl)pyridin-3-yl)methoxy)benzaldehyde,
2-((3-(2H-tetrazol-5-yl)benzyl)oxy)-6-hydroxybenzaldehyde,
2-((4-(2H-tetrazol-5-yl)benzyl)oxy)-6-hydroxybenzaldehyde, methyl 4-((2-formylphenoxy)methyl)benzoate,
4-((2-formylphenoxy)methyl)benzoic acid, methyl 3-((2-formylphenoxy)methyl)benzoate,
2-bromo-3-((2-(1-isopropyl-1H-pyrazol-5-yl)pyridin-3-yl)methoxy)benzaldehyde,
2-hydroxy-6-((2-(1-(2,2,2-trifluoroethyl)-1H-pyrazol-5-yl)pyridin-3-yl)methoxy)benzaldehyde,
2-hydroxy-6-((2-(1-(3,3,3-trifluoropropyl)-1H-pyrazol-5-yl)pyridin-3-yl)methoxy)benzaldehyde,
2-fluoro-6-((2-(1-(2,2,2-trifluoroethyl)-1H-pyrazol-5-yl)pyridin-3-yl)methoxy)benzaldehyde,
2-fluoro-6-((2-(1-(3,3,3-trifluoropropyl)-1H-pyrazol-5-yl)pyridin-3-yl)methoxy)benzaldehyde,
2-fluoro-6-((2-(1-isopropyl-1H-pyrazol-5-yl)pyridin-3-yl)methoxy)benzaldehyde, and
1-(2-formyl-3-hydroxyphenethyl)piperidine-4-carboxylic acid, or a tautomer or pharmaceutically acceptable salt thereof.

In one group of embodiments, provided is a compound in any of the Examples or Tables. In another group of embodiments, provided are any combinations of subembodiments as disclosed herein including any combination of elements disclosed herein including the a selection of any single elements.

In one group of embodiments, provided is a pharmaceutical composition comprising a compound of any of the above embodiments or a tautomer or pharmaceutically acceptable salt thereof.

In one group of embodiments, provided is a pharmaceutical composition comprising a compound that is

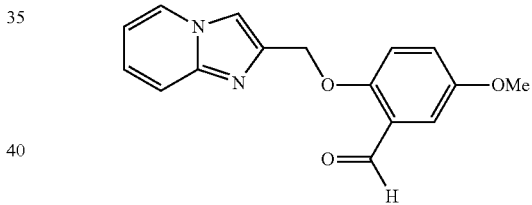

or a pharmaceutically acceptable salt thereof.

The compounds of the present invention may be prepared by known organic synthesis techniques, including the methods described in more detail in the Examples.

In one group of embodiments, provided is an intermediate compound used in the preparation of the compounds disclosed herein.

In one group of embodiments, provided are methods for preparing the compounds disclosed herein.

For example, Scheme I shows a synthetic route for the synthesis of the compounds of Formula (I) where X is O and Y is CH$_2$. Phenol 1.1 is contacted with intermediate 1.2 in the presence of base under ether forming conditions to give ether 1.3, where Lg represents a leaving group such as a halogen leaving group. Conversely, when X is O and Y is CH$_2$, the compounds of Formula (I) can be prepared using the appropriate starting materials where the OH moiety of intermediate 1.1 is replaced with a leaving group and the Lg group of intermediate 1.2 is replaced with an OH group.

Scheme I

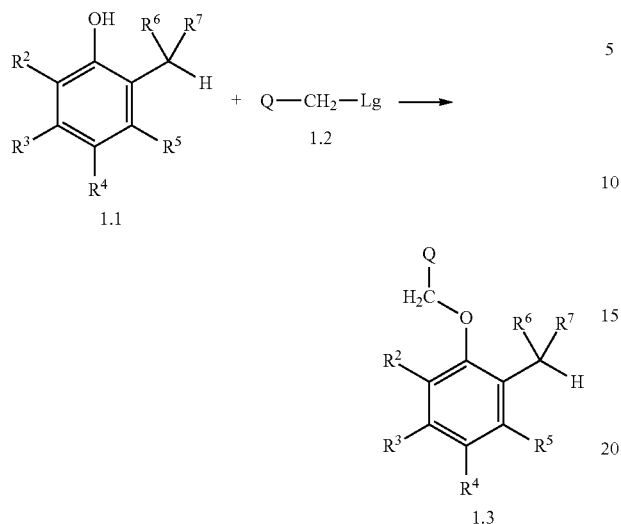

Scheme II shows an example of a synthetic route for the synthesis of the compounds of Formula (I) where X and Y are CH$_2$. Alkene 2.1 is contacted with alkene 2.2 under metathesis forming conditions in the presence of an appropriate transition metal catalyst. Suitable catalysts include ruthenium catalysts such as Grubbs' catalyst. Product 2.3 is then hydrogenated to give compound 2.4.

Scheme II

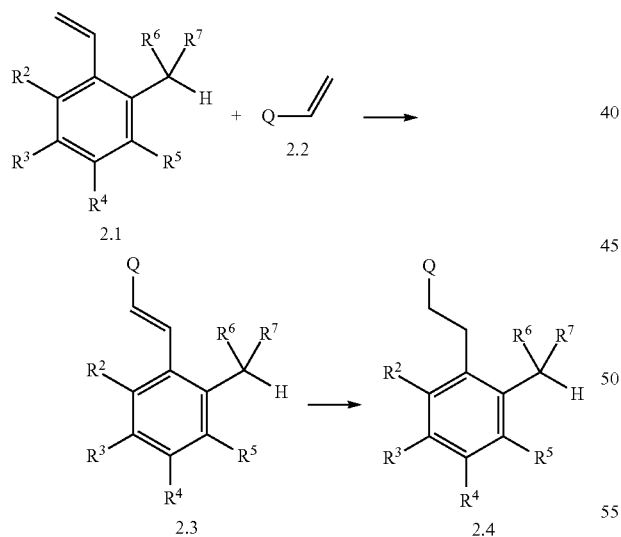

Scheme III shows an example of a synthetic route for the synthesis of the compounds of Formula (I) where R$^6$ together with R$^{1b}$ form a cyclic ether. Compound 3.1, is reacted with diethylphosphite and a base such as sodium methoxide to give intermediate 3.2, that is then condensed with aldehyde 3.3 to give alkene 3.4. Treatment of the alkene with H$_2$ under hydrogenation conditions gives lactone 3.4, which is then reduced with a suitable reducing agent such as LiBHEt$_3$ to give cyclic hemiacetal 3.5.

Scheme III

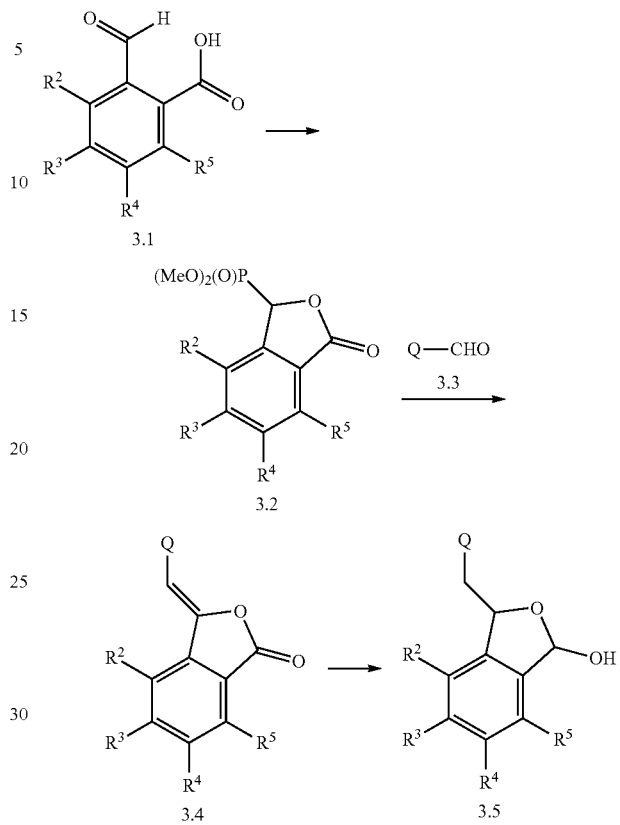

Scheme IV shows an example of synthesis of the compounds of Formula (I) where Q is pyridine-3-yl and R$^a$ heteroaryl. Acid 4.1 is reduced to alcohol 4.2 using known methods such as by forming the anhydride (e.g. treatment with triethylamine and i-butyl chloroformate) followed by reduction with NaBH$_4$. Alcohol 4.2 is converted to chloride 4.3 such as by treatment with thionyl chloride. Coupling of the halide with alcohol 4.4 under ether forming conditions gives the precursor 4.5 that can be functionalized with a variety to heteroaryl R$^a$ groups. For example, 4.5 can be coupled with pyrazole 4.6 under known organometallic coupling conditions (e.g. Pd(PPh$_3$)$_4$) to give 4.7, where PG is a nitrogen protecting group such as a silyl protecting group that can be removed to give the product 4.8.

Scheme IV

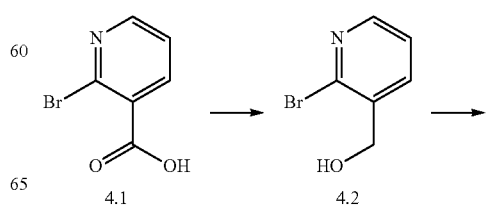

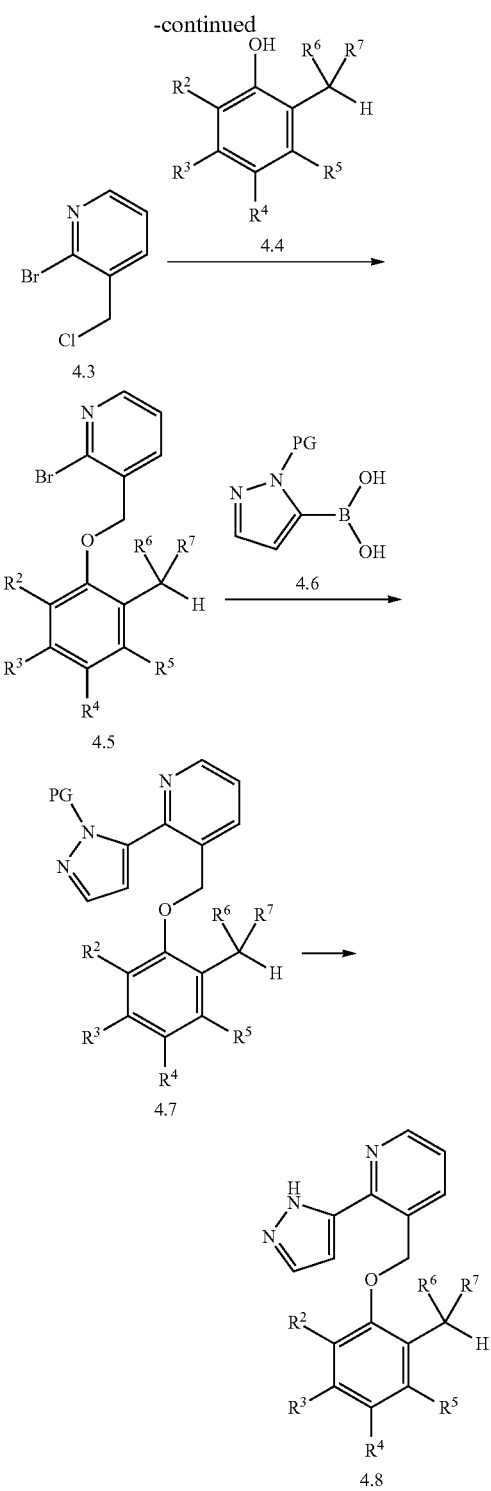

One skilled in the art will recognize that in certain embodiments it may be advantageous to use a protecting group strategy. The protecting group can be removed using methods known to those skilled in the art.

In one group of embodiments, certain of the compounds disclosed herein may generally be utilized as the free base. Alternatively, certain of the compounds may be used in the form of acid addition salts.

It is understood that in another group of embodiments, any of the above embodiments may also be combined with other embodiments listed herein, to form other embodiments of the invention. Similarly, it is understood that in other embodiments, listing of groups includes embodiments wherein one or more of the elements of those groups is not included.

III. Compositions and Methods of Administration

Depending on the intended mode of administration, the pharmaceutical compositions may be in the form of solid, semi-solid or liquid dosage forms, preferably in unit dosage form suitable for single administration of a precise dosage. In addition to an effective amount of the active compound(s), the compositions may contain suitable pharmaceutically-acceptable excipients, including adjuvants which facilitate processing of the active compounds into preparations which can be used pharmaceutically. "Pharmaceutically acceptable excipient" refers to an excipient or mixture of excipients which does not interfere with the effectiveness of the biological activity of the active compound(s) and which is not toxic or otherwise undesirable to the subject to which it is administered.

For solid compositions, conventional excipients include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by dissolving, dispersing, etc., an active compound as described herein and optional pharmaceutical adjuvants in water or an aqueous excipient, such as, for example, water, saline, aqueous dextrose, and the like, to form a solution or suspension. If desired, the pharmaceutical composition to be administered may also contain minor amounts of nontoxic auxiliary excipients such as wetting or emulsifying agents, pH buffering agents and the like, for example, sodium acetate, sorbitan monolaurate, triethanolamine sodium acetate, triethanolamine oleate, etc.

For oral administration, the composition will generally take the form of a tablet or capsule, or it may be an aqueous or nonaqueous solution, suspension or syrup. Tablets and capsules are preferred oral administration forms. Tablets and capsules for oral use will generally include one or more commonly used excipients such as lactose and corn starch. Lubricating agents, such as magnesium stearate, are also typically added. When liquid suspensions are used, the active agent may be combined with emulsifying and suspending excipients. If desired, flavoring, coloring and/or sweetening agents may be added as well. Other optional excipients for incorporation into an oral formulation include preservatives, suspending agents, thickening agents, and the like.

Injectable formulations can be prepared in conventional forms, either as liquid solutions or suspensions, solid forms suitable for solubilization or suspension in liquid prior to injection, or as emulsions or liposomal formulations. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils, fatty esters or polyols are conventionally employed as solvents or suspending media.

The pharmaceutical compositions of this invention may also be formulated in lyophilized form for parenteral administration. Lyophilized formulations may be reconstituted by addition of water or other aqueous medium and then further diluted with a suitable diluent prior to use. The liquid formulation is generally a buffered, isotonic, aqueous solution. Examples of suitable diluents are isotonic saline solution, 5% dextrose in water, and buffered sodium or ammonium acetate solution. Pharmaceutically acceptable solid or liquid excipients may be added to enhance or stabilize the composition, or to facilitate preparation of the composition.

Typically, a pharmaceutical composition of the present invention is packaged in a container with a label, or instructions, or both, indicating use of the pharmaceutical composition in the treatment of the indicated disease.

The pharmaceutical composition may additionally contain one or more other pharmacologically active agents in addition to a compound of this invention.

Dosage forms containing effective amounts of the modulators are within the bounds of routine experimentation and within the scope of the invention. A therapeutically effective dose may vary depending upon the route of administration and dosage form. The representative compound or compounds of the invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals. It should be understood that a specific dosage and treatment regimen for any particular patient will depend upon a variety of factors, including the activity of the specific compound employed, the age, body weight, general health, sex and diet of the patient, and the time of administration, rate of excretion, drug combination, judgment of the treating physician and severity of the particular disease being treated. The amount of active ingredient(s) will also depend upon the particular compound and other therapeutic agent, if present, in the composition.

IV. Methods

In one group of embodiments, provided is a method for increasing tissue oxygenation, the method comprising administering to a subject in need thereof a therapeutically effective amount of a compound of any of the above embodiments or a tautomer or pharmaceutically acceptable salt thereof.

In one group of embodiments, provided is a method for treating a condition associated with oxygen deficiency, the method comprising administering to a subject in need thereof a therapeutically effective amount of a compound of any of the above embodiments or a tautomer or pharmaceutically acceptable salt thereof.

In one group of embodiments, provided is a method for treating sickle cell disease, cancer, a pulmonary disorder, stroke, high altitude sickness, an ulcer, a pressure sore, Alzheimer's disease, acute respiratory disease syndrome, and a wound, the method comprising administering to a subject in need thereof a therapeutically effective amount of a compound of any of the above embodiments or a tautomer or pharmaceutically acceptable salt thereof.

In one group of embodiments, provided is a method for increasing tissue oxygenation or for treating a condition associated with oxygen deficiency, said method comprising administering to a subject in need thereof a therapeutically effective amount of a compound Formula (II):

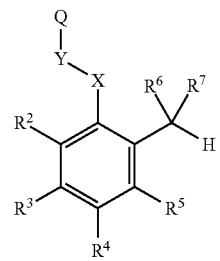

(II)

or a tautomer or pharmaceutically acceptable salt thereof, wherein Q is selected from the group consisting of aryl, heteroaryl, and heterocycloalkyl, each optionally substituted with one to three $R^a$;

Y is O or $CR^{1a}R^{1b}$, where $R^{1a}$ is H or halo and $R^{1b}$ is selected from the group consisting of H, halo, and OH;

X is selected from the group consisting of O, >CH$(CH_2)_nR^8$, and $C(R^9)_2$ where n is 0 or 1, $R^8$ is OH, and $R^9$ is independently H or halo; or Y—X taken together is —NHC(O)— or —C(O)NH—;

$R^2$, $R^3$, $R^4$, and $R^5$ are independently selected from the group consisting of hydrogen, halo, $R^b$, $OR^d$, —O(CH$_2$)$_z$OR$^d$, —O(CH$_2$)$_z$NR$^d$R$^d$, OC(O)R$^e$, SR$^d$, CN, NO$_2$, CO$_2$R$^d$, CONR$^d$R$^d$, C(O)R$^d$, OC(O)NR$^d$R$^d$, NR$^d$R$^d$, NR$^d$C(O)R$^e$, NR$^d$C(O)$_2$R$^e$, NR$^d$C(O)NR$^d$R$^d$, S(O)R$^e$, S(O)$_2$R$^e$, NR$^d$S(O)$_2$R$^e$, S(O)$_2$NR$^d$R$^d$, and N$_3$, where z is 0, 1, 2, 3, 4, 5, or 6; or $R^5$ is —(CH$_2$)$_p$R$^{5a}$ where p is 0 or 1 and $R^{5a}$ is OH;

$R^6$ and $R^7$ together form oxo or an aldehyde protecting group, or $R^6$ together with $R^{1b}$, $R^8$, or $R^5$ forms a cyclic ether where one of $R^{1b}$, $R^8$, or $R^{5a}$ is O, $R^6$ is a bond, and $R^7$ is selected from the group consisting of OH, $C_{1-8}$alkoxy, and halo$C_{1-8}$alkoxy;

each $R^a$ is independently selected from the group consisting of halo, $R^b$, $OR^d$, O(CH$_2$)$_u$OR$^d$, O(CH$_2$)$_u$NR$^d$R$^d$, O(CH$_2$)$_u$NR$^d$C(O)R$^e$, O(CH$_2$)$_u$NR$^d$C(O)$_2$R$^e$, O(CH$_2$)$_u$NR$^d$S(O)$_2$R$^e$, NH$_2$, —(CH$_2$)$_k$OC(O)R$^e$, —(CH$_2$)$_k$SR$^d$, CN, NO$_2$, —(CH$_2$)$_k$CO$_2$(C$_{1-8}$alkyl)OH, —(CH$_2$)$_k$CO$_2$(C$_{1-8}$alkyl)(heteroaryl)C(O)(C$_{1-8}$alkyl), —(CH$_2$)$_k$CO$_2$R$^d$, —(CH$_2$)$_k$CONR$^d$R$^d$, —(CH$_2$)$_k$NR$^d$C(O)R$^e$, —(CH$_2$)$_k$NR$^d$C(O)$_2$R$^e$, —(CH$_2$)$_k$C(O)R$^d$, —(CH$_2$)$_k$OC(O)NR$^d$R$^d$, —NR$^d$(CH$_2$)$_u$OR$^d$, —NR$^d$(CH$_2$)$_u$NR$^d$R$^d$, —NR$^d$(CH$_2$)$_u$NR$^d$C(O)R$^e$, —NR$^d$(CH$_2$)$_u$NR$^d$C(O)$_2$R$^e$, —NR$^d$(CH$_2$)$_u$NR$^d$S(O)$_2$R$^e$, —(CH$_2$)$_k$NR$^d$C(O)R$^e$, —(CH$_2$)$_k$NR$^d$C(O)$_2$R$^d$, —(CH$_2$)$_k$NR$^d$C(O)NR$^d$R$^d$, —(CH$_2$)$_k$S(O)R$^e$, —(CH$_2$)$_k$S(O)$_2$R$^e$, —(CH$_2$)$_k$NR$^d$S(O)$_2$R$^e$, —(CH$_2$)$_k$S(O)$_2$NR$^d$R$^d$, N$_3$, —(CH$_2$)$_k$aryl optionally substituted with one to three $R^c$, —NR$^d$(CH$_2$)$_k$aryl optionally substituted with one to three $R^c$, —(CH$_2$)$_k$heteroaryl optionally substituted with one to three $R^c$, —NR$^d$(CH$_2$)$_k$heteroaryl optionally substituted with one to three $R^c$, —(CH$_2$)$_k$heterocycloalkyl optionally substituted with one to three $R^c$, and —NR$^d$(CH$_2$)$_k$heterocycloalkyl optionally substituted with one to three $R^c$ where k is 0, 1, 2, 3, 4, 5, or 6 and u is 1, 2, 3, 4, 5, or 6;

each $R^b$ is independently selected from the group consisting of $C_{1-8}$alkyl, $C_{2-8}$alkenyl, and $C_{2-8}$ alkynyl, each optionally independently substituted with one to three halo, $OR^d$, or $NR^dR^d$;

each $R^c$ is independently selected from the group consisting of halo, $C_{1-8}$alkyl, halo$C_{1-8}$alkyl, $C_{2-8}$alkenyl, halo$C_{2-8}$alkenyl, $C_{2-8}$alkynyl, halo$C_{2-8}$alkynyl, (CH$_2$)$_m$OR$^f$, OC(O)R$^g$, SR$^f$, CN, NO$_2$, CO$_2$R$^f$, CONR$^f$R$^f$, C(O)R$^f$, OC(O)NR$^f$R$^f$, (CH$_2$)$_m$NR$^f$R$^f$, NR$^f$C(O)R$^g$, NR$^f$C(O)$_2$R$^g$, NR$^f$C(O)NR$^f$R$^f$, S(O)R$^g$, S(O)$_2$R$^g$, NR$^f$S(O)$_2$R$^g$, S(O)$_2$NR$^f$R$^f$, N$_3$, heteroaryl optionally substituted with one to three $R^h$, and heterocycloalkyl optionally substituted with one to three $R^h$ where m is selected from the group consisting of 0, 1, 2, 3, 4, 5, and 6;

$R^d$, $R^f$, and $R^j$ are each independently selected from the group consisting of hydrogen, $C_{1-8}$ alkyl, halo$C_{1-8}$alkyl, $C_{2-8}$ alkenyl, halo$C_{2-8}$alkenyl, $C_{2-8}$ alkynyl, and halo$C_{2-8}$alkynyl; and $R^e$, $R^g$, and $R^i$ are each independently selected from the group consisting of $C_{1-8}$alkyl, halo$C_{1-8}$alkyl, $C_{2-8}$alkenyl, halo$C_{2-8}$alkenyl, $C_{2-8}$ alkynyl, and halo$C_{2-8}$alkynyl;

provided that X and Y are not both O;

provided that when X is O, $R^{1b}$ is not OH;

provided that when Y is O, and n is 0, $R^8$ is not OH; and provided that when $R^6$ and $R^7$ together are oxo, one $R^2$, $R^3$, $R^4$, and $R^5$ is methoxy or ethoxy, and the other of $R^2$, $R^3$, $R^4$, and $R^5$ is H, then Q is not unsubstituted pyridin-2-yl, pyridin-3-yl, or pyridin-4-yl.

In one group of embodiments, provided is a method wherein z is 0. In another group of embodiments, z is 1. In yet another group of embodiments, z is 2. In still another group of embodiments, z is 3. In another group of embodiments, z is 4. In yet another group of embodiments, z is 5. In still another group of embodiments, z is 6.

V. Examples

The following examples are offered to illustrate, but not to limit, the claimed invention.

PREPARATIVE EXAMPLES

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1967-2004, Volumes 1-22; Rodd's Chemistry of Carbon Compounds, Elsevier Science Publishers, 1989, Volumes 1-5 and Supplementals; and Organic Reactions, Wiley & Sons: New York, 2005, Volumes 1-65.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C. to about 75° C.

Referring to the examples that follow, compounds of the present invention were synthesized using the methods described herein, or other methods known in the art.

Example 1

Preparation of 2-(imidazo[1,5-a]pyridin-8-yl-methoxy)-5-methoxybenzaldehyde

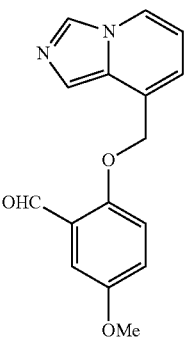 [SMILES: COc1ccc(OCc2cccn3cncc23)c(C=O)c1]

Step 1:

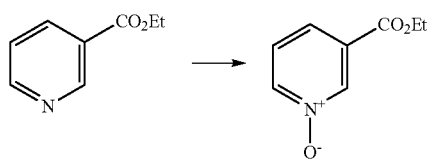 [SMILES: CCOC(=O)c1cccnc1 ; CCOC(=O)c1ccc[n+]([O-])c1]

To a cold solution of 3-ethoxycarbonylpyridine (25 g, 165.4 mmol, 1 eq) in DCM was slowly added mCPBA (70% wt, 198.5 mmol) and the reaction mixture was stirred at rt overnight. Reaction was cooled and diluted with DCM and then neutralized with slow addition of sat. $NaHCO_3$. Aqueous layer was washed with DCM (3×) and the combined organic layer was dried and evaporated to give a residue, which was purified by column chromatography (EtOAc/MeOH) to give 3-ethoxycarbonylpyridine N-oxide (13.6 g). MS: exact mass calculated for $C_8H_9NO_3$, 167.06; m/z found, 168 $[M+H]^+$.

Step 2:

[Chemical scheme showing 3-ethoxycarbonylpyridine N-oxide reacting to form Compound A, Major and Compound B, Minor]

To a solution of 3-ethoxycarbonylpyridine N-oxide in 330 mL of DCM were added trimethylsilyl cyanide (TMSCN) (11.0 g, 65.9 mmol, 1.0 eq) and dimethylcarbamoyl chloride (7.1 g, 65.9 mmol, 1.0 eq) and the reaction mixture was stirred at rt for 2 days. Then 10% $K_2CO_3$ was slowly added to make the reaction mixture basic. Organic layer was separated, dried and evaporated to provide the crude, which was purified by column chromatography to provide compounds A (5.7 g) and B (3.5 g).

Steps 3 and 4:

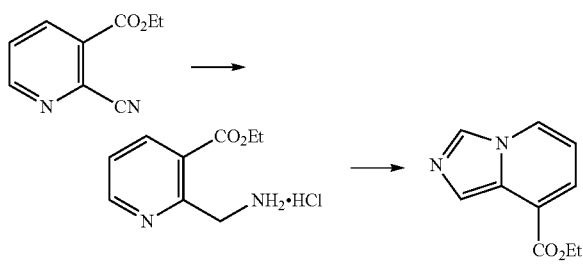

To a solution of ethyl 2-cyano-3-pyridinecarboxylate (2.5 g) and conc. HCl (5 mL) in 150 mL ethanol was added 10% Pd/C (wet, 250 mg) and the reaction mixture was hydrogenated using a hydrogen balloon and stirred for 12 h. The reaction was filtered through celite and ethanol was evaporated to give ethyl 2-(aminomethyl)-3-pyridinecarboxylate HCl as a white solid which was used in the next step without further purification.

A mixture of 44.8 mL of acetic anhydride and 19.2 mL of formic acid was heated in a 50-60° C. oil bath temperature for 3 h and then cooled to rt to give formic-acetic anhydride, which was then slowly added to the solid ethyl 2-(aminomethyl)-3-pyridinecarboxylate HCl and then stirred at rt for 8 h. Excess reagent was evaporated to give a residue, which was neutralized by very slow addition of sat. NaHCO$_3$ solution. Solution was extracted with DCM, dried and evaporated to provide ethyl imidazo[1,5-a]pyridine-8-carboxylate as a yellow solid (crude weight 2.7 g). MS: exact mass calculated for $C_{10}H_{10}N_2O_2$, 190.07; m/z found, 191 [M+H]$^+$.

Steps 5 and 6:

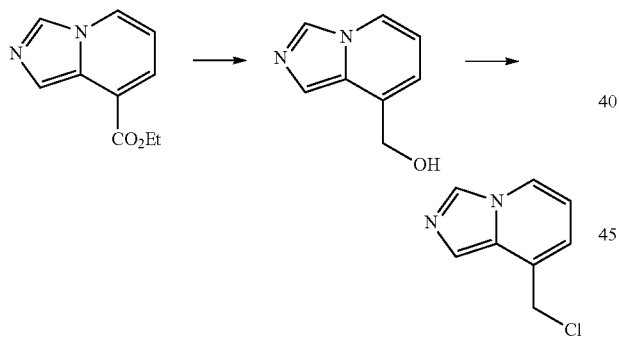

To a cold solution of lithium aluminum hydride (1.62 g, 42.4 mmol, 4.0 eq) in THF (50 mL) was added the crude ethyl imidazo[1,5-a]pyridine-8-carboxylate (2.7 g, 14.2 mmol, 1.0 eq) and the reaction mixture was heated at reflux for 2 h. The reaction was cooled and water (1.7 mL), 15% NaOH (1.7 mL) and water (5.1 mL) were slowly added. Solution was diluted with excess EtOAc and stirred at rt for 30 min. The solution was filtered and the solid was washed with ethyl acetate. Organic layers were combined, dried and solvent was removed to give crude imidazo[1,5-a]pyridine-8-methanol, which was purified by column chromatography (EtOAc/Hexane). MS: exact mass calculated for $C_8H_8N_2O$, 148.06; m/z found, 149 [M+H]$^+$.

To a solution of imidazo[1,5-a]pyridine-8-methanol (800 mg) in chloroform (50 mL) was slowly added thionyl chloride (10 mL) and the reaction mixture was stirred at rt for 8 h. Chloroform was removed and the residue was then taken in toluene and toluene was evaporated (3×) to give a solid, which was used in the next step without further purification. MS: exact mass calculated for $C_8H_7ClN_2$, 166.03; m/z found, 167 [M+H]$^+$.

Step 7:

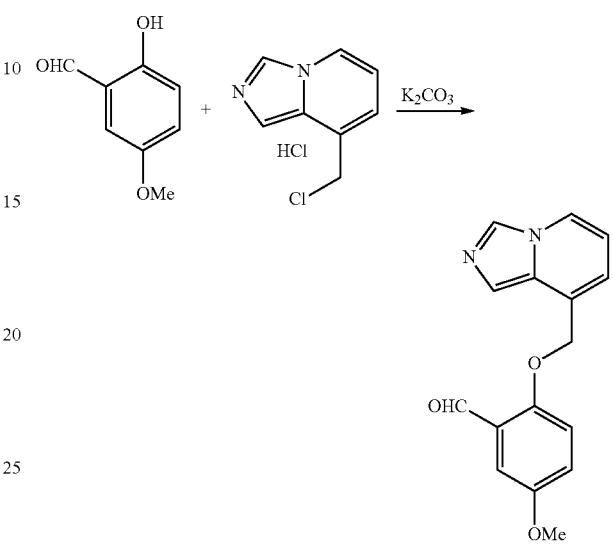

To a solution of chloride (1.25 mmol, 1.0 eq), and phenol (1.25 mmol, 1.0 eq) in DMF (10 mL) was added K$_2$CO$_3$ (3.0 eq) and the reaction mixture was heated at 80-90° C. for 5 h. Solvent was removed and the residue was purified by column chromatography (EtOAc/MeOH).NMR (400 MHz, CDCl$_3$): δ 3.82 (s, 3H), 5.45 (s, 2H), 6.58 (m, 1H), 6.81 (m, 1H), 7.03 (s, 1H), 7.12 (m, 1H), 7.35 (m, 1H), 7.50 (s, 1H), 7.95 (m, 1H), 8.18 (s, 1H), 10.58 (s, 1H); MS: exact mass calculated for $C_{16}H_{14}N_2O_3$, 282.10; m/z found, 283 [M+H]$^+$.

Example 2

Preparation of 2-(imidazo[1,5-a]pyridin-8-yl-methoxy)-4-methoxybenzaldehyde

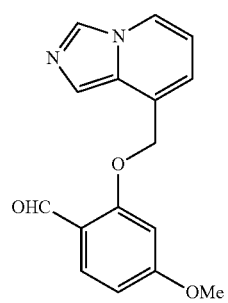 [SMILES: COc1ccc(C=O)c(OCc2cccn3cncc23)c1]

The title compound was prepared using 2-hydroxy-4-methoxybenzaldehyde in a similar manner as in Example 1. NMR (400 MHz, CDCl$_3$): δ 3.85 (s, 3H), 5.50 (s, 2H), 6.50-6.60 (m, 3H), 6.88 (s, 1H), 7.48 (s, 1H), 7.88 (m, 2H), 8.18 (s, 1H), 10.58 (s, 1H); MS: exact mass calculated for $C_{16}H_{14}N_2O_3$, 282.10; m/z found, 283 [M+H]$^+$.

Example 3

Preparation of 2-(imidazo[1,5-a]pyridin-6-yl-methoxy)-5-methoxybenzaldehyde

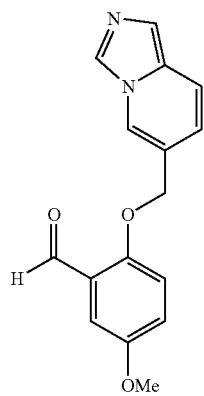 [SMILES: COc1ccc(OCc2ccc3cncn3c2)c(C=O)c1]

Steps 1 and 2:

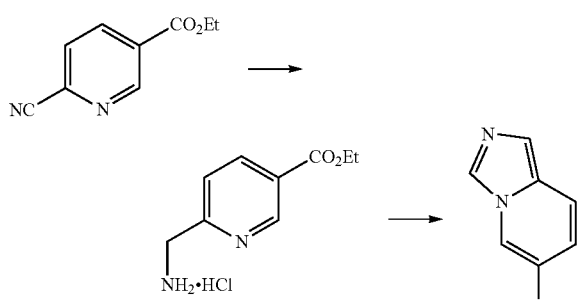

To a solution of ethyl 6-cyano-3-pyridinecarboxylate (3.75 g) and conc. HCl (7.5 mL) in 225 mL ethanol was added 10% Pd/C (wet, 375 mg) and the reaction mixture was hydrogenated using hydrogen balloon and stirred for 12 h. Solution was filtered through celite and ethanol was evaporated to give ethyl 6-(aminomethyl)-3-pyridinecarboxylate HCl as a white solid, which was used in the next step without further purification.

A mixture of 67.2 mL of acetic anhydride and 28.8 mL of formic acid was heated at 50-60° C. oil bath temperature for 3 h and then cooled to rt to give formic-acetic anhydride, which was then slowly added into the solid ethyl 2-(aminomethyl)-3-pyridinecarboxylate HCl and then stirred at rt for 8 h. Excess reagent was evaporated to give a residue, which was neutralized by very slow addition of sat NaHCO$_3$ solution. Solution was extracted with DCM, dried and evaporated to provide imidazo[1,5-a]pyridine as a yellow solid. MS: exact mass calculated for $C_{10}H_{10}N_2O_2$, 190.07; m/z found, 191 [M+H]$^+$.

Steps 3 and 4:

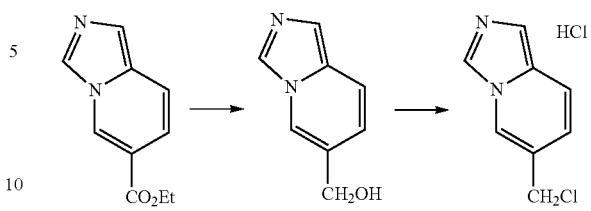

To a cold solution of lithium aluminum hydride (1.0 g, 26.3 mmol, 2.0 eq) in THF (40 mL) was added the crude ethyl imidazopyridine carboxylate (2.5 g, 13.2 mmol, 1.0 eq) and the reaction mixture was stirred at rt for 2 h. Reaction was cooled and water (1.7 mL), 15% NaOH (1.7 mL) and water (5.1 mL) were slowly added. Solution was next diluted with excess EtOAc and stirred at rt for 30 min. The solution was filtered and the solid was washed with ethyl acetate. Organic layers were combined, dried and solvent was removed to give crude imidazo[1,5-a]pyridine-8-methanol, which was purified by column chromatography (EtOAc/Hexane). MS: exact mass calculated for $C_8H_8N_2O$, 148.06; m/z found, 149 [M+H]$^+$.

To a solution of imidazopyridine methanol (700 mg, 4.7 mmol, 1.0 eq) in chloroform (20 mL) was slowly added thionyl chloride (1.7 mL) and the reaction mixture was stirred at rt for 8 h. Chloroform was removed and the residue was then taken up in toluene. Toluene was evaporated (3×) to give a solid (550 mg), which was used in the next step without further purification.

Step 5:

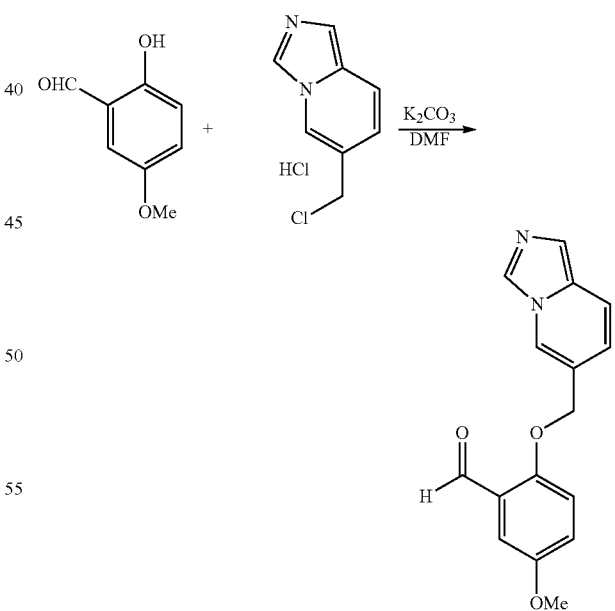

To a solution of chloride (1.25 mmol, 1.0 eq), and phenol (1.25 mmol, 1.0 eq) in DMF (10 mL) was added K$_2$CO$_3$ (3.0 eq) and the reaction mixture was heated at 80-90° C. for 5 h. Solvent was removed and the residue was purified by column chromatography (EtOAc/MeOH). MS: exact mass calculated for $C_{16}H_{14}N_2O_3$, 282.10; m/z found, 283 [M+H]$^+$.

Example 4

Preparation of 2-(imidazo[1,5-a]pyridin-6-yl-methoxy)-4-methoxybenzaldehyde

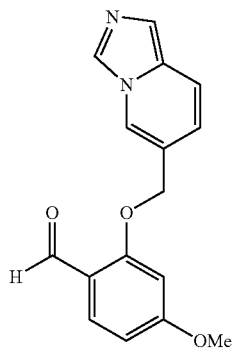 [SMILES: COc1ccc(C=O)c(OCc2ccc3cncn3c2)c1]

The title compound was prepared using 2-hydroxy-4-methoxybenzaldehyde in a similar manner as in Example 3.

Example 5

Preparation of methyl imidazo[1,2-a]pyridine-8-carboxylate

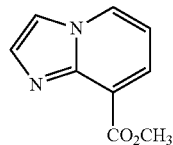

To a solution of methyl 2-amino-pyridine-3-carboxylate (5 g, 35 mmol, 1.0 eq) in ethanol (250 mL) was added NaHCO$_3$ (5.08 g) and chloroacetaldehyde in water (35 mL of 45% in water, 148 mmol, 4.5 eq). The reaction mixture was heated at reflux for 18 h. Solvent was removed and the residue was basified with Na$_2$CO$_3$ and then extracted with DCM. Organic layers were combined and evaporated to give a residue, which was purified by column to give the titled compound.

Example 6

Preparation of imidazo[1,2-a]pyridin-8-ylmethanol

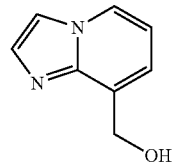 [SMILES: OCc1cccn2ccnc12]

To a cold solution of methyl imidazo[1,2-a]pyridine-8-carboxylate (5.55 g, 31.53 mmol, 1 eq) in THF (100 mL) was added LAH in ether (1 M solution in ether, 4 equiv.) and then stirred at rt for 6 h. The reaction mixture was cooled to 0° C. and quenched with water/15% NaOH/water. Reaction mixture was diluted with ethyl acetate and stirred at room temperature for 15 min and then filtered. The solid was washed with ethanol and the organic layers were combined, dried and evaporated to give the alcohol, which was purified by column chromatography to yield the desired product in 40% yield.

Example 7

Preparation of 8-(chloromethyl)imidazo[1,2-a]pyridine

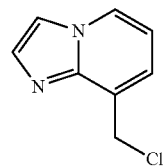 [SMILES: ClCc1cccn2ccnc12]

A mixture of imidazo[1,2-a]pyridin-8-ylmethanol (800 mg) and excess thionyl chloride was stirred at 70-80° C. for 8 h. Excess thionyl chloride was removed under vacuum. The residue was then diluted with toluene and evaporated. This procedure was repeated 3 times.

Example 8

Preparation of 2-(imidazo[1,2-a]pyridin-8-yl-methoxy)-5-methoxybenzaldehyde

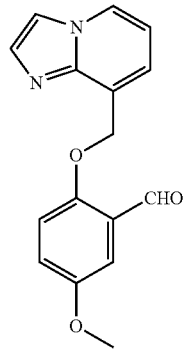 [SMILES: COc1ccc(OCc2cccn3ccnc23)c(C=O)c1]

To a solution of the crude 8-(chloromethyl)imidazo[1,2-a]pyridine (6.8 mmol, 1 eq) and 2-hydroxy-5-methoxybenzaldehyde (1.3 g, 8.1 mmol, 1.2 eq) in DMF (20 mL) was added potassium carbonate (2.8 g, 20.4 mmol, 3 eq) and the reaction mixture was heated at 85-90° C. for 5 h. DMF was removed under vacuum and the residue was taken in ethyl acetate and filtered. The solid was washed with additional ethyl acetate, and then dried and evaporated to give the crude, which was purified by column chromatography (EtOAc/Hexane) to yield the desired compound in 45% yield. NMR (400 MHz, CDCl$_3$): δ 3.80 (s, 3H), 5.60 (s, 2H), 6.85 (d, 1H), 7.12 (d, 2H), 7.36 (m, 2H), 7.66 (m, 2H), 8.14 (m, 1H), 10.58 (s, 1H); MS: exact mass calculated for $C_{16}H_{14}N_2O_3$, 282.10; m/z found, 283 [M+H]$^+$.

Example 9

Preparation of 2-(imidazo[1,2-a]pyridin-8-yl-methoxy)-4-methoxybenzaldehyde

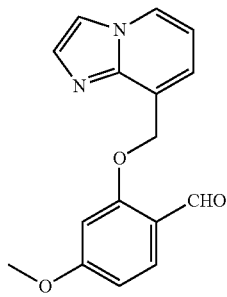 [SMILES: COc1ccc(C=O)c(OCc2cccn3ccnc23)c1]

The title compound was prepared using 2-hydroxy-4-methoxybenzaldehyde in a similar manner as in Example 3. NMR (400 MHz, CDCl$_3$): δ 3.88 (s, 3H), 5.65 (s, 2H), 6.58 (m, 1H), 6.68 (s, 1H), 6.88 (m, 1H), 7.42 (m, 1H), 7.66 (m, 2H), 7.83 (m, 1H), 8.14 (m, 1H), 10.45 (s, 1H); MS: exact mass calculated for $C_{16}H_{14}N_2O_3$, 282.10; m/z found, 283 [M+H]$^+$.

Example 10

Preparation of 5-methoxy-2-((1-methyl-1H-indazol-4-yl)methoxy)benzaldehyde (Compound 115)

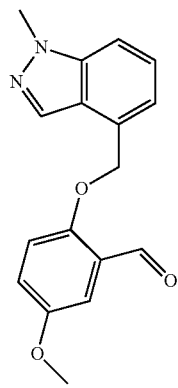 [SMILES: COc1ccc(OCc2cccc3c2cnn3C)c(C=O)c1]

Step 1:

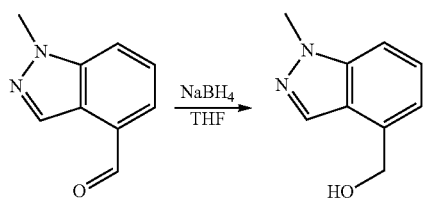

To a mixture of 1-methyl-1H-indazole-4-carbaldehyde (180 mg, 1.12 mol) in THF (10 mL) was added NaBH$_4$ (85 mg, 2.24 mmol) at rt. The reaction mixture was stirred at rt for 1 h, acidified to pH 3, and extracted with EtOAc. The combined organic layer was washed with saturated sodium bicarbonate solution and brine, dried over Na$_2$SO$_4$, filtered, and concentrated to give a crude solid (191 mg), which was used for next step without further purification.

Step 2:

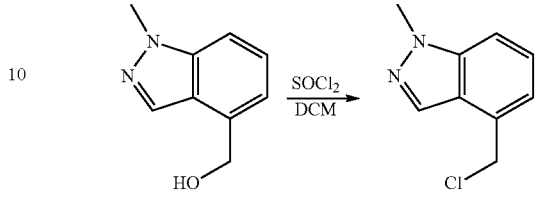

To (1-methyl-1H-indazol-4-yl)methanol (191 mg) in DCM (5 mL) was added SOCl$_2$ (2 mL) at rt. The reaction mixture was stirred at rt for 4 h and concentrated to dryness. The crude solid was suspended in toluene and concentrated to dryness. The process was repeated three times and dried under vacuum to give an off-white solid (210 mg), which was used for next step without further purification.

Step 3:

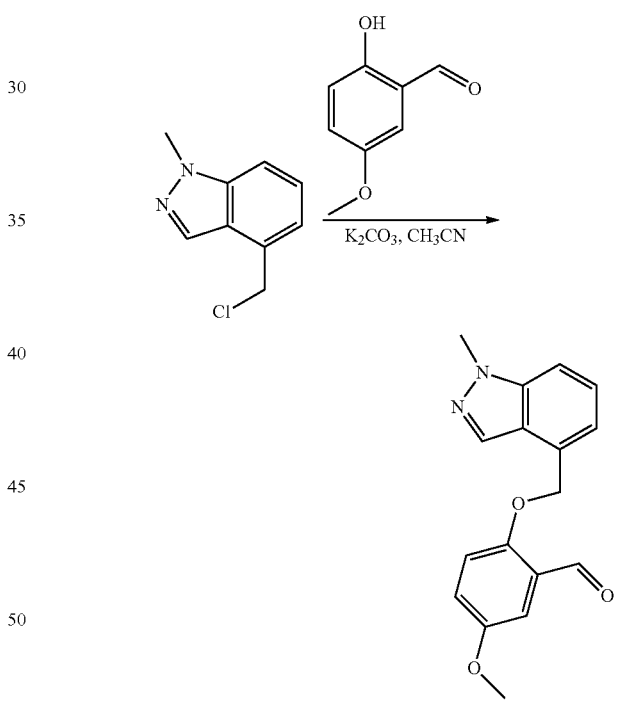

A mixture of 2-hydroxy-5-methoxybenzaldehyde (170 mg, 1.12 mmol), 4-(chloromethyl)-1-methyl-1H-indazole (1.12 mmol), and K$_2$CO$_3$ (618 mg, 4.48 mmol) was reflux in CH$_3$CN (20 mL) for 2 h. The mixture was filtered and the solid was washed with DCM. The filtrate was concentrated and purified on silica gel using a mixture of EtOAc and MeOH as eluent to give 5-methoxy-2-((1-methyl-1H-indazol-4-yl)methoxy)benzaldehyde (215 mg, 81% for three steps) as a white solid. $^1$H NMR (400 MHz; DMSO) δ=10.39 (s, 1H), 8.20 (d, 1H), 7.63 (d, 1H) 7.36-7.64 (m, 2H), 7.23-7.29 (m, 2H), 7.18 (d, 1H), 5.58 (s, 2H), 4.06 (s, 3H), 3.34 (s, 3H). LRMS (M+H$^+$) m/z 297.1.

Example 11

Preparation of 2-((1H-indazol-4-yl)methoxy)-5-methoxybenzaldehyde

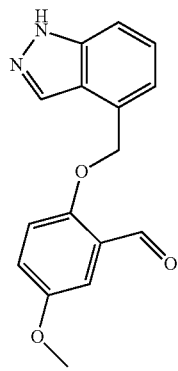 [SMILES: COc1ccc(OCc2cccc3[nH]ncc23)c(C=O)c1]

Step 1:

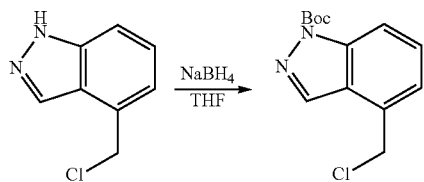

To a mixture of 4-(chloromethyl)-1H-indazole (1.0 g, 6.0 mol) in DCM (20 mL) was added (Boc)$_2$O (1.96 g, 9.0 mmol) and DMAP (dimethylamino pyridine 67.2 mg, 0.6 mmol) at rt. The reaction mixture was stirred at rt for 1 h, concentrated, and purified on silica gel to give tert-butyl 4-(chloromethyl)-1H-indazole-1-carboxylate (1.4 g, 88%) as an a colorless oil.

Step 2:

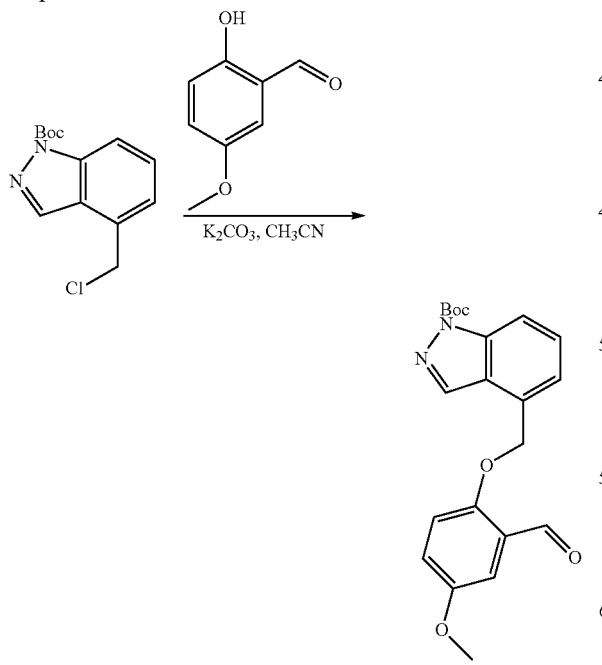

A mixture of 2-hydroxy-5-methoxybenzaldehyde (46 mg, 0.3 mmol), tert-butyl 4-(chloromethyl)-1H-indazole-1-carboxylate (80 mg, 0.3 mmol), and K$_2$CO$_3$ (166 mg, 1.2 mmol) in DMF (1.0 mL) was heated at 80° C. for 2 h. The mixture was filtered and the solid was washed with DCM. The filtrate was concentrated and purified on silica gel using a mixture of EtOAc and hexanes as eluent to give tert-butyl 4-((2-formyl-4-methoxyphenoxy)methyl)-1H-indazole-1-carboxylate (88 mg, 77%) as a colorless oil.

Step 3:

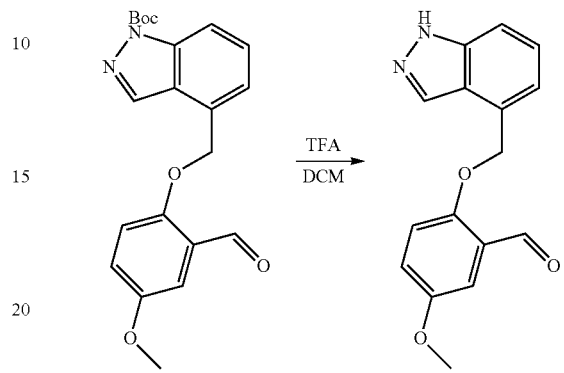

To tert-butyl 4-((2-formyl-4-methoxyphenoxy)methyl)-1H-indazole-1-carboxylate (88 mg, 0.23 mmol) in DCM (5.0 mL) was added TFA (2.0 mL). The mixture was stirred at rt for 2 h and concentrated. The crude was purified on silica gel using a mixture of EtOAc and hexanes as eluent to give 2-((1H-indazol-4-yl)methoxy)-5-methoxybenzaldehyde (50 mg, 77%) as a white solid. $^1$H NMR (400 MHz; CDCl$_3$) δ=10.53 (s, 1H), 8.23 (s, 1H), 7.54 (d, 1H) 7.43 (t, 1H), 7.38 (d, 1H), 7.25 (d, 1H), 7.08-7.15 (m, 2H), 5.51 (s, 2H), 3.82 (s, 3H). LRMS (M+H$^+$) m/z 283.1.

Example 12

Preparation of 3-(imidazo[1,2-a]pyridin-8-ylmethyl)-1,3-dihydroisobenzofuran-1-ol

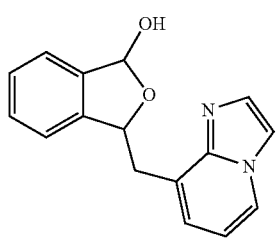 [SMILES: OC1OC(Cc2cccn3ccnc23)c2ccccc21]

Step 1:

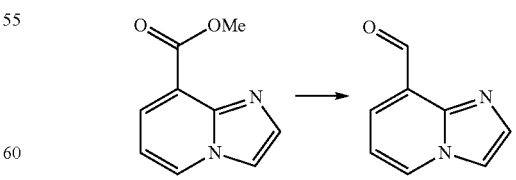

To a solution of methyl imidazo[1,2-a]pyridine-8-carboxylate (1.76 g, 10 mmol) in toluene was added DIBAL (1M/THF, 20 ml) at −78° C. dropwise. The mixture was stirred at −78° C. for 1 h, quenched with MeOH (2 mL) and saturated NH$_4$Cl solution (50 mL) and warmed up to rt. The mixture was continued to stir at rt for 1 h and diluted with DCM (60 mL). The aqueous layer was extracted with DCM (60 mL) twice. The combined organic layer was dried over MgSO4 and concentrate. The residue was purified on silica gel with 10% MeOH/DCM to give imidazo[1,2-a]pyridine-8-carbaldehyde (0.8 g, 55%). LRMS (M+H⁺) m/z 147.1.

Step 2:

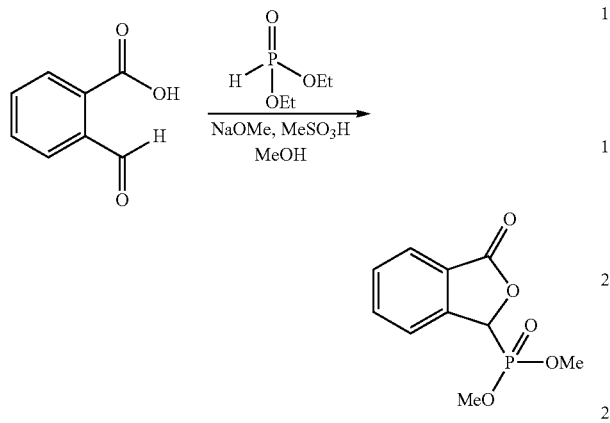

To a solution of sodium methoxide (5.4 M, 4.8 mL) in MeOH (20 mL) was added diethyl phosphite (3.31 g, 24 mmol) at 0° C. followed by addition of 2-formylbenzoic acid (3.0 g, 20 mmol) portion-wise over a period of 20 min. The resulting mixture was warmed up to rt and continued to stir for 2 h. Methanesulphonic acid (2.69 g, 28 mmol, 1.4 equiv.) was added to the above mixture over a period of 30 min. The reaction mixture was stirred for 30 min and concentrated to remove most of the MeOH. The residue was partitioned between DCM (100 mL) and water (50 mL). The aqueous layer was extracted DCM twice. The combined organic layer was dried over Na2SO4 and concentrated to give dimethyl 3-oxo-1,3-dihydroisobenzofuran-1-ylphosphonate (4.6 g, 90%). LRMS (M+H⁺) m/z 257.1.

Step 3:

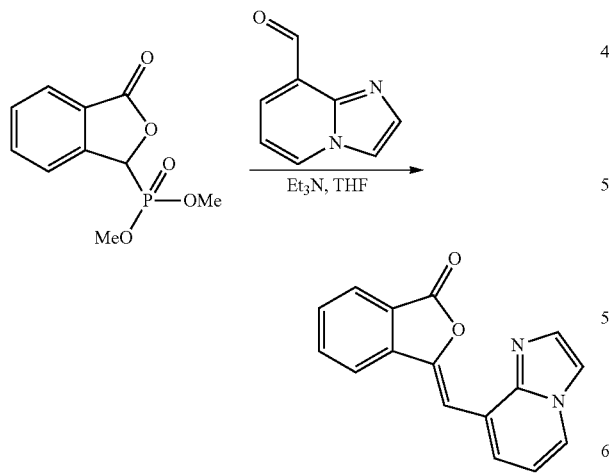

To a solution of dimethyl 3-oxo-1,3-dihydroisobenzofuran-1-ylphosphonate (610 mg, 2.4 mmol), imidazo[1,2-a]pyridine-8-carbaldehyde (350 mg, 2.4 mmol, 1 equiv.) in THF (5 mL) was added Et3N (0.33 mL 2.4 mmol). The mixture was stirred at rt for 48 h. The precipitation was filtered off and washed with EtOAc. The filtrate was concentrated to give 3-(imidazo[1,2-a]pyridin-8-ylmethylene)isobenzofuran-1 (3H)-one (400 mg, 64%) as a yellow solid. Small crude sample (~20 mg) was purified on RP-HPLC with CH3CN and water as eluent to separated the E/Z isomers (10 mg, 7 mg). ¹H NMR (400 MHz, CD3OD) Z-form: δ=8.52 (d, 1H), 7.95-7.91 (m, 2H), 7.62-7.54 (m, 4H), 7.52-7.48 (m, 1H), 7.09 (s, 1H), 7.04 (t, 1H) E-form: δ=8.38 (d, 1H), 8.15 (d, H), 8.05 (d, 1H), 7.95 (d, 1H), 7.90-7.84 (m, 2H), 7.67 (t, 1H), 7.64 (s, 1H), 7.33 (s, 1H), δ 7.05 (t, 1H). LRMS (M+H⁺) m/z 263.1

Step 4:

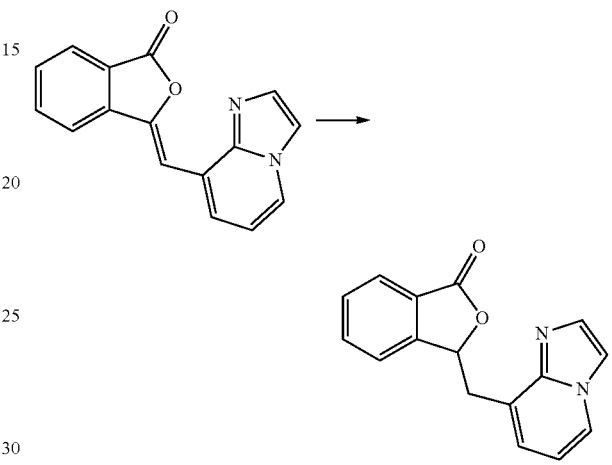

To a solution of 3-(imidazo[1,2-a]pyridin-8-ylmethylene) isobenzofuran-1(3H)-one (180 mg, 0.69 mmol) in EtOAc (12 mL) was added 10% Pd/C (110 mg). The mixture was stirred under a hydrogen balloon overnight. The catalyst was filtered off and the filtrate was concentrated and purified on silica gel with 10% MeOH/DCM as eluent to give 3-(imidazo[1,2-a] pyridin-8-ylmethyl)isobenzofuran-1(3H)-one (140 mg, 78%). ¹H NMR (400 MHz, CD3OD) δ=8.37 (d, 1H), S 7.88 (s, 1H), 7.83 (d, 1H), 7.74-7.63 (m, 2H), 7.60-7.53 (m, 2H), δ 7.22 (d, 1H), 6.86 (t, 1H), 6.04 (dd, 1H), 3.76 (dd, 1H), 3.24 (dd, 1H). LRMS (M+H⁺) m/z 265.1

Step 5:

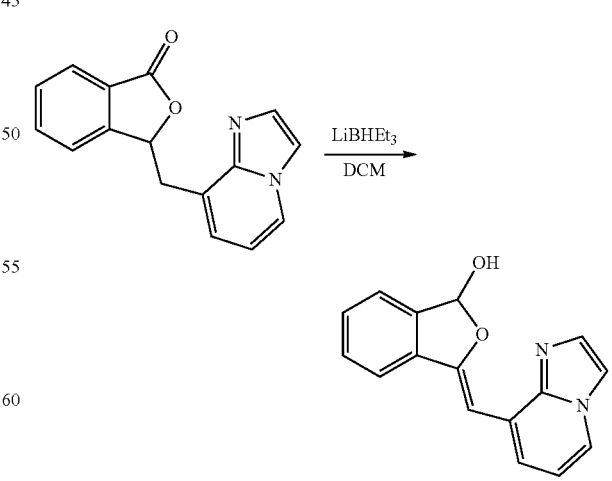

To a solution of 3-(imidazo[1,2-a]pyridin-8-ylmethyl) isobenzofuran-1(3H)-one (80 mg, 0.3 mmol) in DCM (6 mL) at −78° C., was added lithium triethyl borohydride (1M/THF, 0.3 mL) dropwise. The reaction mixture was stirred at −78° C. for 30 min, diluted with DCM (\; 10 mL), and quenched with MeOH (1 mL) and 5% HCl (2 mL). The mixture was warmed up to rt and stirred for 1 h. The solvents were removed and the residue was purified on RP-HPLC using CH₃CN and water as eluent to give 3-(imidazo[1,2-a]pyridin-8-ylmethyl)-1,3-dihydroisobenzofuran-1-ol (20 mg, 25%). ¹H NMR (400 MHz, CD₃OD) δ=8.56 (t, 1H), 8.97 (d, 1H), 7.74 (s, 1H), 7.45-7.32 (m, 5H), 7.07-7.00 (m, 1H), 6.38-6.30 (m, 1H), 5.84-5.80 (m, 0.5H), 5.56 (dd, 0.5H), 3.69 (t, 0.5H), 3.65 (t, 0.5H), 3.26 (dd, 0.5H), 3.13 (dd, 0.5H). LRMS (M+H⁺) m/z 267.1.

Example 13

Preparation of 5-(imidazo[1,2-a]pyridin-8-yl-methoxy)-2-methoxyibenzaldehyde

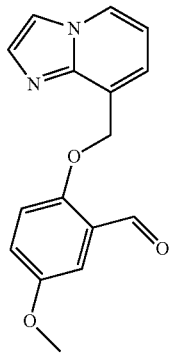 [SMILES: COc1ccc(OCc2cccn3ccnc23)c(C=O)c1]

Step 1:

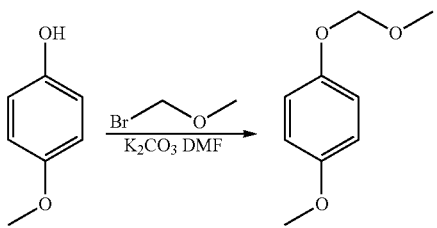

To a mixture of 6-methoxyphen-3-ol (25 g, 0.2 mol) and K₂CO₃ (82.8 g, 0.6 mol) in DMF (250 mL) is added bromomethyl methyl ether (30 g, 0.24 mmol) slowly at rt for a period of 1 h. The reaction mixture is filtered and the filtrate is concentrated. The residue is purified on silica gel with 25% EtOAc/hexanesas eluent to give 2-methoxy-5-(methoxymethoxy)benzene.

Step 2:

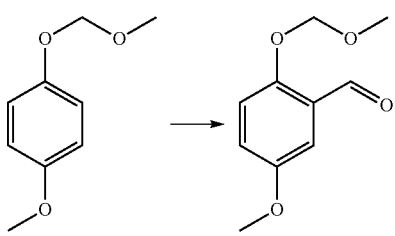

To a solution of 2-methoxy-5-(methoxymethoxy)benzene (20 g, 0.1 2 mol) in THF is added diisopropylamine (0.24 g, 2.4 mmol). The solution is cooled to −40° C. followed by addition of MeLi (3M/THF, 72 mL, 0.216 mol) slowly. The resulting mixture is warmed to 0° C., stirred at 0° C. for 3 h, cooled back down to −40° C. and added N-formylpiperidine (24 mL, 0.216 mol). After stirring at −40° C. for 2 h, the mixture is quenched with a mixed solution of HCl (37%, 120 mL) and THF (250 mL). The temperature is then raised to rt and diluted with water (200 mL) and EtOAc (200 mL). The pH of the mixture is adjusted to 8-9 with solid K₂CO₃ and extracted with EtOAc (300 mL) twice. The organic layer is combined, dried over Na₂SO₄, and concentrated. The residue is purified on silica gel with 25% EtOAc/hexanes as eluent to give 2-methoxy-5-(methoxymethoxy)benzaldehyde.

Step 3:

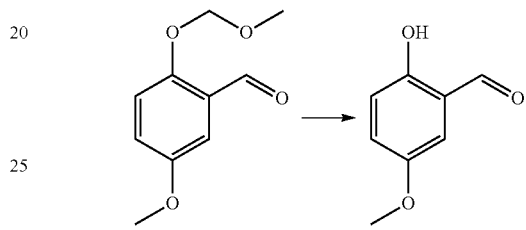

To a solution of 2-methoxy-5-(methoxymethoxy)benzaldehyde (10 g, 0.05 mol) in THF (100 mL) was added 3 N HCl (150 mL). The reaction was stirred at 50° C. for 30 min, cooled to rt, and diluted with water (100 mL). The mixture was neutralized to pH 7-8 and extracted with EtOAc (200 mL) three times. The organic layer was dried over Na₂SO₄ and concentrated to give 5-hydroxy-2-methoxybenzaldehyde.

Step 4:

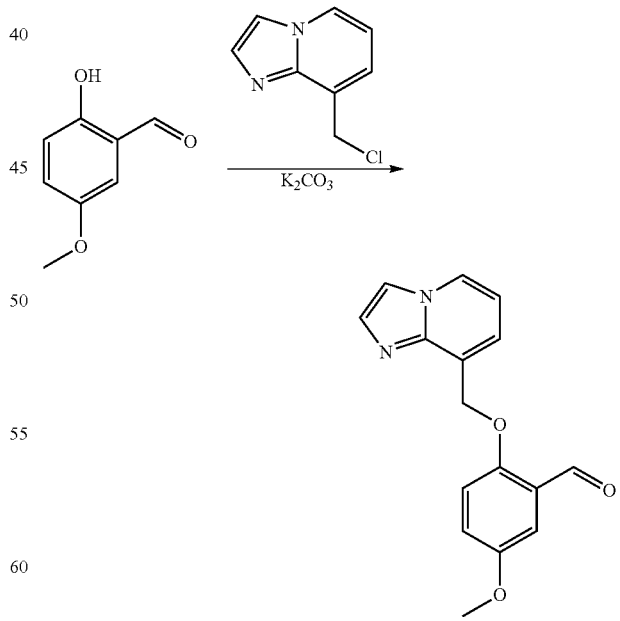

A mixture of 5-hydroxy-2-methoxybenzaldehyde (723.6 mg, 4.7 mmol), 8-(chloromethyl)-imidazol[1,2-a]pyridine (785 mg, 4.7 mmol), and K₂CO₃ (1.9 g, 14.1 mmol) in DMF (20 mL) was heated at microwave reactor at 125° C. for 15 min. The mixture was filtered and concentrated. The residue was purified on silica gel (50-100% EtOAc in hexanes) to give 5-(imidazo[1,2-a]pyridin-8-ylmethoxy)-2-methoxybenzaldehyde.

The compounds Examples 14-16 were prepared according to the procedure described in Example 13.

Example 14

Preparation of 2-(imidazo[1,2-a]pyridin-2-yl-methoxy)-5-methoxybenzaldehyde (Compound 5.)

$^1$H NMR (400 MHz, DMSO) δ 10.39 (s, 1H), 8.53 (d, J=6.8 Hz, 1H), 8.06 (s, 1H), 7.54 (d, J=9.1 Hz, 1H), 7.42 (d, J=9.1 Hz, 1H), 7.29-7.22 (m, 2H), 7.17 (d, J=3.3 Hz, 1H), 6.90 (t, J=6.8 Hz, 1H), 5.35 (s, 2H), 3.76 (s, 3H).

Example 15

Preparation of 5-methoxy-2-(quinolin-5-ylmethoxy)benzaldehyde (Compound 10)

$^1$H NMR (400 MHz, CDCl$_3$) δ 9.09 (s, 1H), 7.73 (dd, J=4.0, 1.3 Hz, 1H), 7.19 (d, J=8.4 Hz, 1H), 6.92 (d, J=8.4 Hz, 1H), 6.48 (t, J=8.4 Hz, 1H), 6.40 (d, J=6.9 Hz, 1H), 6.24 (dd, J=8.5, 4.2 Hz, 1H), 6.10 (d, J=2.6 Hz, 1H), 5.95-5.85 (m, 2H), 4.32 (s, 2H), 2.56 (s, 3H).

Example 16

Preparation of 5-methoxy-2-((8-methylimidazo[1,2-a]pyridin-2-yl)methoxy)benzaldehyde (Compound 24)

$^1$H NMR (400 MHz, CD$_3$CN) δ 10.32 (s, 1H), 8.01 (d, J=6.8 Hz, 1H), 7.68 (s, 1H), 7.19 (d, J=9.0 Hz, 1H), 7.13 (d, J=3.2 Hz, 1H), 7.08 (dd, J=9.0, 3.3 Hz, 1H), 6.90 (td, J=6.8, 1.2H 1H), 6.62 (t, J=6.s Hz, 1H), 5.21 (s, 2H), 3.67 (s, 3H), 2.39 (s, 3H).

Example 17

Preparation of 2-hydroxy-6-((2-(1-isopropyl-1H-pyrazol-5-yl)pyridin-3-yl)methoxy)benzaldehyde (Compound 43)

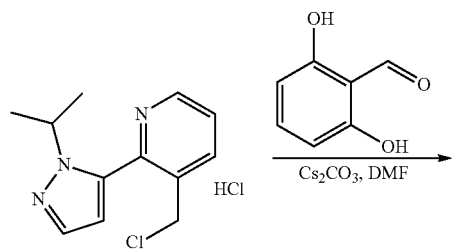

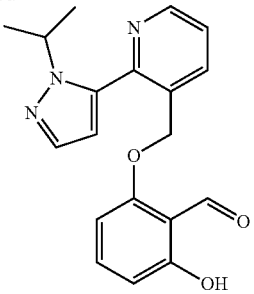

A mixture of 2,6-dihydroxybenzaldehyde (1.96 g, 14.2 mmol, 2 eq.) and Cs$_2$CO$_3$ (7.5 g, 21.3 mmol, 3 eq.) in DMF (180 mL) was stirred at rt for 30 min. To this mixture was added 3-(chloromethyl)-2-(1-isopropyl-1H-pyrazol-5-yl)pyridine hydrochloride (1.93 g, 7.1 mmol, 1 eq.) at rt. The mixture was continued to stir at rt O/N, filtered, concentrated and purified on silica gel using a mixture of EtOAc and hexanes as eluent to give 2-hydroxy-6-((2-(1-isopropyl-1H-pyrazol-5-yl)pyridin-3-yl)methoxy)benzaldehyde (920 mg, 37%) as a pale yellow oil. $^1$H NMR (400 MHz, CDCl$_3$) δ 11.96 (s, 1H), 10.40 (s, 1H), 8.77 (dd, J=4.8, 1.5 Hz, 1H), 8.00 (d, J=7.8 Hz, 1H), 7.63 (d, J=1.8 Hz, 1H), 7.49-7.34 (m, 2H), 6.59 (d, J=8.5 Hz, 1H), 6.37 (d, J=1.8 Hz, 1H), 6.29 (d, J=8.2 Hz, 1H), 5.10 (s, 2H), 4.67 (sep, J=6.7 Hz, 1H), 1.50 (d, J=6.6 Hz, 6H). LRMS (M+H$^+$) m/z 338.1

Example 18

Preparation of 2-hydroxy-6-((2-(1-isopropyl-1H-pyrazol-5-yl)pyridin-3-yl)methoxy)benzaldehyde (Compound 43)

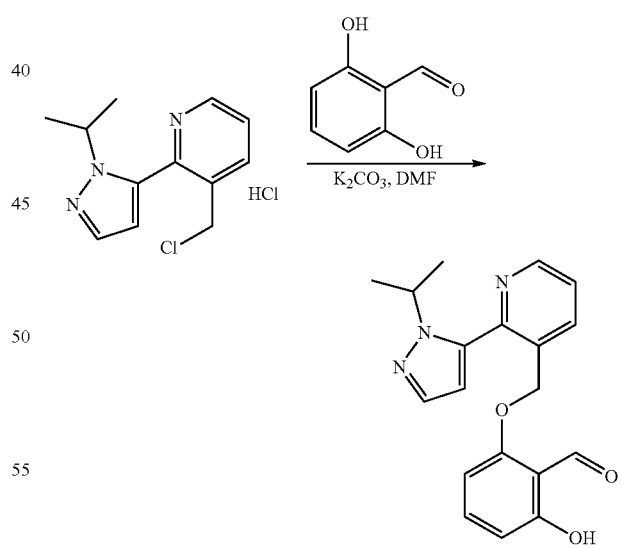

A mixture of 2,6-dihydroxybenzaldehyde (1.58 g, 11.47 mmol, 2 eq.) and K$_2$CO$_3$ (2.4 g, 17.22 mmol, 3 eq.) in DMF (150 mL) was stirred at rt for 10 min. To this mixture was added 3-(chloromethyl)-2-(1-isopropyl-1H-pyrazol-5-yl)pyridine hydrochloride (1.56 g, 5.74 mmol, 1 eq.) at rt. The mixture was heated at 50° C. for 2 h, filtered, concentrated and purified on silica gel using a mixture of EtOAc and hexanes as eluent to give 2-hydroxy-6-((2-(1-isopropyl-1H-pyrazol-5- yl)pyridin-3-yl)methoxy)benzaldehyde (1.71 g, 88%) as a pale yellow solid. $^1$H NMR (400 MHz, CDCl$_3$) δ 11.96 (s, 1H), 10.40 (s, 1H), 8.77 (dd, J=4.8, 1.5 Hz, 1H), 8.00 (d, J=7.8 Hz, 1H), 7.63 (d, J=1.8 Hz, 1H), 7.49-7.34 (m, 2H), 6.59 (d, J=8.5 Hz, 1H), 6.37 (d, J=1.8 Hz, 1H), 6.29 (d, J=8.2 Hz, 1H), 5.10 (s, 2H), 4.67 (sep, J=6.7 Hz, 1H), 1.50 (d, J=6.6 Hz, 6H). LRMS (M+H$^+$) m/z 338.1

Example 19

Preparation of 5-((2-(2H-tetrazol-5-yl)pyridin-3-yl)methoxy)-2-methoxybenzaldehyde Step 1:

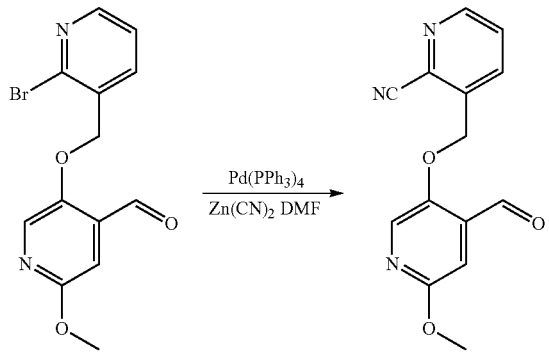 [SMILES: COc1cc(C=O)c(OCc2cccnc2Br)cn1 ; COc1cc(C=O)c(OCc2cccnc2C#N)cn1 ; "Pd(PPh3)4"]

To a mixture of 5-((2-bromopyridin-3-yl)methoxy)-2-methoxybenzaldehyde (100 mg, 0.31 mmol, 1 equiv), Zn(CN)$_2$ (71 mg, 0.62 mmol, 2.0 equiv), Pd(PPh$_3$)$_4$ (72 mg, 0.06 mmol, 0.2 equiv) in a 5 mL microwave tube is added DMF (2 mL). The mixture is heated 15 min at 125° C. in a microwave reactor. The solid is filtered off and the filtrate is concentrated to dryness. The crude was purified on silica gel using a mixture of EtOAc and hexanes as eluent to give 3-((4-formyl-6-methoxyphen-3-yloxy)methyl)picolinonitrile.

Step 2:

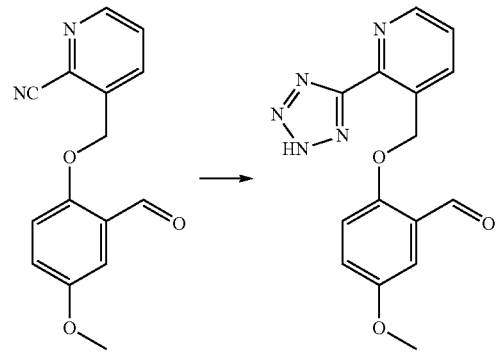 [SMILES: COc1ccc(OCc2cccnc2C#N)c(C=O)c1 ; COc1ccc(OCc2cccnc2-c2nn[nH]n2)c(C=O)c1]

To TEA hydrochloride salt (123 mg, 0.89 mmol, 4 equiv.) and 3-((4-formyl-6-methoxyphen-3-yloxy)methyl)picolinonitrile (70 mg, 0.26 mmol, 1 equiv.) in chlorobenzene (5.0 mL) is added NaN$_3$ (48 mg, 0.89 mmol, 4 equiv.) at rt. The mixture is heated to 110° C. for 2 h, cooled to rt, and added water (5.0 mL). The precipitate is filtered and washed with EtOAc and water and dried under high vacuo to give 5-((2-(2H-tetrazol-5-yl)phen-3-yl)methoxy)-2-methoxyisocotinaldehyde.

The compounds in Examples 20 and 21 were prepared according to the procedure described in Example 19.

Example 20

Preparation of 2-((3-(2H-tetrazol-5-yl)benzyl)oxy)-6-hydroxybenzaldehyde (Compound 44)

$^1$H NMR (400 MHz, CD$_3$CN) δ 11.95 (s, 1H), 10.45 (s, 1H), 8.17 (s, 1H), 8.05 (d, J=7.7 Hz, 1H), 7.69 (d, J=7.8 Hz, 1H), 7.62 (t, J=7.7 Hz, 1H), 7.49 (t, J=8.4 Hz, 1H), 6.62 (d, J=8.3 Hz, 1H), 6.54 (d, J=8.5 Hz, 1H), 5.30 (s, 2H).

Example 21

Preparation of 2-(4-(2H-tetrazol-5-yl)benzyl)oxy)-6-hydroxybenzaldehyde (Compound 45)

$^1$H NMR (400 MHz, DMSO) δ 11.77 (s, 1H), 10.40 (s, 1H), 8.06 (d, J=8.2 Hz, 2H), 7.69 (d, J=8.0 Hz, 2H), 7.54 (t, J=8.4 Hz, 1H), 6.73 (d, J=8.4 Hz, 1H), 6.56 (d, J=8.5 Hz, 1H), 5.33 (s, 2H).

Example 22

Preparation of 5-((4-formyl-6-methoxyphen-3-yloxy)methyl)nicotinic acid

Step 1:

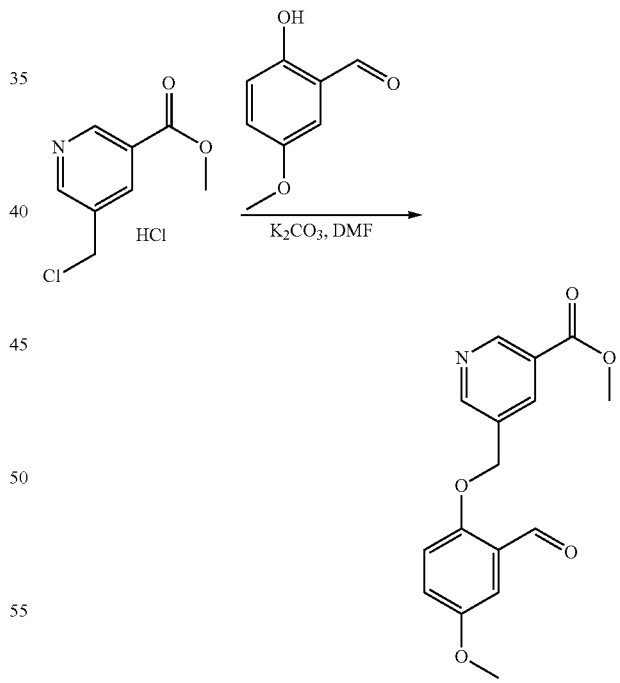

A mixture of 5-hydroxy-2-methoxybenzaldehyde (352 mg, 2.29 mmol, 1 eq.), methyl 5-(chloromethyl)nicotinate hydrochloride (506 mg, 2.29 mmol, 1 eq.), and K$_2$CO$_3$ (1.26 g, 9.16 mmol, 4 eq.) in DMF (8.0 mL) is heated at 60° C. for 3 h. The mixture is cooled and added into water (50 mL) dropwise. The precipitate is filtered, washed with water, and dried to give methyl 5-((4-formyl-6-methoxyphen-3-yloxy)methyl)nicotinate.

Step 2:

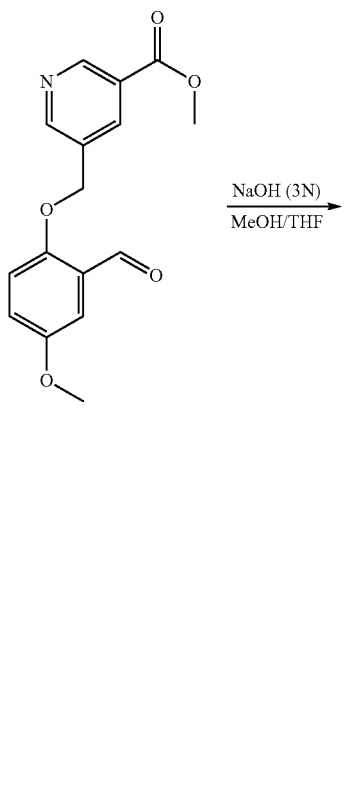

To 5-((4-formyl-6-methoxyphen-3-yloxy)methyl)nicotinate (96 mg, 0.32 mmol, 1 eq.) in a mixture of MeOH/THF (1/3, 8.0 mL) is added NaOH (3 N, 1.7 mL, 5.1 mmol, 16 eq.). The mixture is stirred at rt for 2 h, acidified to pH 3, extracted with EtOAc (3×20 mL). The combined organic layers are dried over Na$_2$SO$_4$ and concentrated to give 5-((4-formyl-6-methoxypyridin-3-yloxy)methyl)nicotinic acid.

The compounds in Examples 23-25 were prepared according to the procedure described in Example 22.

Example 23

Preparation of methyl 4-((2-formylphenoxy)methyl)benzoate (Compound 46)

$^1$H NMR (400 MHz, CDCl$_3$) δ 10.51 (s, 1H), 8.01 (d, J=8.3 Hz, 2H), 7.81 (dd, J=7.7, 1.8 Hz, 1H), 7.51-7.40 (m, 3H), 7.00 (t, J=7.5 Hz, 1H), 6.94 (d, J=8.4 Hz, 1H), 5.19 (s, 2H), 3.86 (s, 3H).

Example 24

Preparation of 4-((2-formylphenoxy)methyl)benzoic acid (Compound 47)

$^1$H NMR (400 MHz, CDCl$_3$) δ 10.52 (s, 1H), 8.09 (d, J=8.2 Hz, 2H), 7.81 (dd, J=7.7, 1.6 Hz, 1H), 7.53-7.43 (m, 3H), 7.01 (t, J=7.5 Hz, 1H), 6.95 (d, J=8.4 Hz, 1H), 5.21 (s, 2H).

Example 25

Preparation of methyl 3-((2-formylphenoxy)methyl)benzoate (Compound 48)

$^1$H NMR (400 MHz, CDCl$_3$) δ 10.58 (s, 1H), 8.14 (s, 1H), 8.06 (d, J=7.8 Hz, 1H), 7.90 (dd, J=7.7, 1.8 Hz, 1H), 7.69 (d, J=7.7 Hz, 1H), 7.60-7.48 (m, 2H), 7.08 (dd, J=14.4, 7.9 Hz, 2H), 5.26 (s, 2H), 3.96 (s, 3H).

Example 26

Preparation of 5-hydroxy-2-methoxybenzaldehyde

Step 1:

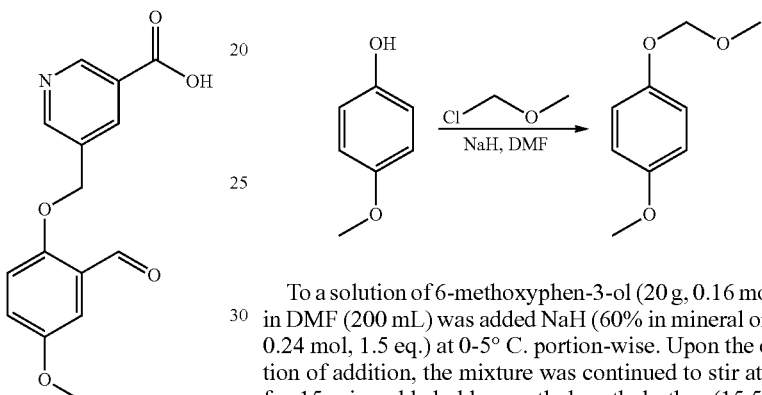

To a solution of 6-methoxyphen-3-ol (20 g, 0.16 mol, 1 eq.) in DMF (200 mL) was added NaH (60% in mineral oil; 9.6 g, 0.24 mol, 1.5 eq.) at 0-5° C. portion-wise. Upon the completion of addition, the mixture was continued to stir at 0-5° C. for 15 min, added chloromethyl methyl ether (15.5 g, 0.19 mol, 1.2 eq.), stirred at 0-5° C. for another 20 min, and quenched with NH$_4$C$_{(sat.)}$ solution. The aqueous layer was extracted with EtOAc (3×100 mL) and the combined organic layers were washed with water and brine, dried over Na$_2$SO$_4$, concentrated, and purified on silica gel using 25% EtOAc/hexanes as eluent to give 2-methoxy-5-(methoxymethoxy)benzene (24.1 g, 89.3%) as a colorless oil.

Step 2:

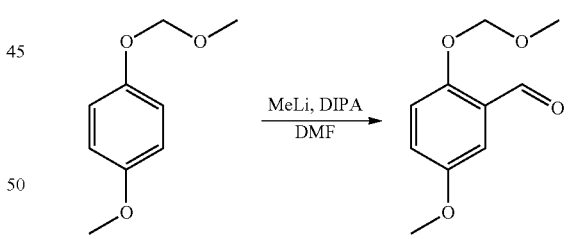

To a mixture of 2-methoxy-5-(methoxymethoxy)benzene (30 g, 0.178 mol, 1 eq.) and diisopropylamine (507 uL, 3.6 mmol, 0.02 eq.) in THF (500 mL) was added methyl lithium (1.6 M/THF, 200 mL, 0.32 mol, 1.8 eq.) at −40° C. Upon the completion of addition, the mixture was warmed to 0° C., continued to stir at 0° C. for 3 h, cooled back down to −40° C. and added DMF (24.7 mL, 0.32 mol, 1.8 eq.) slowly. The mixture was then stirred at −40° C. for 1 h, quenched with a mixture of HCl (12 N, 120 mL) and THF (280 mL), warmed to rt, and added water (200 mL). The pH of the mixture was adjusted to pH 8-9 with solid K$_2$CO$_3$. The aqueous layer was extracted with EtOAc (300 mL) twice. The combined organic layers were dried over Na$_2$SO$_4$ and concentrated to give 2-methoxy-5-(methoxymethoxy)benzaldehyde (33.5 g, 95.7%) as a brown solid, which was used for next step without further purification. ¹H NMR (400 MHz; CD₃OD) 7.90 (s, 1H), 6.92 (s, 1H), 5.64 (s, 1H), 5.20 (s, 2H), 3.84 (s, 3H), 3.48 (s, 3H). LRMS (M+H⁺) m/z 198.1

Step 3:

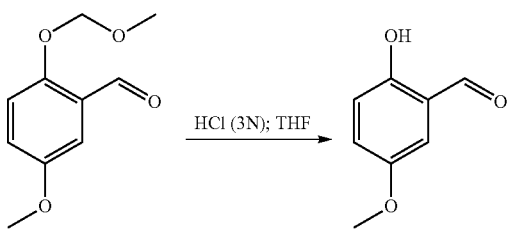

To a solution of 2-methoxy-5-(methoxymethoxy)benzaldehyde (33.5 g, 0.17 mol, 1 eq.) in THF (150 mL) was added HCl (3 N, 250 mL, 4.4 eq.). The reaction was stirred at 50° C. for 1 h, cooled to rt, and diluted with water (500 mL). The mixture was neutralized to pH 7-8 with solid K₂CO₃. The pale yellow solid was collected, washed with water, and dried to give 5-hydroxy-2-methoxybenzaldehyde (17.9 g, 74.6%) as a pale yellow solid. ¹H NMR (400 MHz; DMSO) δ=10.31 (s, 1H), 8.03 (s, 1H), 6.89 (s, 1H), 3.80 (s, 3H). LRMS (M+H⁺) m/z 154.0.

Example 27

Preparation of 5-((2-(1-isopropyl-1H-pyrazol-5-yl)pyridin-3-yl)methoxy)-2-methoxybenzaldehyde (Compound 150)

Step 1:

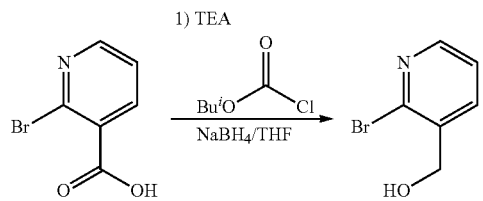

To a solution of 2-bromonicotinic acid (4.0 g, 20 mmol) and triethylamine (3.34 mL, 24 mmol, 1.2 eq.) in THF (100 mL) was added i-butyl chloroformate (3.12 mL, 24 mmol, 1.2 eq.) at 0° C. The mixture was stirred at 0° C. for 10 min and filtered. To this filtrate was added a suspension of NaBH₄ (1.52 g, 40 mmol, 2 eq.) in water (1.0 mL) at 0° C. The mixture was stirred for 30 min, added water (3 mL), continued to stir for 2 h, and concentrated to dryness. The crude was purified on silica gel using a mixture of ethylacetate and hexanes as eluent to give (2-bromopyridin-3-yl)methanol (3.4 g, 90%) as a white solid. LRMS (M+H⁺) m/z 188.0.

Step 2

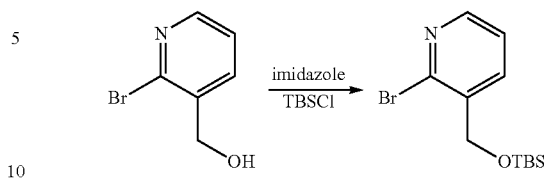

To a mixture of (2-bromopyridin-3-yl)methanol (20.0 g, 106.4 mmol, 1 eq.) and imidazole (14.5 g, 212.8 mmol, 2 eq.) in DMF (50.0 mL) was added TBSCl (19.2 g, 150.7 mmol, 1.2 eq.) at rt. The mixture was stirred at rt for 1 h and diluted with a mixture of water (100 mL) and EtOAc (300 mL). The organic layer was washed with NH₄Cl₍sat.₎ solution and brine, dried over Na₂SO₄, concentrated, and purified on silica gel using 10% EtOAc/hexanes as eluent to give 2-bromo-3-((tert-butyldimethylsilyloxy)methyl)pyridine (30.1 g, 94%) as a colorless oil. LRMS (M+H⁺) m/z 302.0.

Step 3

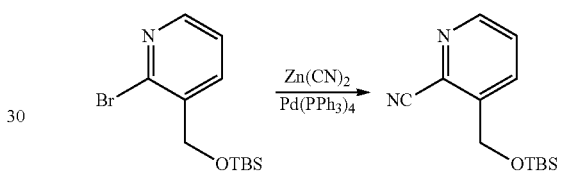

A mixture of 2-bromo-3-((tert-butyldimethylsilyloxy)methyl)pyridine (30.1 g, 100.0 mmol, 1 eq.) and Zn(CN)₂ (23.5 g, 200.0 mmol, 2.0 eq.) in DMF (100.0 mL) was purged with N₂ for 5 min and added Pd(PPh₃)₄ (5.78 g, 5.0 mmol, 0.05 eq.). The mixture was heated at 120° C. for 2 h under N₂, cooled, filtered, concentrated, and purified on silica gel using a mixture of EtOAc and hexanes as eluent to give 3-((tert-butyldimethylsilyloxy)methyl)picolinonitrile (20.4 g, 82%) as a colorless oil. LRMS (M+H⁺) m/z 249.1.

Step 4:

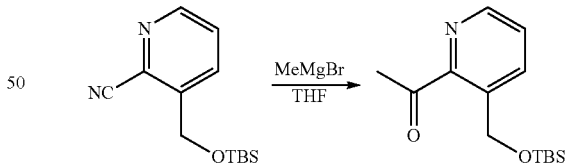

Methylmagnesium bromide (3M/ether, 41.0 mL, 123.4 mmol) was added to a stirred solution of 3-((tert-butyldimethylsilyloxy)methyl)picolinonitrile (20.4 g, 82.25 mmol) in THF (100.0 mL) at −78° C. The reaction mixture was warm to rt, quenched with aqueous citric acid solution, and extracted with EtOAc (50 mL) twice. The combined organic layers were washed with NaHCO₃ ₍sat₎ solution and brine, dried over Na₂SO₄, concentrated, and purified on silica gel using a mixture of EtOAc/hexanes as eluent to give 1-(3-((tert-butyldimethylsilyloxy)methyl)pyridin-2-yl)ethanone (12.9 g, 59%) as a colorless oil. LRMS (M+H⁺) m/z 266.2.

Step 5:

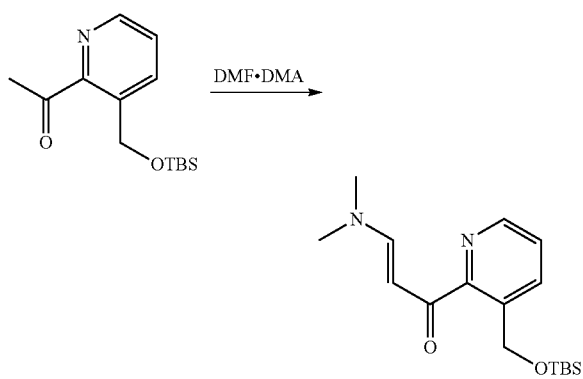

1-(3-((tert-butyldimethylsilyloxy)methyl)pyridin-2-yl)ethanone (10.8 g, 40.75 mmol) in dimethoxy-N,N-dimethylmethanamine (15.0 mL) was heated to reflux for 3 days. The mixture was concentrated and used for next step without further purification. LRMS (M+H$^+$) m/z 321.1.

Step 6:

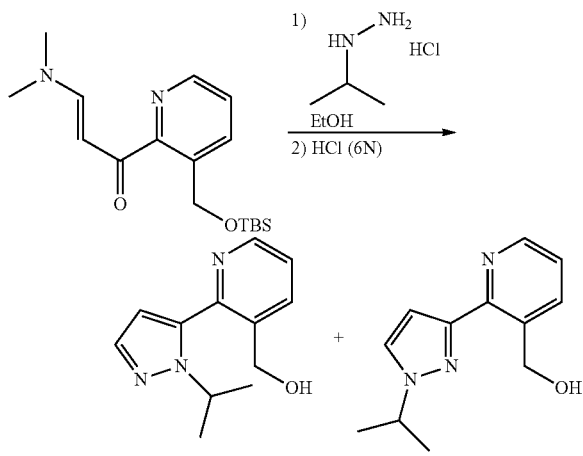

To (E)-1-(3-((tert-butyldimethylsilyloxy)methyl)pyridin-2-yl)-3-(dimethylamino)prop-2-en-1-one (crude, 1.03 g, 3.22 mmol, 1 eq.) in EtOH (10 mL) was added isopropylhydrazine hydrochloride (430 mg, 3.86 mmol, 1.2 eq.). The mixture was heated at 80° C. for 2 h, cooled, added HCl (6 N, 0.5 mL), and stirred O/N. The mixture was concentrated and diluted with EtOAc (80 mL) and NaHCO$_{3(sat)}$ (10 mL) solution. The layers were separated and the aqueous layer was extracted with EtOAc three times. The combined organic layers were dried over Na$_2$SO$_4$, concentrated, and purified on silica gel using EtOAc as eluent to give (2-(1-isopropyl-1H-pyrazol-5-yl)pyridin-3-yl)methanol (500 mg, 71%) and (2-(1-isopropyl-1H-pyrazol-3-yl)pyridin-5-yl)methanol (55 mg, 25%) as pale yellow oils. Data for 2-(1-isopropyl-1H-pyrazol-5-yl)pyridin-3-yl)methanol: $^1$H NMR (400 MHz, CDCl$_3$) δ 8.67 (dd, J=4.7, 1.5 Hz, 1H), 8.0 (d, J=7.8 Hz, 1H), 7.61 (d, J=1.8 Hz, 1H), 7.39 (dd, J=7.8, 4.8 Hz, 1H), 6.37 (d, J=1.8 Hz, 1H), 4.67 (s, 2H), 4.55 (sep, J=6.6 Hz 1H), 1.98-2.05 (br, 1H), 1.47 (d, J=6.6 Hz, 6H). LRMS (M+H$^+$) m/z 218.1 Data for (2-(1-isopropyl-1H-pyrazol-3-yl)pyridin-5-yl)methanol: $^1$H NMR (400 MHz, CDCl$_3$) δ 8.62 (dd, J=4.8, 1.6 Hz, 1H), 7.72 (d, J=7.6 Hz, 1H), 7.55 (d, J=2.4 Hz, 1H), 7.23 (dd, J=7.6, 4.8 Hz, 1H), 6.99 (dd, J=8.0, 6.5 Hz, 1H), 6.07 (t, J=7.6 Hz, 1H), 4.67 (d, J=7.6 Hz, 2H), 4.58 (sep, J=6.7 Hz, 1H), 1.60 (d, J=6.7 Hz, 1H). LRMS (M+H$^+$) m/z 218.1.

Step 7:

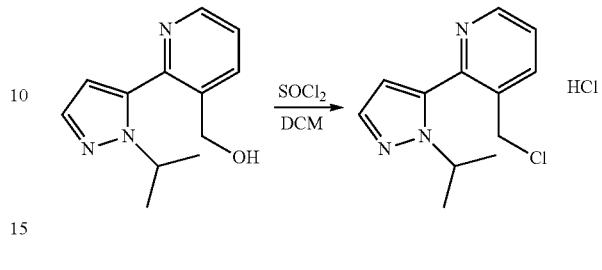

To (2-(1-iospropyl-1H-pyrazol-5-yl)pyridin-3-yl)methanol (560 mg, 2.58 mmol) in DCM (10 mL) was added SOCl$_2$ (3.0 mL) at rt. The reaction mixture was stirred at rt for 4 h and concentrated to dryness. The crude solid was suspended in toluene and concentrated to dryness. The process was repeated three times and dried under vacuum to give 3-(chloromethyl)-2-(1-isopropyl-1H-pyrazol-5-yl)pyridine hydrochloride (700 mg) as an off-white solid, which was used for next step without further purification.

Step 8:

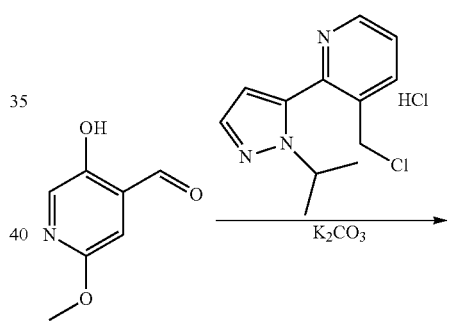

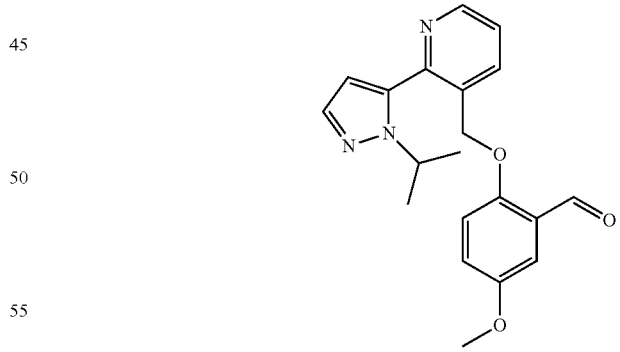

A mixture of 5-hydroxy-2-methoxybenzaldehyde (395 mg, 2.58 mmol, 1 eq.), 3-(chloromethyl)-2-(1-isopropyl-1H-pyrazol-5-yl)pyridine hydrochloride (700 mg, 2.58 mmol, 1 eq.), and K$_2$CO$_3$ (1.4 g, 10.32 mmol, 4 eq.) in DMF (10.0 mL) was heated at 70° C. for 2 h. The mixture was cooled, filtered, concentrated, and purified on silica gel using a mixture of EtOAc and hexanes as eluent to give 5-((2-(1-isopropyl-1H-pyrazol-5-yl)pyridin-3-yl)methoxy)-2-methoxybenzaldehyde (590 mg, 65%) as an off-white solid.

Step 9:

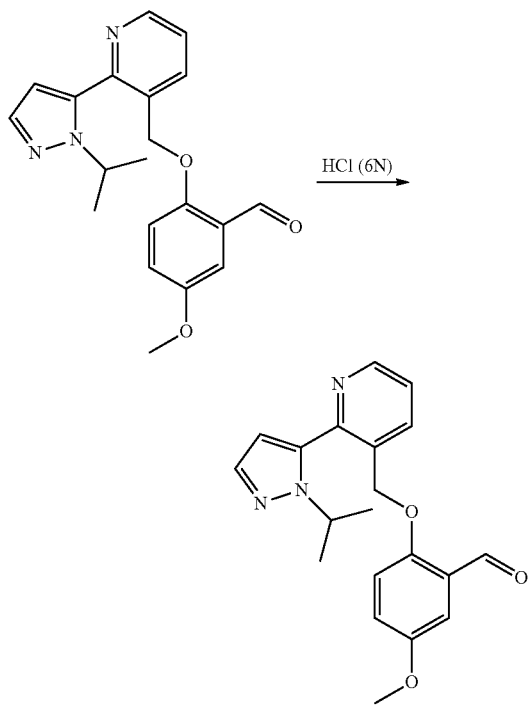

5-((2-(1-isopropyl-1H-pyrazol-5-yl)pyridin-3-yl)methoxy)-2-methoxybenzaldehyde (980 mg, 2.78 mmol, 1 eq.) in HCl (6 N, 9.2 mL, 20 eq.) solution was frozen at −78° C. The mixture was lyophilized O/N to give 5-((2-(1-isopropyl-1H-pyrazol-5-yl)pyridin-3-yl)methoxy)-2-methoxybenzaldehyde as a yellow solid.

Example 28

Preparation of 2-bromo-3-((2-(1-isopropyl-1H-pyrazol-5-yl)pyridin-3-yl)methoxy)benzaldehyde (Compound 49)

The title compound was prepared according to the procedure described in Example 27.

$^1$H NMR (400 MHz, CDCl$_3$) δ 10.46 (s, 2H), 8.77 (d, J=4.6 Hz, 2H), 8.22 (d, J=7.9 Hz, 2H), 7.64 (s, 2H), 7.59 (d, J=7.8 Hz, 2H), 7.47 (dd, J=8.0, 4.8 Hz, 2H), 7.37 (t, J=7.9 Hz, 2H), 7.04 (d, J=8.1 Hz, 2H), 6.43 (d, J=1.0 Hz, 2H), 5.11 (s, 4H), 4.67 (sep, J=6.6 Hz, 3H), 1.50 (d, J=6.6 Hz, 11H).

Example 29

Preparation of 2-hydroxy-6-((2-(1-(2,2,2-trifluoroethyl)-1H-pyrazol-5-yl)pyridin-3-yl)methoxy)benzaldehyde (Compound 50)

Step 1:

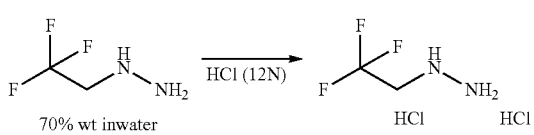 [SMILES: NNCC(F)(F)F ; NNCC(F)(F)F ; Cl ; Cl]

To (3,3,3-trifluoroethyl)hydrazine (25 g, 50% wt in water, 153.5 mmol, 1 eq.) in a RB flask (250 mL) was added HCl (12 N, 25.6 mL, 307.0 mmol, 2 eq.). The mixture was concentrated to give (3,3,3-trifluoroethyl)hydrazine dihydrochloride (1.07 g) as a yellow solid. LRMS (M+H) m/z 129.1.

Step 2:

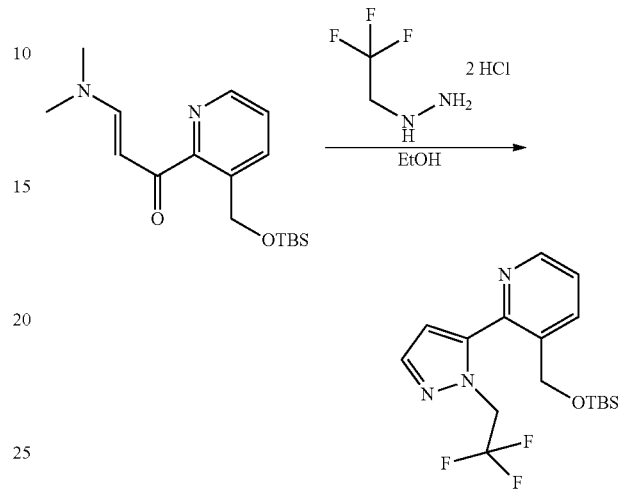

To (E)-1-(3-((tert-butyldimethylsilyloxy)methyl)pyridin-2-yl)-3-(dimethylamino)prop-2-en-1-one (crude above, 5.91 g, 18.44 mmol, 1 eq.) in EtOH (20 mL) was added (3,3,3-trifluoroethyl)hydrazine dihydrochloride (4.13 g, crude above, 22.13 mmol, 1.2 eq.) at rt. The mixture was heated at 80° C. for 1 h, concentrated, and diluted with EtOAc (50 mL) and NaHCO$_{3(sat)}$ solution (10 mL). The layers were separated and aqueous layer was extracted with EtOAc three times. The combined organic layers were dried over Na$_2$SO$_4$, concentrated, and purified on silica gel using a mixture of EtOAc and hexanes as eluent to give 3-((tert-butyldimethylsilyloxy)methyl)-2-(1-(3,3,3-trifluoroethyl)-1H-pyrazol-5-yl)pyridine (5.90 g; 86% for 2 steps). LRMS (M+H$^+$) m/z 372.2.

Step 3:

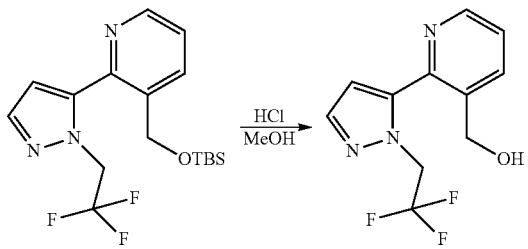 [SMILES: "MeOH" ; CC(C)(C)[Si](C)(C)OCc1cccnc1-c1ccnn1CC(F)(F)F ; Cl ; OCc1cccnc1-c1ccnn1CC(F)(F)F]

To 3-((tert-butyldimethylsilyloxy)methyl)-2-(1-(3,3,3-trifluoroethyl)-1H-pyrazol-5-yl)pyridine (5.91 g, 15.93 mmol) in MeOH (20 mL) was added HCl (4 N, 8.0 mL). The mixture was stirred at rt for 1 h, concentrated, and diluted with EtOAc (50 mL) and NaHCO$_{3(sat)}$ solution (10 mL). The layers were separated and aqueous layer was extracted with EtOAc three times. The combined organic layers were dried over Na$_2$SO$_4$, and concentrated to give (2-(1-(3,3,3-trifluoroethyl)-1H-pyrazol-5-yl)pyridin-3-yl)methanol (4.1 g, quantitative yield) as colorless oil. $^1$H NMR (400 MHz, CDCl$_3$) δ 8.54 (dd, J=4.7, 1.5 Hz, 1H), 7.92 (dd, J=7.9, 1.2 Hz, 1H), 7.57 (d, J=1.9 Hz, 1H), 7.30 (dd, J=7.8, 4.8 Hz, 1H), 6.50 (d, J=1.9 Hz, 1H), 5.09 (q, J=8.6 Hz, 2H), 4.63 (s, 2H), 1.76 (s, 1H). LRMS (M+H$^+$) m/z 272.1

Step 4:

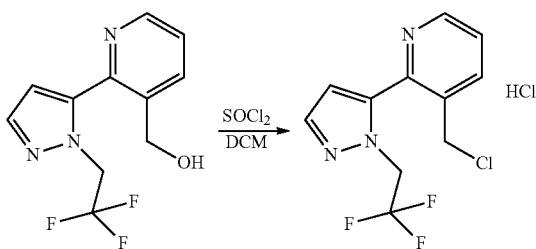

To (2-(1-(2,2,2-trifluoroethyl)-1H-pyrazol-5-yl)pyridin-3-yl)methanol (408 mg, 1.59 mmol) in DCM (5 mL) was added SOCl$_2$ (1.5 mL) at rt. The reaction mixture was stirred at rt for 4 h and concentrated to dryness. The crude solid was suspended in toluene and concentrated to dryness. The process was repeated three times and dried under vacuum to give 3-(chloromethyl)-2-(1-(2,2,2-trifluoroethyl)-1H-pyrazol-5-yl)pyridine hydrochloride (498 mg) as an off-white solid, which was used for next step without further purification.

Step 5:

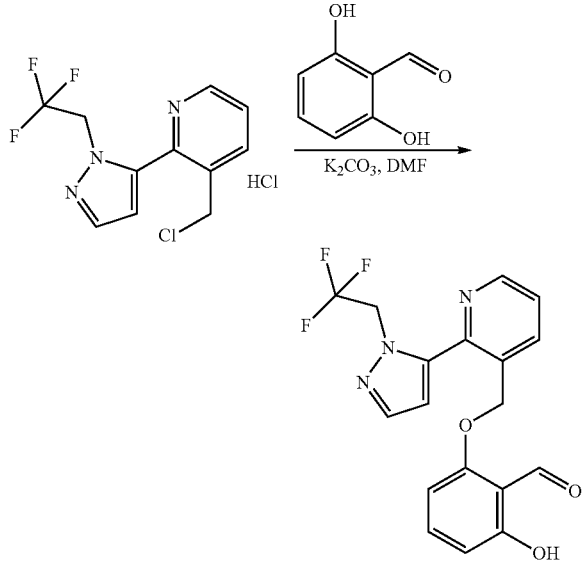

A mixture of 2,6-dihydroxybenzaldehyde (438 mg, 11.47 mmol, 2 eq.) and K$_2$CO$_3$ (2.4 g, 17.22 mmol, 3 eq.) in DMF (150 mL) was stirred at rt for 10 min. To this mixture was added 3-(chloromethyl)-2-(1-(2,2,2-trifluoroethyl)-1H-pyrazol-5-yl)pyridine hydrochloride (498 mg, 1.59 mmol, 1 eq.) at rt. The mixture was heated at 50° C. for 2 h, filtered, concentrated and purified on silica gel using a mixture of EtOAc and hexanes as eluent to 2-hydroxy-6-((2-(1-(2,2,2-trifluoroethyl)-1H-pyrazol-5-yl)pyridin-3-yl)methoxy)benzaldehyde (338.4 mg, 56%) as a pale yellow solid. $^1$H NMR (400 MHz, CDCl$_3$) δ 11.99 (s, 1H), 10.41 (s, 1H), 8.76 (dd, J=4.7, 1.6 Hz, 1H), 8.01 (dd, J=7.9, 1.4 Hz, 1H), 7.69 (d, J=1.9 Hz, 1H), 7.49-7.39 (m, 2H), 6.61 (d, J=8.5 Hz, 1H), 6.53 (d, J=1.9 Hz, 1H), 6.32 (d, J=8.3 Hz, 1H), 5.30 (q, J=8.6 Hz, 2H), 5.17 (s, 2H). LRMS (M+H$^+$) m/z 378.1

Example 30

Preparation of 2-hydroxy-6-((2-(1-(3,3,3-trifluoropropyl)-1H-pyrazol-5-yl)pyridin-3-yl)methoxy)benzaldehyde (Compound 51)

Step 1:

To a mixture of benzyl hydrazinecarboxylate (5.0 g, 30.3 mmol, 1 eq.) and DIEA (15.0 mL, 90.9 mmol, 3 eq.) in DMF (20 mL) was added 3,3,3-trifluoropropyl bromide (10.7 g 60.6 mmol, 2 eq.) at rt. The mixture was heated at 80° C. for 20 h, concentrated, and purified on silica gel using a mixture of EtOAc and hexanes as eluent to benzyl 2-(3,3,3-trifluoropropyl)hydrazinecarboxylate (4.2 g; 53%) as a white solid. $^1$H NMR (400 MHz, CDCl$_3$) δ 7.33-7.17 (m, 5H), 6.11 (s, 1H), 5.01 (s, 2H), 4.00 (s, 1H), 3.00 (dd, J=12.2, 7.1 Hz, 2H), 2.17 (qt, J=10.8, 7.3 Hz, 2H). LRMS (M+H$^+$) m/z 263.1

Step 2:

To benzyl 2-(3,3,3-trifluoropropyl)hydrazinecarboxylate (1.7 g, 6.49 mmol, 1 eq.) in a mixture of EtOH (30 mL) were added Pd/C (1.0 g) and HCl (12 N, 2.0 mL). The mixture was charged with H$_2$ (60 psi), stirred at rt for 1 h, filtered, and concentrated to give (3,3,3-trifluoropropyl)hydrazine dihydrochloride (1.07 g) as a yellow solid. LRMS (M+H) m/z 129.1.

Step 3:

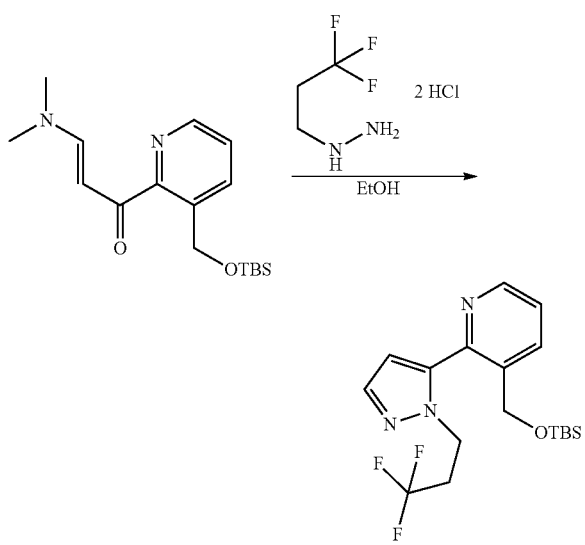

To (E)-1-(3-((tert-butyldimethylsilyloxy)methyl)pyridin-2-yl)-3-(dimethylamino)prop-2-en-1-one (crude above, 1.73 g, 5.41 mmol, 1 eq.) in EtOH (10 mL) was added (3,3,3-trifluoropropyl)hydrazine dihydrochloride (1.30 g, crude above, 6.49 mmol, 1.2 eq.) at rt. The mixture was heated at 80° C. for 1 h, concentrated, and diluted with EtOAc (50 mL) and NaHCO$_{3(sat)}$ solution (10 mL). The layers were separated and aqueous layer was extracted with EtOAc three times. The combined organic layers were dried over Na$_2$SO$_4$, concentrated, and purified on silica gel using a mixture of EtOAc and hexanes as eluent to give 3-((tert-butyldimethylsilyloxy)methyl)-2-(1-(3,3,3-trifluoropropyl)-1H-pyrazol-5-yl)pyridine (1.58 g; 76% for 2 steps). $^1$H NMR (400 MHz, CDCl$_3$) δ 8.53 (dd, J=4.7, 1.6 Hz, 1H), 7.96-7.88 (m, 1H), 7.51 (d, J=1.9 Hz, 1H), 7.29 (dd, J=7.9, 4.7 Hz, 1H), 6.34 (d, J=1.9 Hz, 1H), 4.62 (s, 2H), 4.45-4.33 (m, 2H), 2.82-2.61 (m, 2H), 0.85 (s, 8H), −0.00 (s, 5H). LRMS (M+H$^+$) m/z 386.2.

Step 4:

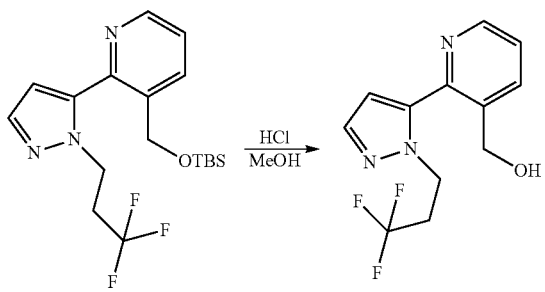 [SMILES: "MeOH" ; CC(C)(C)[Si](C)(C)OCc1cccnc1-c1ccnn1CCC(F)(F)F ; Cl ; OCc1cccnc1-c1ccnn1CCC(F)(F)F]

To 3-((tert-butyldimethylsilyloxy)methyl)-2-(1-(3,3,3-trifluoropropyl)-1H-pyrazol-5-yl)pyridine (1.58 g, 4.1 mmol) in MeOH (20 mL) was added HCl (4 N, 4.0 mL). The mixture was stirred at rt for 1 h, concentrated, and diluted with EtOAc (50 mL) and NaHCO$_{3(sat)}$ solution (10 mL). The layers were separated and aqueous layer was extracted with EtOAc three times. The combined organic layers were dried over Na$_2$SO$_4$, and concentrated to give (2-(1-(3,3,3-trifluoropropyl)-1H-pyrazol-5-yl)pyridin-3-yl)methanol (1.1 g, 99%) as colorless oil. $^1$H NMR (400 MHz, CDCl$_3$) δ 8.64 (dd, J=4.7, 1.7 Hz, 1H), 8.00 (dd, J=7.9, 1.7 Hz, 1H), 7.57 (d, J=1.9 Hz, 1H), 7.38 (dd, J=7.9, 4.8 Hz, 1H), 6.48 (d, J=1.9 Hz, 1H), 4.69 (s, 2H), 4.51-4.43 (m, 2H), 2.85-2.72 (m, 2H), 2.70 (s, 1H). LRMS (M+H$^+$) m/z 272.1.

Step 5:

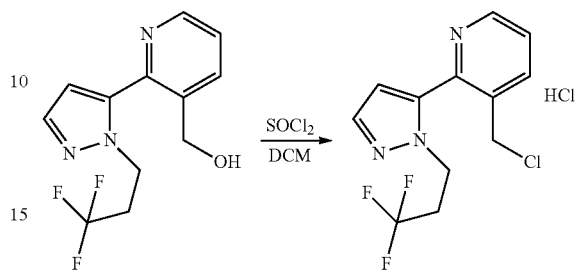

To (2-(1-(2,2,2-trifluoropropyl)-1H-pyrazol-5-yl)pyridin-3-yl)methanol (140 mg, 0.52 mmol) in DCM (5 mL) was added SOCl$_2$ (2.0 mL) at rt. The reaction mixture was stirred at rt for 4 h and concentrated to dryness. The crude solid was suspended in toluene and concentrated to dryness. The process was repeated three times and dried under vacuum to give 3-(chloromethyl)-2-(1-(2,2,2-trifluoropropyl)-1H-pyrazol-5-yl)pyridine hydrochloride (498 mg) as an off-white solid, which was used for next step without further purification.

Step 6:

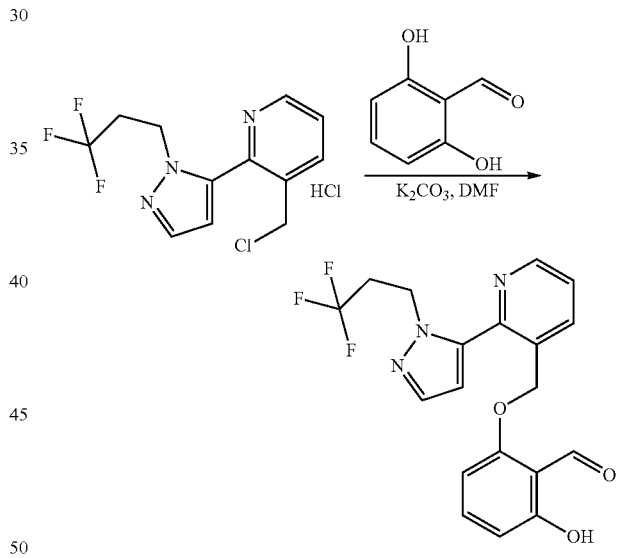

A mixture of 2,6-dihydroxybenzaldehyde (144 mg, 1.04 mmol, 2 eq.) and K$_2$CO$_3$ (214 mg, 1.56 mmol, 3 eq.) in DMF (20 mL) was stirred at rt for 10 min. To this mixture was added 3-(chloromethyl)-2-(1-(2,2,2-trifluoropropyl)-1H-pyrazol-5-yl)pyridine hydrochloride (168 mg, 0.52 mmol, 1 eq.) at rt. The mixture was heated at 50° C. for 2 h, filtered, concentrated and on RP-HPLC (Gemini 21.2×150 mm) using a mixture of CH$_3$CN and water as eluent to give 2-hydroxy-6-((2-(1-(3,3,3-trifluoropropyl)-1H-pyrazol-5-yl)pyridin-3-yl)methoxy)benzaldehyde (53.5 mg, 26%) as an off-white solid. $^1$H NMR (400 MHz, CDCl$_3$) δ 11.98 (s, 1H), 10.38 (s, 1H), 8.77 (dd, J=4.7, 1.6 Hz, 1H), 8.01 (dd, J=7.9, 1.6 Hz, 1H), 7.61 (d, J=1.9 Hz, 1H), 7.49-7.39 (m, 2H), 6.61 (d, J=8.5 Hz, 1H), 6.44 (d, J=1.9 Hz, 1H), 6.34 (d, J=8.2 Hz, 1H), 5.15 (s, 2H), 4.56 (dd, J=8.3, 6.7 Hz, 2H), 3.02-2.72 (m, 2H). LRMS (M+H$^+$) m/z 392.1.

Example 31

Preparation of Benzaldehyde Derivatives

Compounds 52-55 were prepared according to the methods described above.

2-Fluoro-6-((2-(1-(2,2,2-trifluoroethyl)-1H-pyrazol-5-yl)pyridin-3-yl)methoxy)benzaldehyde (Compound 52). $^1$H NMR (400 MHz, CDCl$_3$) δ 10.51 (s, 1H), 8.74 (dd, J=4.7, 1.6 Hz, 1H), 8.21 (dd, J=7.9, 1.6 Hz, 1H), 7.70 (d, J=1.9 Hz, 1H), 7.54-7.41 (m, 2H), 6.82 (dd, J=10.0, 8.6 Hz, 1H), 6.70 (d, J=8.5 Hz, 1H), 6.56 (d, J=1.9 Hz, 1H), 5.28 (q, J=8.6 Hz, 2H), 5.20 (s, 2H).

2-Fluoro-6-((2-(1-(3,3,3-trifluoropropyl)-1H-pyrazol-5-yl)pyridin-3-yl)methoxy)benzaldehyde (Compound 53). $^1$H NMR (400 MHz, CDCl$_3$) δ 10.50 (s, 1H), 8.75 (dd, J=4.7, 1.6 Hz, 1H), 8.22 (dd, J=7.9, 1.6 Hz, 1H), 7.62 (d, J=1.9 Hz, 1H), 7.54-7.42 (m, 2H), 6.83 (dd, J=10.0, 8.7 Hz, 1H), 6.73 (d, J=8.5 Hz, 1H), 6.46 (d, J=1.9 Hz, 1H), 5.19 (s, 2H), 4.59-4.51 (m, 2H), 2.96-2.76 (m, 2H).

2-Fluoro-6-((2-(1-isopropyl-1H-pyrazol-5-yl)pyridin-3-yl)methoxy)benzaldehyde (Compound 54). $^1$H NMR (400 MHz, CDCl$_3$) δ 10.41 (s, 1H), 8.66 (dd, J=4.7, 1.6 Hz, 1H), 8.13 (dd, J=7.9, 1.4 Hz, 1H), 7.55 (d, J=1.8 Hz, 1H), 7.46-7.29 (m, 2H), 6.72 (dd, J=10.0, 8.7 Hz, 1H), 6.59 (d, J=8.5 Hz, 1H), 6.29 (d, J=1.8 Hz, 1H), 5.03 (s, 2H), 4.56 (sep, J=6.7 Hz, 1H), 1.40 (d, J=6.6 Hz, 6H).

Example 32

Preparation of 1-(2-formyl-3-hydroxyphenethyl)piperidine-4-carboxylic acid (Compound 55)

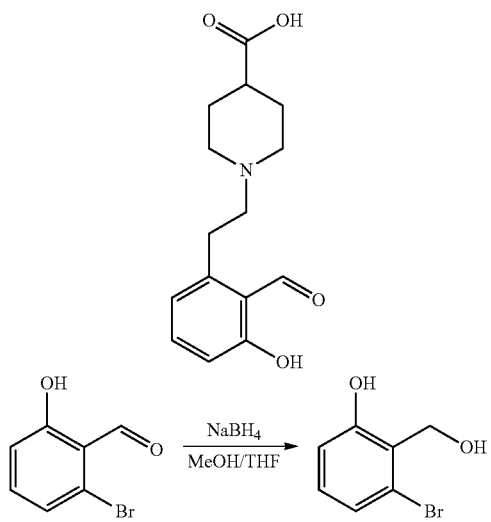

To a solution of 2-bromo-6-hydroxybenzaldehyde (3.8 g, 18.91 mmol, 1 eq.) in a mixture of THF and MeOH (4/1, 25 mL) was added NaBH$_4$ (1.4 g, 37.81 mmol, 1.5 eq.) at rt portion-wise. Upon the completion of addition, the mixture was continued to stir at rt for 30 min. The mixture was quenched with HCl (4 N) and extracted with EtOAC twice. The combined organic layer was dried over Na$_2$SO$_4$, concentrated, and purified on silica gel using 25% EtOAc/hexanes as eluent to give 3-bromo-2-(hydroxymethyl)phenol (2.3 g, 60%) as a colorless oil.

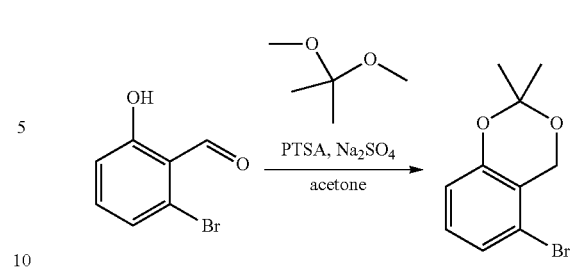

To 3-bromo-2-(hydroxymethyl)phenol (2.3 g, 11.3 mmol, 1 eq.) in acetone (20.0 mL) were added 2,2-dimethoxypropane (6.0 mL), PTSA (215 mg, 1.13 mmol, 0.1 eq.), and Na$_2$SO$_4$ (5.0 g). The mixture was heated at 40° C. O/N, cooled to rt, and diluted with EtOAc.

The organic layer was washed with NaHCO$_{3(sat.)}$ solution and brine, dried over Na$_2$SO$_4$, concentrated, and purified on silica gel using a mixture of EtOAc and hexanes to give 5-bromo-2,2-dimethyl-4H-benzo[d][1,3]dioxine (2.1 g, 76%) as a colorless oi. $^1$H NMR (400 MHz, CDCl$_3$) δ 7.13 (dd, J=8.0, 1.2 Hz, 1H), 7.07 (t, J=8.0 Hz, 1H), 6.81 (dd, J=8.0, 1.2 Hz, 1H), 4.77 (s, 2H), 1.56 (s, 6H).

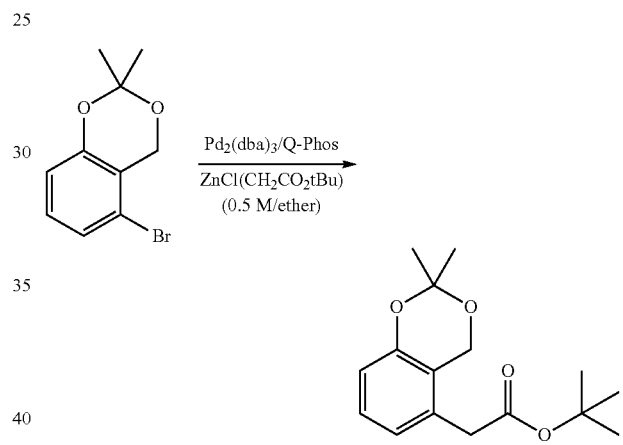

To a mixture of 5-bromo-2,2-dimethyl-4H-benzo[d][1,3]dioxine (2.1 g, 8.64 mmol, 1 eq.), Pd$_2$(dba)$_3$ (400 mg, 0.43 mmol, 0.05 eq.), Q-Phos (460 mg, 0.65 mmol, 0.075 mmol) in THF (100 mL) purged with N$_2$ for 10 min was added ZnCl(CH$_2$CO$_2^t$Bu) (0.5 M/ether, 35 mL, 17.38 mmol, 2 eq.). The mixture was heated at 50° C. for 16 h, cooled to rt, added NH$_4$Cl(sat) solution, and diluted with EtOAc. The organic layer was separated, dried over Na$_2$SO$_4$, concentrated, and purified on silica gel using a mixture of EtOAc and hexanes to give tert-butyl 2-(2,2-dimethyl-4H-benzo[d][1,3]dioxin-5-yl)acetate (2.6 g, 80% pure, 87%) as a brown oil. $^1$H NMR (400 MHz, CDCl$_3$) δ 7.06 (t, J=7.9 Hz, 1H), 6.73 (d, J=7.4 Hz, 1H), 6.68 (d, J=8.2 Hz, 1H), 4.78 (s, 2H), 1.47 (s, 6H), 1.36 (s, 9H).

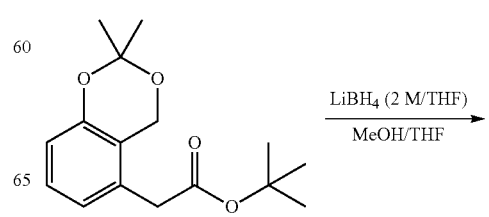

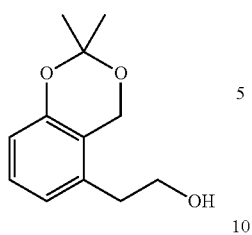

To a solution of tert-butyl 2-(2,2-dimethyl-4H-benzo[d][1,3]dioxin-5-yl)acetate (2.6 g, 80% pure, 9.34 mmol, 1 eq.) in THF (20 mL) were added LiBH$_4$ (7.0 mL, 14.01 mmol, 1.5 eq.) and MeOH (1.0 mL) at rt. The mixture was stirred at rt for 30 min, added MeOH (20 mL), concentrated to dryness, added MeOH (20 mL) and silica gel, and concentrated to dryness again. The mixture was loaded directly on silica gel for purification using a mixture of EtOAc and hexanes as eluent to give 2-(2,2-dimethyl-4H-benzo[d][1,3]dioxin-5-yl)ethanol (1.1 g, 71%) as a pale brown oil. $^1$H NMR (400 MHz, CDCl$_3$) δ 7.28 (t, J=7.9 Hz, 1H), 6.92 (d, J=7.4 Hz, 1H), 6.86 (d, J=8.2 Hz, 1H), 5.02 (s, 2H), 3.99 (q, J=6.4 Hz, 2H), 2.86 (t, J=6.6 Hz, 2H), 1.68 (s, 6H), 1.57 (t, J=5.5 Hz, 1H).

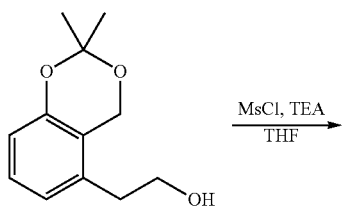

To a solution of 2-(2,2-dimethyl-4H-benzo[d][1,3]dioxin-5-yl)ethanol (400 mg, 1.92 mmol, 1 eq.) in THF (20 mL) were added MsCl (438 mg, 3.84 mmol, 2.0 eq.) and TEA (0.8 mL, 5.76 mmol, 3.0 eq.) at rt. The mixture was stirred at rt for 1 h and diluted with EtOAc. The organic layer was washed with water and brine, dried over Na$_2$SO$_4$, and concentrated to give 2-(2,2-dimethyl-4H-benzo[d][1,3]dioxin-5-yl)ethyl methanesulfonate (400 mg, crude) as a pale brown oil, which was used for next step without purification.

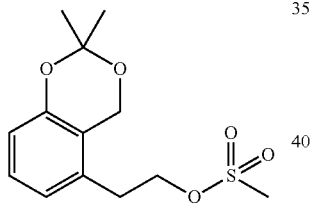

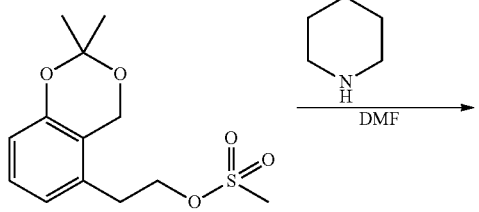

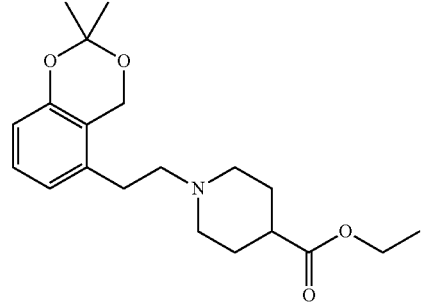

To 2-(2,2-dimethyl-4H-benzo[d][1,3]dioxin-5-yl)ethyl methanesulfonate (176 mg, 0.59 mmol, crude above, 1 eq.) in DMF (1.0 mL) was added ethyl piperidine-4-carboxylate (186 mg, 1.18 mmol, 2.0 eq.) at rt. The mixture was stirred at 60° C. for 2 h, cooled to rt, and purified on RP-HPLC (Gemini 21.2 mm×150 mm) using a mixture of CH$_3$CN and water (0.1% HCOOH) as eluent to give ethyl 1-(2-(2,2-dimethyl-4H-benzo[d][1,3]dioxin-5-yl)ethyl)piperidine-4-carboxylate (100 mg, 49% for two steps). $^1$H NMR (400 MHz, CDCl$_3$) δ 8.45 (s, 1H), 7.13 (t, J=7.9 Hz, 1H), 6.73 (d, J=7.9 Hz, 2H), 4.86 (s, 2H), 4.19 (q, J=7.1 Hz, 2H), 3.22 (s, 2H), 3.09-2.95 (m, 1H), 2.95-2.79 (m, 4H), 2.76 (s, 1H), 2.66-2.48 (m, 1H), 2.23-1.99 (m, 4H), 1.55 (s, 6H), 1.29 (t, J=7.1 Hz, 3H). LRMS (M+H$^+$) m/z 348.1.

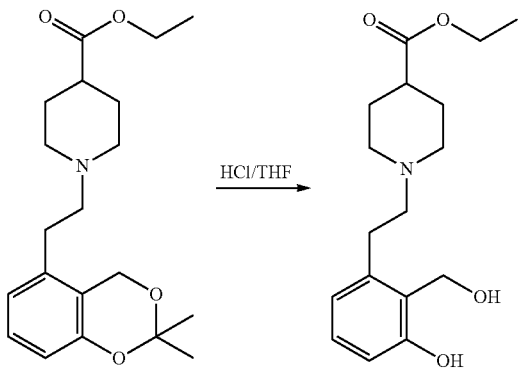 [SMILES: CCOC(=O)C1CCN(CCc2cccc3c2COC(C)(C)O3)CC1 ; CCOC(=O)C1CCN(CCc2cccc(O)c2CO)CC1]

To ethyl 1-(2-(2,2-dimethyl-4H-benzo[d][1,3]dioxin-5-yl)ethyl)piperidine-4-carboxylate (100 mg, 0.49 mmol, 1 eq.) in THF (10 mL) were added HCl (6 N, 10 drops) and water (1.0 mL) at rt. The mixture was stirred at 60° C. for 2 h, cooled, and basified with NaHCO$_{3(sat.)}$ solution. The mixture was filtered and concentrated. The residue was bring into THF (10 mL) and filtered. The filtrate was concentrated to give ethyl 1-(3-hydroxy-2-(hydroxymethyl)phenethyl)piperidine-4-carboxylate (85 mg, crude) as a pale brown oil, which was used for next step without purification. LRMS (M+H$^+$) m/z 308.1.

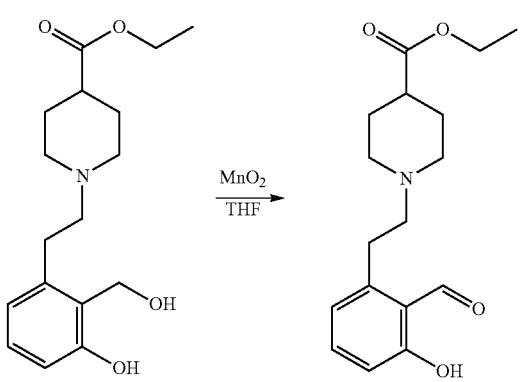 [SMILES: CCOC(=O)C1CCN(CCc2cccc(O)c2CO)CC1 ; "MnO2" ; CCOC(=O)C1CCN(CCc2cccc(O)c2C=O)CC1 ; "THF"]

To ethyl 1-(3-hydroxy-2-(hydroxymethyl)phenethyl)piperidine-4-carboxylate (85 mg, crude above) in THF (20.0 mL) was added MnO$_2$ (500 mg, 5.75 mmol) at rt. The mixture was stirred at rt for 1 h, filtered, and concentrated to give ethyl 1-(2-formyl-3-hydroxyphenethyl)piperidine-4-carboxylate (80 mg, crude) as a pale brown solid, which was used for next step with purification. LRMS (M+H$^+$) m/z 306.1.

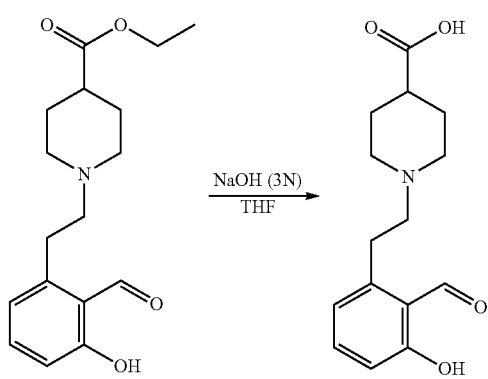 [SMILES: CCOC(=O)C1CCN(CCc2cccc(O)c2C=O)CC1 ; O=Cc1c(O)cccc1CCN1CCC(C(=O)O)CC1 ; "THF"]

To ethyl 1-(2-formyl-3-hydroxyphenethyl)piperidine-4-carboxylate (80 mg, crude above) in THF (5.0 mL) was added NaOH (3 N, 1.0 mL). The mixture was stirred at rt for 2 h and acidified to pH 3-4 using HCl (2 N). The mixture was concentrated and purified on RP-HPLC (Gemini 21.2 mm×150 mm) using a mixture of CH$_3$CN and water (0.1% HCOOH) as eluent to give 1-(2-formyl-3-hydroxyphenethyl)piperidine-4-carboxylic acid (40 mg, 29% for three steps) as a yellow solid. $^1$H NMR (400 MHz, DMSO) δ 10.26 (s, 1H), 8.65 (s, 2H), 6.91 (dd, J=8.7, 6.9 Hz, 1H), 6.16 (d, J=7.9 Hz, 1H), 5.76 (d, J=6.7 Hz, 1H), 3.01-2.89 (m, 4H), 2.50-2.36 (m, 2H), 2.03 (t, J=10.3 Hz, 2H), 1.92-1.76 (m, 3H), 1.69-1.49 (m, 2H). LRMS (M+H$^+$) m/z 278.4. $^1$H NMR (400 MHz, DMSO-d6) δ 10.1 (s, 1H), 8.55 (s, 2H), 6.75 (dd, J=Hz, 1H), 6.05 (d, J=Hz, 1H), 5.6 (d, J=Hz, 1H), 2.7 (m, 4H), 2.3 (m, 2H), 1.85 (m, 2H), 1.7 (m, 3H), 1.5 (m, 2H).
In Vitro Testing Example 33

Modulation of Hemoglobin Oxygen affinity by Substituted Benzaldehyde Compounds

Assay Procedure

Oxygen equilibrium curves (OEC) in purified Hemoglobin S (HbS) were measured by the change in p50, the partial pressure of oxygen at which the heme binding sites in the HbS sample are 50% saturated with oxygen. HbS was purified by a modified procedure (Antonini and Brunori, 1971; Heomoglobin and Myoglobin in their Reactions with Ligands; North Holland Publishing Company; Amsterdam, London) from blood obtained from homozygous sickle cell patients though the Hemoglobinopathy Center at Children's Hospital Oakland Research Institute (CHORI) with Institutional Review Board approval. Oxygen equilibrium curves were carried out with a HEMOX analyzer, (TCS Scientific, New Hope, Pa.). Five hundred μL of 250 μM purified HbS were diluted into 4.5 mL of HEMOX buffer (30 mM TES, 130 mM NaCl, 5 mM KCl, pH=7.4) resulting in a final hemoglobin concentration of 25 μM. The compounds were added at the final desired concentrations. The mixture was incubated for 45 min at 37° C. and then transferred to the Hemox sample chamber. The samples were saturated with oxygen by flushing with compressed air for 10 minutes. The samples were then flushed with pure nitrogen and the absorbance of deoxy-Hb was recorded as a function of the solution pO$_2$. The oxygen equilibrium data was then fit to the Hill Model to obtain values for p50. The deoxygenation curves for both HbS alone (control) and HbS in the presence of compound were collected with the TCS software. The p50 for purified Hbs was typically 13.8±1.6. Delta p50 values were obtained from the p50 value for control minus the p50 value for HbS treated with compound divided by the p50 value for the control. A positive delta p50 value corresponds to a left shifted curve and a lower p50 value relative to control, indicating that the compound acts to modulate HbS to increase its affinity for oxygen.

Example 34

Modulation of Hemoglobin Oxygen affinity by Substituted Benzaldehyde Compounds

Assay Results

The compounds of Table 1 that were where tested in the assay above were all found to have positive delta p50 values. Delta p50% is calculated from [[p50(HbS)−p50(HbS treated with compound)]/p50(HbS)]×100. Table 2 below lists the delta p50% values where + indicates a delta p50% of between 0 and 29 and ++ indicates a delta p50% of 30 or greater. Unless noted otherwise, the compounds in Table 2 were tested at 30 μM.

TABLE 2

| Compound | delta p50 |
|---|---|
| 1 | ++ |
| 2 | + |
| 3 | + (100 μM) |
| 4 | + |
| 5 | ++ |
| 6 | + (100 μM) |
| 7 | ++ |
| 8 | + |
| 9 | + |
| 10 | ++ |
| 11 | + |
| 12 | + (100 μM) |
| 13 | + |
| 14 | + |
| 15 | + (100 μM) |
| 16 | + |
| 21 | + (100 μM) |

TABLE 2-continued

| Compound | delta p50 |
|---|---|
| 23 | ++ |
| 24 | ++ |
| 25 | ++ |
| 33 | + (100 μM) |
| 34 | + |
| 35 | + |
| 37 | + |
| 38 | ++ (100 μM) |
| 39 | + (100 μM) |
| 40 | + |
| 41 | |
| 42 | |
| 43 | |
| 44 | |
| 45 | |

Example 35

Polymerization Assay

Polymerization assays are carried out in vitro using purified HBS exchanged into 1.8 M potassium phosphate buffer at pH 7.4. Using a slightly modified protocol (Antonini and Brunori, 1971), HbS is purified by the CRO VIRUSYS, from blood obtained from homozygous sickle cell patients through the Hemoglobinopathy Center at Children's Hospital Oakland Research Institute (CHORI) with Institutional Review Board approval. Compounds are prepared in 100% DMSO and a desired amount is added to 50 μM of purified HBS at a final DMSO concentration of 0.3%. Final potassium phosphate concentration is adjusted to 1.8 M using a combination of 2.5 M potassium phosphate stock solution and water at pH 7.4. The reaction mixture is incubated for an hour at 37° C. and then transferred into a 24-well plate for deoxygenation in a glove box containing 99.5% nitrogen and 0.5% oxygen. The 24-well plate is not covered and incubated at 4° C. on a plate cooler inside the glove box for one and a half hours. Fifty L of the reaction mixture is transferred into a 96-well plate and the absorbance at 700 nm is measured every minute for one hour at 37° C. in a plate reader located inside the glove box. A plot of the absorbance against time is fitted using a Boltzman sigmoidal fit and the delay time (from zero to time at half Vmax) is measured. To compare and rank compounds, delay times are expressed as percent delay (% DT), which is defined as the difference in delay times for HBS/compound and HBS alone multiplied by 100 and divided by the delay time for HBS alone.

Compounds listed below have been tested in the polymerization assay. Activity ranges are defined by the number of dagger (†) symbols indicated. † denotes activity ≥40% but ≤80%; †† denotes activity >80% but ≤120%; ††† denotes activity >120% but ≤140%; †††† denotes activity >160%.

| Compound | % delta Delay |
|---|---|
| 42 | †† |
| 43 | †† |
| 44 | † |
| 45 | †† |
| 46 | † |
| 47 | †† |
| 48 | † |
| 49 | † |

Example 36

R/T Assay

A relaxed-to-tense transition assay ("R/T assay") was used to determine the ability of substituted benzaldehyde compounds to maintain the high-oxygen affinity relaxed (R) state of hemoglobin under deoxygenated conditions. This ability can be expressed as a "delta R" value (i.e., the change in the time-period of the R state after hemoglobin is treated with a compound, as compared to the period without treatment with the compound). Delta R is the % R to remaining after the compounds treatment compared with no treatment (e.g. if R % without treatment is 8% while with treatment with a target compound is 48% R at 30 μM, then % R is 40% for that compound.

A mixture of HbS/A was purified from blood obtained from homozygous sickle cell patients though the Hemoglobinopathy Center at Children's Hospital Oakland Research Institute (CHORI) with Institutional Review Board approval. HbS/A (at a final concentration of 3 μM) was incubated for 1 hr at 37° C. in presence or absence of compounds in 50 μM potassium phosphate buffer, pH=7.4 and 30 μM 2,3 diphosphoglycerate (DPG) in 96 well plates in a final volume of 160 μl. Compounds were added at different concentrations (3 μM to 100 μM final concentrations). Plates were covered with a Mylar film. After incubation was completed the Mylar cover was removed and the plates were placed in a Spectrostar Nano plate reader previously heated at 37° C. Five minutes later, $N_2$ (flow rate=20 L/min) was flowed through the spectrophotometer. Spectroscopic measurements (300 nm to 700 nm) were taken every 5 min for 2 hours. Data analysis was performed by using linear regression from the data retrieved for all wavelengths.

Table 4 below lists the delta R values where + indicates a delta R of between 0 and 30, ++ indicates a delta R of between 30 and 50, and +++ indicates a delta R of 50 or greater. Unless noted otherwise, the compounds in Table 2 were tested at 9 μM.

TABLE 3

| Compound | delta R (%) |
|---|---|
| 5 | ++ |
| 10 | ++ |
| 24 | + |
| 25 | ++ |
| 41 | + |
| 42 | +++ (30 μm) |
| 43 | +++ (30 μm) |
| 44 | +++ |
| 45 | +++ |

Example 37

Whole Blood Assay

Oxygen Equilibrium Curves (OEC) of whole blood before and after treatment with different concentrations of substituted benzaldehyde compounds were performed as follows using a HEMOX analyzer (TCS Scientific, New Hope, Pa.). Blood samples from homozygous sickle cell patients were obtained though the Hemoglobinopathy Center at Children's Hospital Oakland Research Institute (CHORI) with Institutional Review Board approval. The hematocrit was adjusted to 20% using autologous plasma and the blood samples were incubated for 1 hour at 37° C. in absence or presence of compounds. 100 µl of these samples were added to 5 mL of Hemox buffer (30 mM TES, 130 mM NaCl, 5 mM KCl, pH=7.4) at 37° C. and then transferred to the Hemox sample chamber. The samples were saturated with oxygen by flushing with compressed air for 10 minutes. The samples were then flushed with pure nitrogen and the respective absorbances of oxy- and deoxy-Hb are recorded as a function of the solution pO2. The oxygen equilibrium data were then fitted to the Hill Model to obtain values for p50. The deoxygenation curves for both whole blood alone (control) and whole blood in the presence of the compound were collected with the TCS software.

Table 5 below lists the delta p50% values where + indicates a delta p50% of between 0 and 29, ++ indicates a delta p50% of between 30 and 50, and +++ indicates a delta p50% of 50 or greater. The compounds in Table 2 were tested at 1000 µM. A positive delta p50 value corresponds to a left shifted curve and a lower p50 value relative to control, indicating that the compound acts to modulate HbS to increase its affinity for oxygen.

TABLE 4 delta p50% Values for Whole Blood Assay

| Compound | delta p50% |
|---|---|
| 42 | + |
| 43 | +++ |
| 44 | + |
| 45 | + |

TABLE 5

Compound 43 7.8 mpk IV in rat

| time | blood conc (uM) | | | plasma conc (uM) | | |
|---|---|---|---|---|---|---|
| (min) | A | B | C | A | B | C |
| 0 | BLLOQ | BLLOQ | BLLOQ | BLLOQ | BLLOQ | BLLOQ |
| 5 | 259 | 246 | 281 | 7.56 | 8.68 | 7.44 |
| 15 | 287 | 341 | 285 | 8.38 | 8.42 | 7.16 |
| 30 | 283 | 333 | 292 | no sample | 8.66 | 7.1 |
| 60 | 256 | 203 | 285 | 6.12 | 7.52 | 7.22 |
| 120 | 263 | 274 | 280 | 3.92 | 6.02 | 5.22 |
| 240 | 248 | 225 | 259 | 3.72 | 5.24 | 5.88 |
| 480 | 118 | 136 | 22.9 | 2.06 | 2.66 | 3.15 |
| 1440 | 81.1 | 85 | 70.8 | 1.07 | 1.38 | 1.51 |

TABLE 6

Compound 43 7.8mpk IV in rat

| | | Blood | Plasma |
|---|---|---|---|
| t½ beta | min | 749.0 | 619.1 |
| CL | ml/min/kg | 0.08 | 4.45 |
| Vss | L/kg | 0.09 | 4.11 |
| AUClast | min * umol/L | 215846.3 | 4114.8 |

Example 38

Pharmacokinetic Study of Compound 43(HCl Salt)

I.V. Study

Sprague Dawley rats were treated with 7.8 mg/Kg of Compound 43 dissolved in 10% DMA:50% PEG:16% ca vitron. At specified time points 10 uL of whole blood/plasma was removed from rats and treated with 490 ul pH 3 buffer+500 uL ACN/IS, then shaken for 1 hour, centrifuged for 10 minutes at 57 rpm at 4 C. The supernatant was transferred to a filter plate and centrifuged at 2000 rpm for 1 minute at 4 C. The samples were then analyzed by LC-MS/MS monitoring parent aldehyde. Concentrations in blood and plasma are shown in Table 5. Key P/K parameters are shown in Table 6.

Oral Study

SD Rats were treated by gavage with 44 mg/kg and 100 mg/kg dissolved in 10% DMA:90% PEG. At specified time points blood was taken and worked up as described above in the IV Study. Key Parameters are shown in Table 7.

TABLE 7

Compound 43: 2 PO in rats

| | | Blood | | | Plasma | | |
|---|---|---|---|---|---|---|---|
| | | | | ratio | | | ratio |
| dose | mg/kg | 44 | 100 | 2.27 | 44 | 100 | 2.27 |
| Tmax | min | 320.00 | 720.00 | | 200.00 | 680.00 | |
| Cmax | umol/L | 381.33 | 1096.67 | 2.88 | 14.79 | 44.53 | 3.01 |
| AUClast | min*umol/L | 395638.27 | 1384101.11 | 3.50 | 12517.54 | 52836.17 | 4.22 |

All patents, patent applications, publications and presentations referred to herein are incorporated by reference in their entirety. Any conflict between any reference cited herein and the teaching of this specification is to be resolved in favor of the latter. Similarly, any conflict between an art-recognized definition of a word or phrase and a definition of the word or phrase as provided in this specification is to be resolved in favor of the latter.

What is claimed is:

1. A compound selected from the group consisting of:
having the formula:

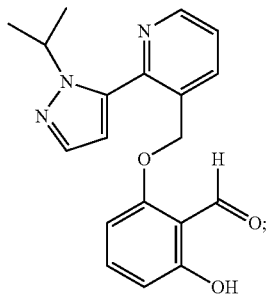 [SMILES: CC(C)n1nccc1-c1ncccc1COc1cccc(O)c1C=O]

2-hydroxy-6-((2-(1-isopropyl-1H-pyrazol-5-yl)pyridin-3-yl)methoxy)benzaldehyde,

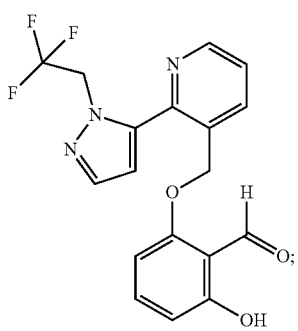 [SMILES: O=Cc1c(O)cccc1OCc1cccnc1-c1ccnn1CC(F)(F)F]

2-hydroxy-6-((2-(1-(2,2,2-trifluoroethyl)-1H-pyrazol-5-yl)pyridin-3-yl)methoxy)benzaldehyde, and

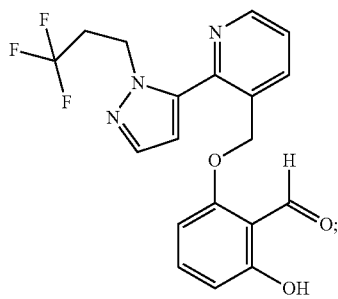 [SMILES: O=Cc1c(O)cccc1OCc1cccnc1-c1ccnn1CCC(F)(F)F]

2-hydroxy-6-((2-(1-(3,3,3-trifluoropropyl)-1H-pyrazol-5-yl)pyridin-3-yl)methoxy)benzaldehyde,
or pharmaceutically acceptable salt thereof.

2. The compound according to claim 1:
having the formula:

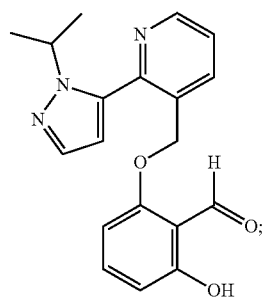 [SMILES: CC(C)n1nccc1-c1ncccc1COc1cccc(O)c1C=O]

2-hydroxy-6-((2-(1-isopropyl-1H-pyrazol-5-yl)pyridin-3-yl)methoxy)benzaldehyde
or pharmaceutically acceptable salt thereof.

3. The compound of claim 1 having the formula:

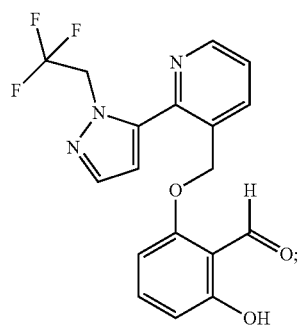 [SMILES: O=Cc1c(O)cccc1OCc1cccnc1-c1ccnn1CC(F)(F)F]

2-hydroxy-6-((2-(1-(2,2,2-trifluoroethyl)-1H-pyrazol-5-yl)pyridin-3-yl)methoxy)benzaldehyde; or pharmaceutically acceptable salt thereof.

4. The compound of claim 1 having the formula:

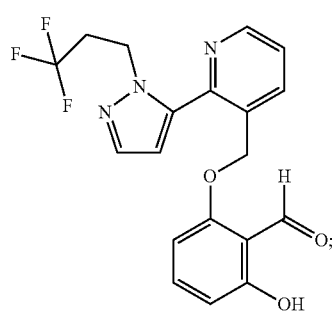 [SMILES: O=Cc1c(O)cccc1OCc1cccnc1-c1ccnn1CCC(F)(F)F]

2-hydroxy-6-((2-(1-(3,3,3-trifluoropropyl)-1H-pyrazol-5-yl)pyridin-3-yl)methoxy)benzaldehyde; or pharmaceutically acceptable salt thereof.

5. A pharmaceutical composition comprising a compound of claim 3.

6. A pharmaceutical composition comprising a compound of claim 2 or pharmaceutically acceptable salt thereof.

* * * * *